United States Patent
Onuki et al.

(10) Patent No.: US 9,456,736 B2
(45) Date of Patent: Oct. 4, 2016

(54) ENDOSCOPE, AND TREATMENT INSTRUMENT FOR ENDOSCOPE

(71) Applicant: Olympus Corporation, Tokyo (JP)

(72) Inventors: Yoshio Onuki, Tokyo (JP); Kiyotaka Matsuno, Tokyo (JP); Tatsutoshi Hashimoto, Tokyo (JP); Tsutomu Okada, Tokyo (JP); Kazuo Banju, Tokyo (JP); Ken Shigeta, Tokyo (JP); Naoki Iwanaga, Tokyo (JP); Shotaro Takemoto, Tokyo (JP); Ayano Ishioka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 47 days.

(21) Appl. No.: 14/279,715

(22) Filed: May 16, 2014

(65) Prior Publication Data

US 2014/0296632 A1 Oct. 2, 2014

Related U.S. Application Data

(63) Continuation of application No. 13/622,824, filed on Sep. 19, 2012, now Pat. No. 8,771,171, which is a continuation of application No. PCT/JP2012/053684, filed on Feb. 16, 2012.

(60) Provisional application No. 61/443,427, filed on Feb. 16, 2011.

(51) Int. Cl.
*A61B 1/00* (2006.01)
*A61B 1/04* (2006.01)
(Continued)

(52) U.S. Cl.
CPC ........... *A61B 1/005* (2013.01); *A61B 1/00039* (2013.01); *A61B 1/00045* (2013.01);
(Continued)

(58) Field of Classification Search
USPC ........ 600/104, 106, 107, 114, 115, 116, 127, 600/128, 129, 130, 139–152; 604/523–528; 606/1
See application file for complete search history.

(56) References Cited

U.S. PATENT DOCUMENTS

| 5,876,325 A | 3/1999 | Mizuno et al. |
|---|---|---|
| 2004/0138529 A1* | 7/2004 | Wiltshire et al. ............. 600/144 |

(Continued)

FOREIGN PATENT DOCUMENTS

| CN | 1925783 A | 3/2007 |
|---|---|---|
| CN | 101569520 A | 11/2009 |

(Continued)

OTHER PUBLICATIONS

Apr. 29, 2014 Extended European Search Report issued in European Patent Application No. 12747736.2.

(Continued)

*Primary Examiner* — Ryan Henderson
(74) *Attorney, Agent, or Firm* — Oliff PLC

(57) ABSTRACT

A medical instrument system includes an elongated member having an inner space in a direction of a longitudinal axis, an insertion section installed at the inner space and having a bending section capable of being bent, a manipulation section configured to manipulate the bending section, a first manipulation member transmitting a driving force of the bending section in accordance with the manipulation by the manipulation section, a second manipulation member arranged in the direction of a longitudinal axis, a connecting section having a first connecting section and a second connecting section and capable of connecting the first manipulation member and the second manipulation member, and a switching mechanism having a first acting section and a second acting section and switching between a connection state and a release state in accordance with a relative movement between the elongated member and the insertion section.

4 Claims, 68 Drawing Sheets

(51) Int. Cl.
A61M 25/00 (2006.01)
A61B 17/00 (2006.01)
A61B 1/005 (2006.01)
A61B 1/05 (2006.01)
A61B 1/12 (2006.01)
A61B 1/018 (2006.01)
A61M 25/01 (2006.01)
A61B 17/04 (2006.01)
A61B 17/062 (2006.01)
A61B 1/012 (2006.01)
A61B 1/015 (2006.01)
A61B 17/29 (2006.01)

(52) U.S. Cl.
CPC ........... *A61B1/0052* (2013.01); *A61B 1/0057* (2013.01); *A61B 1/00075* (2013.01); *A61B 1/00098* (2013.01); *A61B 1/00114* (2013.01); *A61B 1/00121* (2013.01); *A61B 1/00128* (2013.01); *A61B 1/00135* (2013.01); *A61B 1/00154* (2013.01); *A61B 1/018* (2013.01); *A61B 1/0125* (2013.01); *A61B 1/051* (2013.01); *A61B 1/12* (2013.01); *A61B 17/00234* (2013.01); *A61B 17/0469* (2013.01); *A61B 17/062* (2013.01); *A61M 25/0136* (2013.01); *A61M 25/0147* (2013.01); *A61B 1/0055* (2013.01); *A61B 1/00094* (2013.01); *A61B 1/015* (2013.01); *A61B 2017/0034* (2013.01); *A61B 2017/2905* (2013.01)

(56) References Cited

U.S. PATENT DOCUMENTS

| | | | |
|---|---|---|---|
| 2005/0119527 A1* | 6/2005 | Banik et al. | 600/117 |
| 2005/0272975 A1 | 12/2005 | McWeeney et al. | |
| 2006/0094932 A1 | 5/2006 | Goldfarb et al. | |
| 2006/0252993 A1 | 11/2006 | Freed et al. | |
| 2007/0015965 A1 | 1/2007 | Cox et al. | |
| 2008/0262293 A1 | 10/2008 | Murakami et al. | |
| 2008/0287735 A1 | 11/2008 | Takemoto et al. | |
| 2010/0063354 A1 | 3/2010 | Hashimoto et al. | |
| 2010/0217072 A1 | 8/2010 | Kondoh et al. | |

FOREIGN PATENT DOCUMENTS

| | | |
|---|---|---|
| EP | 1 554 974 A1 | 7/2005 |
| EP | 1 721 568 A1 | 11/2006 |
| EP | 1 849 415 A2 | 10/2007 |
| EP | 2 108 304 A2 | 10/2009 |
| JP | U-56-158207 | 11/1981 |
| JP | U-61-67710 | 5/1986 |
| JP | A-04-210039 | 7/1992 |
| JP | A-07-155287 | 6/1995 |
| JP | A-07-328024 | 12/1995 |
| JP | 2000023902 A | 1/2000 |
| JP | A-2000-023902 | 1/2000 |
| JP | 2001231747 A | 8/2001 |
| JP | A-2001-231747 | 8/2001 |
| JP | A-2005-205030 | 8/2005 |
| JP | A-2005-296305 | 10/2005 |

OTHER PUBLICATIONS

Jan. 29, 2013 Office Action issued in Japanese Patent Application No. 2012-266582 (with English translation).
May 15, 2012 International Search Report issued in International Patent Application No. PCT/JP2012/053684.
Jun. 27, 2013 Election of Species Requirement issued in U.S. Appl. No. 13/622,824.
Nov. 7, 2013 Office Action issued in U.S. Appl. No. 13/622,824.
Feb. 25, 2014 Notice of Allowance issued in U.S. Appl. No. 13/622,824.
Sep. 22, 2014 Office Action issued in Chinese Patent Application No. 201280002748.4 with English Translation.
Nov. 11, 2015 Search Report issued in European Patent Application No. 15161064.9.
Mar. 1, 2016 Extended European Search Report issued in European Patent Application No. 15161064.9.

* cited by examiner

ENDOSCOPE, AND TREATMENT INSTRUMENT FOR ENDOSCOPE

This is a Continuation of application Ser. No. 13/622,824 filed Sep. 19, 2012, which is a continuation application based on a PCT Patent Application No. PCT/JP2012/053684, filed Feb. 16, 2012, whose priority is claimed on U.S. Provisional Patent Application No. 61/443,427, filed Feb. 16, 2011. The disclosure of the prior applications is hereby incorporated by reference herein in its entirety.

BACKGROUND OF THE INVENTION

1. Field of the Invention

The present invention relates to an endoscope inserted into a body cavity and used when treating various tissues in the body cavity while observing the various tissues, and a treatment instrument for an endoscope that can be appropriately applied to the endoscope.

2. Description of Related Art

In the related art, as an example of a minimum invasive treatment, various procedures such as cholecystectomy, or the like, using a laparoscope or the like, are performed. Such a laparoscope surgery is performed in a manner in which a plurality of holes are opened in the abdominal wall and a plurality of instruments are inserted thereinto.

In recent times, in order to lighten the burden of a patient by reducing the number of holes opened in the abdominal wall, it has been proposed that a soft endoscope is inserted into natural holes such as the mouth or the nose, the anus, or the like, of the patient to perform a procedure. As a medical instrument used in such a procedure, for example, a medical instrument disclosed in United States Patent Publication Application No. 2010/0063354 has been proposed.

The medical instrument has a soft insertion section having flexibility, and an observation unit and a pair of arm sections having bending sections configured to perform a bending motion are installed at an insertion section distal end. A plurality of channel disposed at the insertion section is in communication with inner cavities of arm sections thereof.

A manipulation section configured to manipulate the arm sections is connected to the arm sections via manipulation members, and enables bending manipulation of the arm sections in four directions spaced apart from an axis thereof.

A user appropriately selects a treatment instrument, such as forceps, and inserts the treatment instrument into a channel of a medical instrument. The user mounts the manipulation section of the treatment instrument on the manipulation section of the medical instrument, and makes a distal end of the treatment instrument protrude from the arm sections. Then, as the user manipulates the manipulation section while observing a tissue of a treatment target (a target tissue) or the like using an observation unit, the user brings the distal end of the treatment instrument close to the target tissue from a different direction and performs a procedure on the target tissue.

SUMMARY OF THE INVENTION

According to a first aspect of the present invention, a medical instrument system includes: an elongated member having a longitudinal axis and an inner space in a direction of the longitudinal axis, and formed in the direction of the longitudinal axis; an insertion section installed at the inner space so as to freely move in the direction of the longitudinal axis and having a bending section capable of being bent; a manipulation section configured to manipulate the bending section; a first manipulation member connected to the manipulation section and transmitting a driving force of the bending section in accordance with the manipulation by the manipulation section; a second manipulation member connected to the bending section and arranged in the direction of the longitudinal axis; a connecting section having a first connecting section installed at the first manipulation member and a second connecting section installed at the second manipulation member, and detachably connecting the first manipulation member and the second manipulation member; and a switching mechanism having a first acting section configured to connect the first connecting section and the second connecting section and a second acting section configured to release the first connecting section and the second connecting section from each other, and switching between a connection state in which the first manipulation member and the second manipulation member are connected by the connecting section and a release state in which a connection of the first manipulation member and the second manipulation member is released, in accordance with a relative movement between the elongated member and the insertion section.

Preferably, the connection state and the release state included in the switching mechanism have the following configurations. The connection state is a state in which as a proximal end of the bending section protrudes from the elongated member, the first connecting section and the second connecting section are connected to each other by an action of the first acting section, and the first manipulation member and the second manipulation member freely move in the direction of the longitudinal axis with respect to the direction of the longitudinal axis in accordance with the manipulation by the manipulation section. The release state is a state in which as at least a portion of the bending section is disposed in the inner space of the elongated member, the connection of the first connecting section and the second connecting section is released by an action of the second acting section, and the first manipulation member freely moves in the direction of the longitudinal axis with respect to the second manipulation member and the elongated member in accordance with the manipulation by the manipulation section.

Preferably, the switching mechanism has a protrusion extending in a direction crossing the longitudinal axis of the elongated member and configured to freely protrude from and retract into the insertion section. The first acting section is a restricting surface formed at the elongated member. In the connection state, as the insertion section is disposed at a position at which the proximal end of the bending section protrudes from the elongated member, the protrusion is pressed against the restricting surface, and a state in which the protrusion is pushed into the inner space is maintained. In the release state, as at least a portion of the bending section is disposed in the inner space of the elongated member, the restricting surface and the protrusion are deviated from each other in the direction of the longitudinal axis and the protrusion protrudes from the insertion section.

Preferably, the connecting section is composed of a plunger of a solenoid. The protrusion is connected to an electrical switch. Then, when the protrusion is pushed thereinto, the plunger is actuated to connect the distal end side bending wire and the proximal end side bending wire.

Preferably, the medical instrument system further includes: a pulley to which the connecting section is connected; a break member configured to form a lock state in which the pulley is not capable of moving with respect to a main body of the manipulation section; and a lock lever configured to be manipulated so as to set and release the lock state. Then, the lock lever is manipulated to set the lock state only when the protrusion is pushed thereinto.

Preferably, the medical instrument system further includes: a pulley to which the connecting section is connected; and a bending manipulation section detachably attached to the pulley via an electromagnetic clutch and capable of rotation-manipulating the pulley. The protrusion is connected to an electrical switch. Then, when the protrusion is pushed thereinto, the electromagnetic clutch is actuated to connect the pulley and the bending manipulation section.

DETAILED DESCRIPTION OF THE INVENTION

Figure 1:
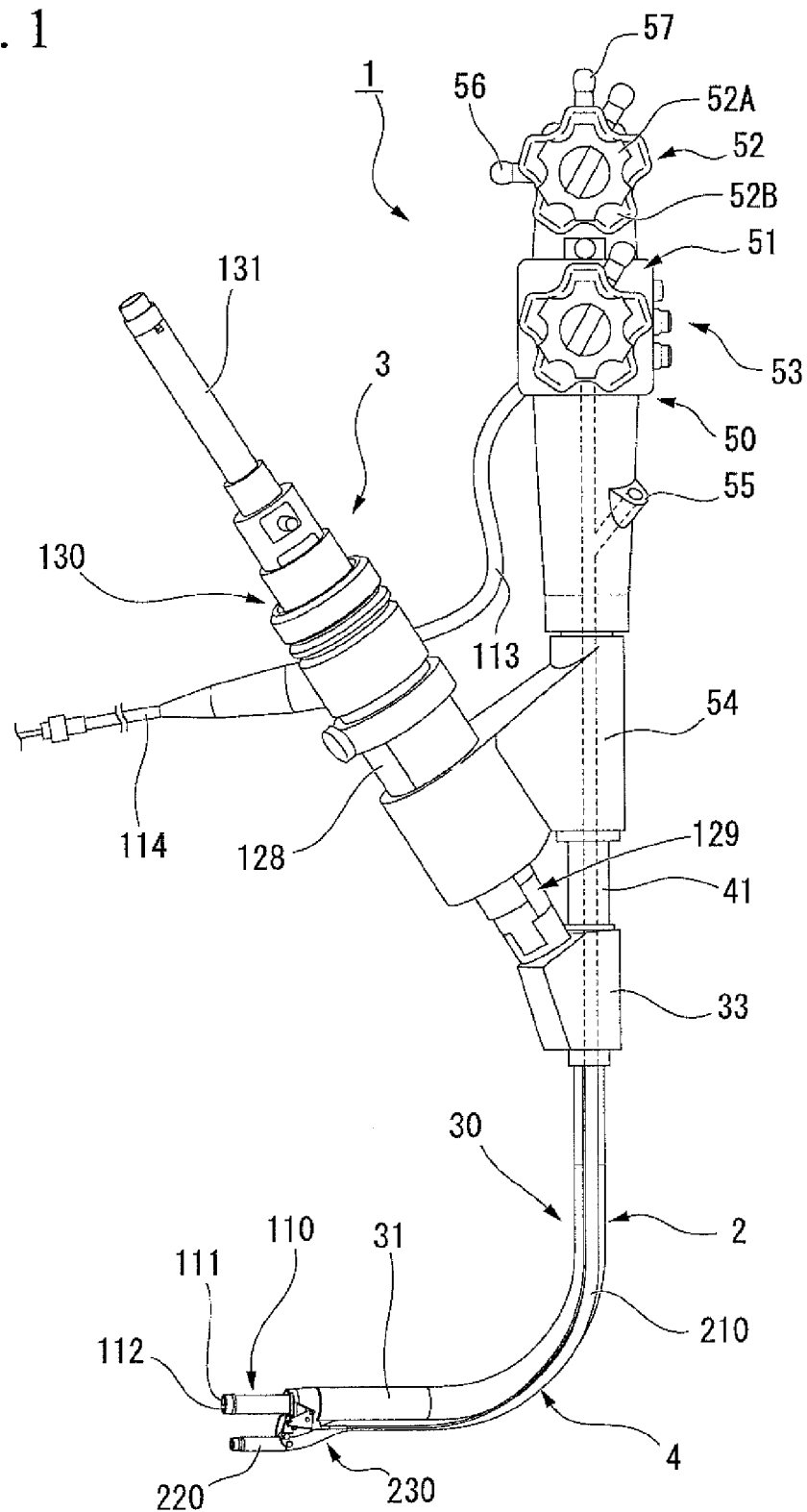
FIG. 1 is an overall view showing an endoscope according to a first embodiment of the present invention.

Hereinafter, an endoscope according to a first embodiment of the present invention will be described with reference to FIGS. 1 to 67. First, the entire configuration and motion during use of an endoscope 1 of the embodiment are described, and then, structures of respective parts configured to enable the motion will be described in detail. In addition, in the following description, like elements, which are already described, are designated by like reference numerals, and overlapping descriptions will not be repeated.

(Entire Configuration)

FIG. 1 is an overall view showing the endoscope 1 according to the embodiment. The endoscope 1 includes an overtube 2 inserted into a body cavity, a right arm section (a first arm section) 3 having an observation unit and inserted into the overtube 2, and a left arm section (a second arm section) 4 disposed along the overtube 2.

The overtube 2 includes a long insertion section (an insertion section A) 30, and a manipulation section (a manipulation section A) 50 configured to manipulate respective parts of the endoscope 1. A bending section (a bending section A) 31 configured to be bent in four directions (hereinafter, referred to as "upward/downward and rightward/leftward directions") spaced from an axis thereof is installed at a distal end side of the insertion section 30. The bending section 31 includes a plurality of bending blocks, and a basic configuration thereof is already known, but a detailed description thereof will be provided.

The manipulation section 50 includes a first dial section 51 configured to manipulate the bending section 31, a second dial section (a manipulation section C) 52 configured to manipulate the left arm section 4, and a button section 53 configured to perform air supply, water supply, suction, and so on, using the right arm section 3. The first dial section 51 is connected to the bending section 31 by a manipulation member such as a wire or the like (not shown), and the bending section 31 can be bent in four directions spaced apart from the axis by manipulating the first dial section 51.

The right arm section 3 includes a long insertion section (an insertion section B) 110, and a manipulation section (a manipulation section B) 130 installed at a proximal end side of the insertion section 110. The insertion section 110 includes a treatment instrument channel 111 into which a treatment instrument is inserted, a known observation unit 112 such as a CCD or the like installed at the distal end section thereof, and an air supply/water supply/suction channel 113 used for air supply, water supply, and suction.

The treatment instrument channel 111 is opened at a distal end of the insertion section 110, passes through the insertion section 110 along the insertion section 110, and extends to a stick 131 of the manipulation section 130.

A video signal obtained by the observation unit 112 is transmitted to a monitor or the like (not shown) by a universal cable 114. The insertion section 110 has a known bending structure formed at the distal end side thereof in which a plurality of bending blocks formed in an annular shape are connected to each other in an axial direction thereof, and can be bent in upward/downward and rightward/leftward directions. The bending structure has an active bending section (a bending section B) that is disposed near the distal end side thereof and that can be manipulated by the manipulation section 130, and a passive bending section disposed nearer the proximal end side than the active bending section. The bending structure is described later in detail. The active bending section can be bent in a desired direction by swing-manipulating the manipulation section 130. A known corrugated tube 129 is connected to a proximal end side of the passive bending section 116 to form the proximal end side of the insertion section 110.

The air supply/water supply/suction channel 113 is opened at the distal end of the insertion section 110, passes through the insertion section 110 to extend to the proximal end side, exits from the manipulation section 130 and enters the manipulation section 50 of the overtube 2 to pass through the button section 53, exits from the manipulation section 50 to return into the manipulation section 130, and extends into the universal cable 114 to be connected to a suction apparatus and a fluid supply source (not shown). In the air supply/water supply/suction channel, a valve (not shown) configured to switch ON/OFF of various motions via the air supply/water supply/suction channel 113 is installed in the manipulation section 50. The air supply/water supply/suction channel 113 can perform switching of air supply, water supply, suction, and being in OFF states by manipulating the above-mentioned button section 53. Instead of disposing a portion of the air supply/water supply/suction channel 113 in the manipulation section 50, an electromagnetic valve may be installed at a portion of the air supply/water supply/suction channel 113 such that the electromagnetic valve can be remotely manipulated by the button section 53.

Figure 2:
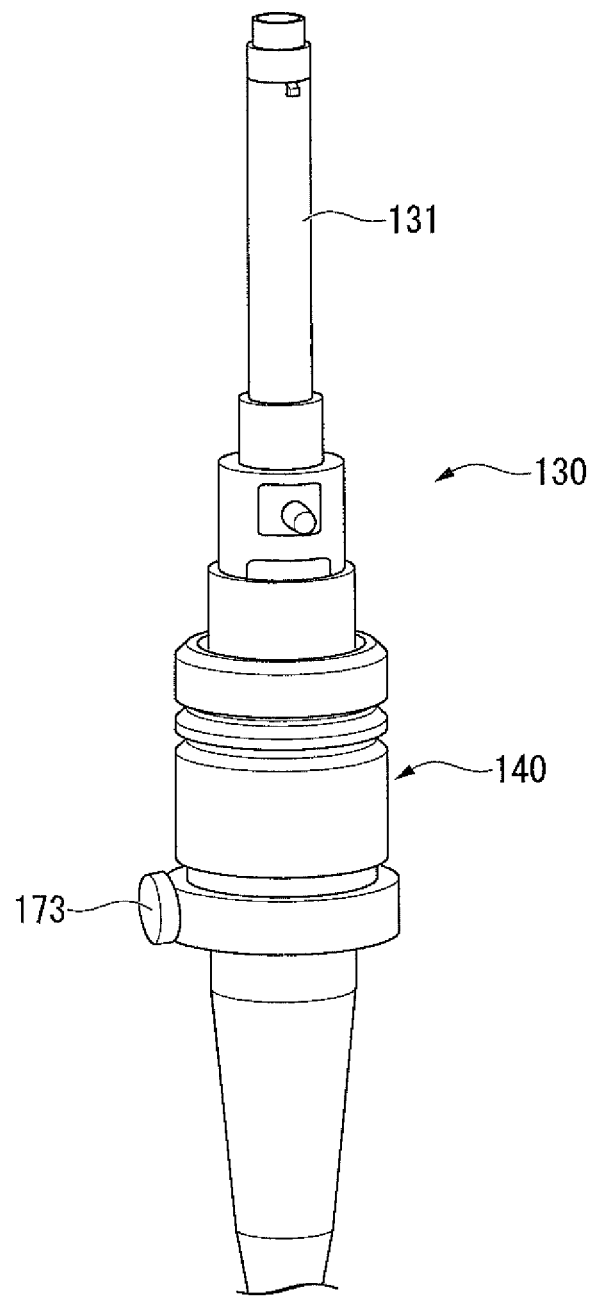
FIG. 2 is an enlarged view showing a manipulation section of a right arm section of the endoscope according to the first embodiment of the present invention.

FIG. 2 is an enlarged view showing the manipulation section 130 of the right arm section 3. The manipulation section 130 includes a tubular stick (a joy stick) 131 swingable in upward/downward and rightward/leftward directions, and a swing mechanism 140 configured to swingably support the stick 131. The treatment instrument channel 111 passes through an inner cavity of the stick 131. By inserting various treatment instruments for endoscopes into the treatment instrument channel 111 from a proximal end side of the stick 131, a distal end of the treatment instruments can protrude from the distal end of the treatment instrument channel 111. In addition, a protrusion length of the treatment instrument can be adjusted by advancing or retracting treatment instrument with respect to the right arm section 3. A specific structure of the treatment instrument that can be appropriately used in the endoscope of the embodiment is described later.

A plurality of manipulation members such as wires or the like (not shown) connected to the active bending section are connected to the swing mechanism 140. The manipulation members can be respectively pushed and pulled to bend the active bending section in a desired direction by pulling the stick 131 down in upward/downward and rightward/leftward directions. A specific structure of the swing mechanism 140 is described later.

Figure 3:
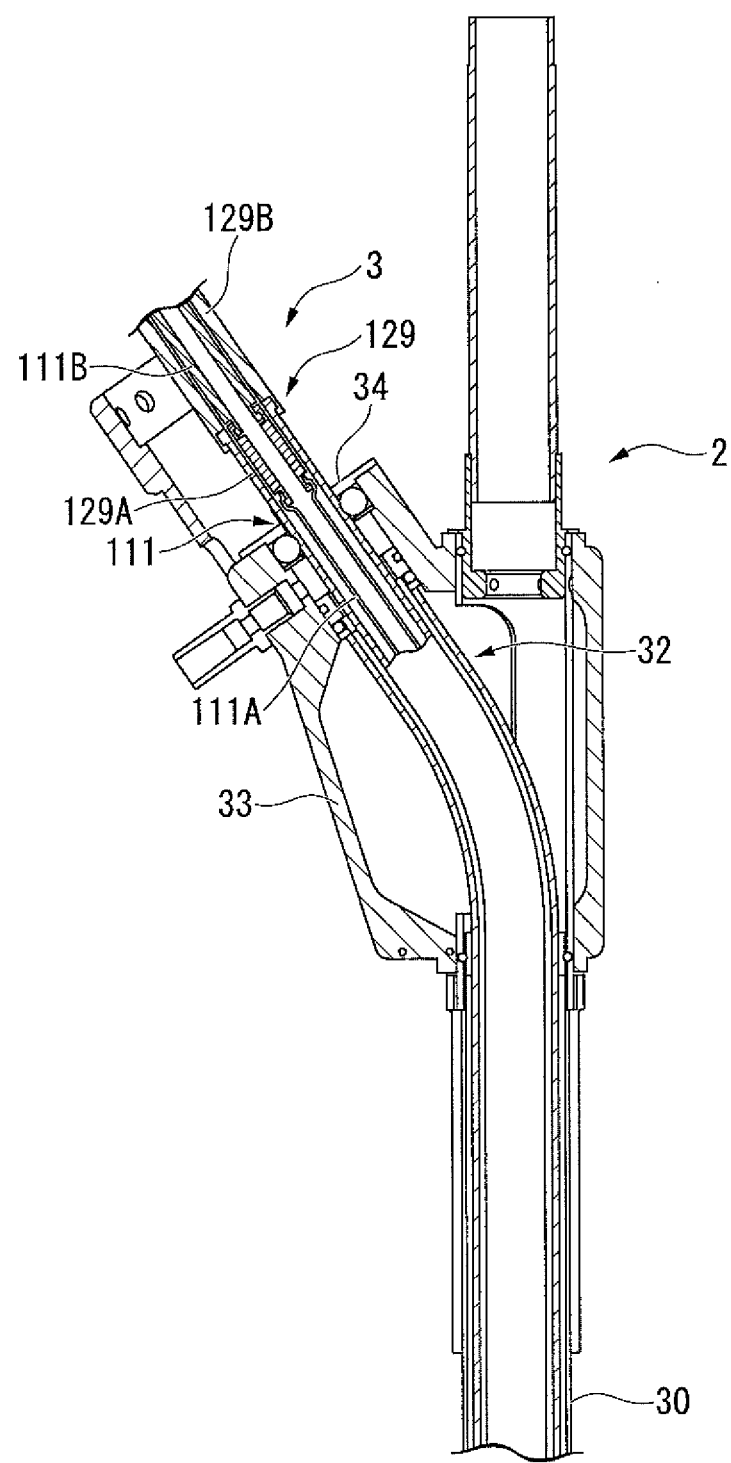
FIG. 3 is a cross-sectional view showing a branch member and a periphery thereof of the endoscope according to the first embodiment of the present invention.

As shown in FIG. 3, the right arm section 3 is inserted into the inner cavity of the insertion section 30 from an opening 32 formed in an outer circumferential surface of the insertion section 30 of the overtube 2. The opening 32 is covered by a branch member 33 attached to the insertion section 30 to be rotatable about an axis of the insertion section 30. The right arm section 3 is inserted into the opening 32 from an insertion hole 34 formed at a proximal end side of the branch member 33.

The proximal end side of the insertion section 110 protruding from the insertion hole 34 extends in a direction spaced apart from the insertion section 30 of the overtube 2. As shown in FIG. 1, the proximal end of the insertion section 110 is supported by a holder 54 rotatably attached to the manipulation section 50, and is held in a position in which the manipulation section 50 and the manipulation section 130 can be appropriately manipulated by one user. In addition, as the holder 54 is rotated with respect to the manipulation section 50, the positional relation between the manipulation section 50 and the manipulation section 130 can be adjusted to a position at which the operator can easily manipulate the sections 50 and 130.

The right arm section 3 can advance and retract with respect to the overtube 2. The right arm section 3 can be manipulated by moving the manipulation section 130 to advance and retract along the axis with respect to the holder 54. In addition, the positional relation between the right arm section 3 and the overtube 2 can be held by a stopper 128 having a flat spring (not shown). Accordingly, the protrusion length of the right arm section 3 from the overtube 2 can be maintained constant.

The corrugated tube 129 of the insertion section 110 is divided in the proximal end section, and a distal end side corrugated tube 129A (a first hose) and a proximal end side corrugated tube 129B (a second hose) are connected to each other to enable relative rotation. Accordingly, fine adjustment between the manipulation section 130 and a bending direction of the active bending section is possible, and a manipulation feeling can be improved. That is, a manipulation direction (upward/downward and rightward/leftward directions) of the stick 131 can be adjusted such that the operator can easily perform the manipulation. When fine adjustment of the corrugated tube 129 is performed or the fine adjustment is performed by rotating the holder 54, torsion may be accumulated on the treatment instrument channel 111. For this reason, as shown in FIG. 3, the treatment instrument channel 111 has a distal end side region 111A (a first channel) and a proximal end side region 111B (a second channel) disposed near a connection portion of the corrugated tube 129 and connected to each other to enable relative rotation.

As shown in FIG. 1, the left arm section 4 includes a long channel section 210, a bending section (a bending section C) 220 formed at the distal end of the channel section 210, and a bending displacement section 230 configured to displace the bending section 220 at an appropriate position with respect to the right arm section 3 protruding from the overtube 2.

The channel section 210 is a tubular member having an inner cavity (a channel), and disposed along the insertion section 30 of the overtube 2. The proximal end side of the channel section 210 enters the inner cavity of the insertion section 30 from the distal end side of the branch member 33 via the opening 32, and is disposed not to interfere with manipulation of the operator. A forceps hole 55 in communication with the channel section 210 is formed in the manipulation section 50 of the overtube 2. The appropriately selected treatment instrument can be inserted into the channel section 210 from the forceps hole 55 and protrude from the distal end of the bending section 220.

The bending section 220 has a known configuration in which a plurality of annular bending blocks are connected to each other in an axial direction thereof, and can be bent in upward/downward and rightward/leftward directions. The inner cavity of the bending section 220 is in communication with a channel of the channel section 210. A manipulation member (not shown) configured to bend the bending section 220 is fixed to the bending block having a distal end nearest the distal end side of the bending section 220, passes through a wire guide (not shown) formed at each of the bending blocks, further passes the channel section 210 to extend to the manipulation section 50, and is connected to the second dial section 52. Accordingly, the bending section 220 can be bent in a desired direction by manipulating the second dial section 52.

Figure 4:
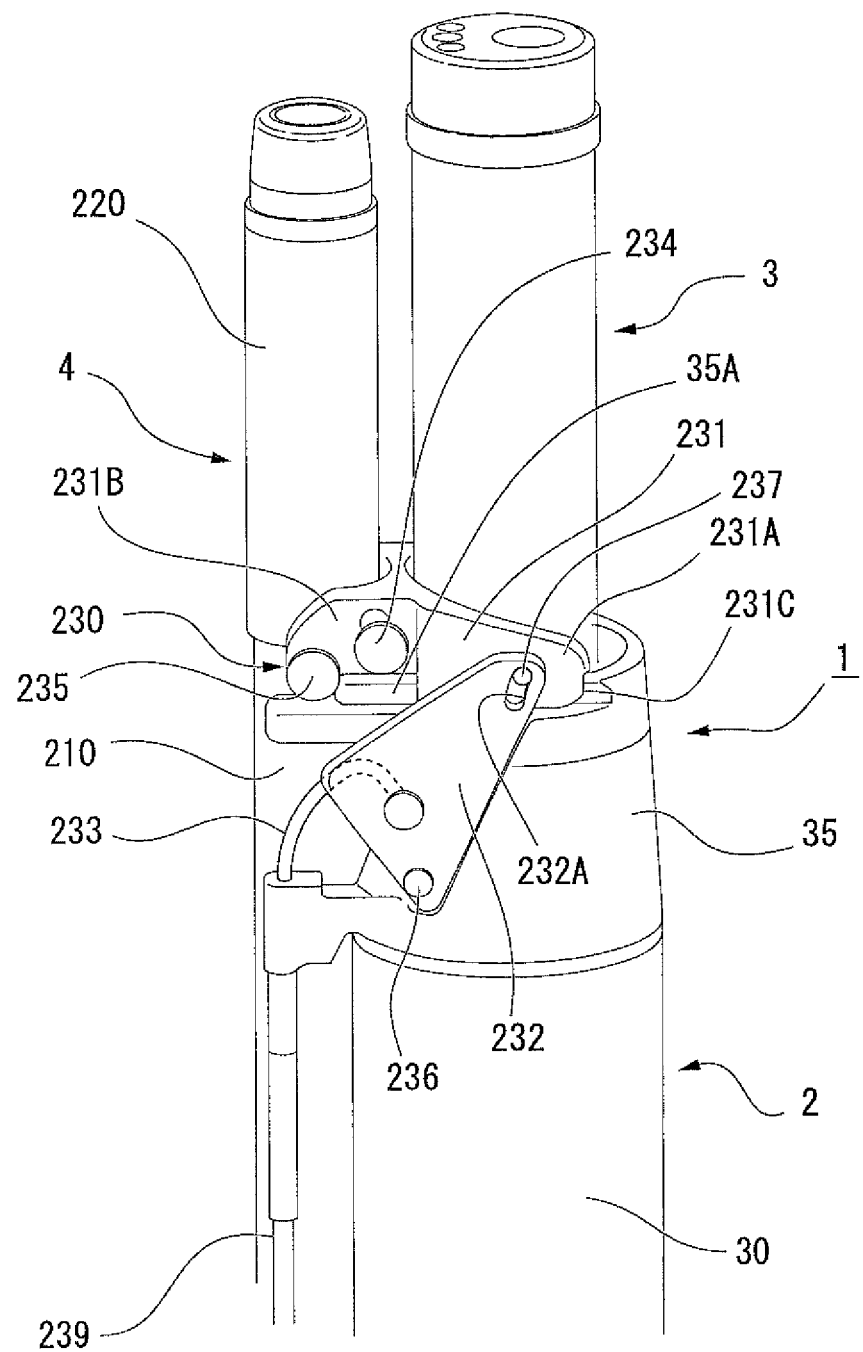
FIG. 4 is an enlarged view showing a distal end side of the endoscope according to the first embodiment of the present invention.

As enlarged and shown in FIG. 4, the bending displacement section 230 includes a displacement member 231 slidably supported by the distal end section of the overtube 2, a rotating member 232 connected to the displacement member 231 and rotatably supported by the distal end section of the overtube 2, and a towing member 233 configured to manipulate the rotating member 232.

The displacement member 231 includes a U-shaped outer fitting section 231A, and a U-shaped support section 231B opened at an opposite side of the outer fitting section 231A. A boundary area between the bending section 220 and the channel section 210 is fixed along an inner surface of the support section 231B by screws 234 and 235. A groove 231C is formed in a lower surface of the displacement member 231 in contact with a cap 35 attached to the distal end of the overtube 2. The displacement member 231 can slide in a direction perpendicular to the axis of the insertion section 30, as the groove 231C is engaged with a rail 35A formed on the cap 35.

The rotating member 232 is supported by a rotating shaft 236 attached to the proximal end side of the cap 35, and can rotate about the rotating shaft 236 within a predetermined range. The rotating member 232 has a long hole 232A. The long hole 232A is engaged with a pin 237 protruding to an outer circumferential surface of the outer fitting section 231A.

A wire or the like can be used as the towing member 233. The distal end section of the towing member 233 is connected to the rotating member 232. The proximal end side of the towing member 233 is inserted into a coil sheath 239 disposed along the insertion section 30. The coil sheath 239 and the towing member 233 enter the inner cavity of the insertion section 30 from the distal end side of the branch member 33, similar to the channel section 210. The proximal end section of the towing member 233 is connected to the second dial section 52.

Figure 5:
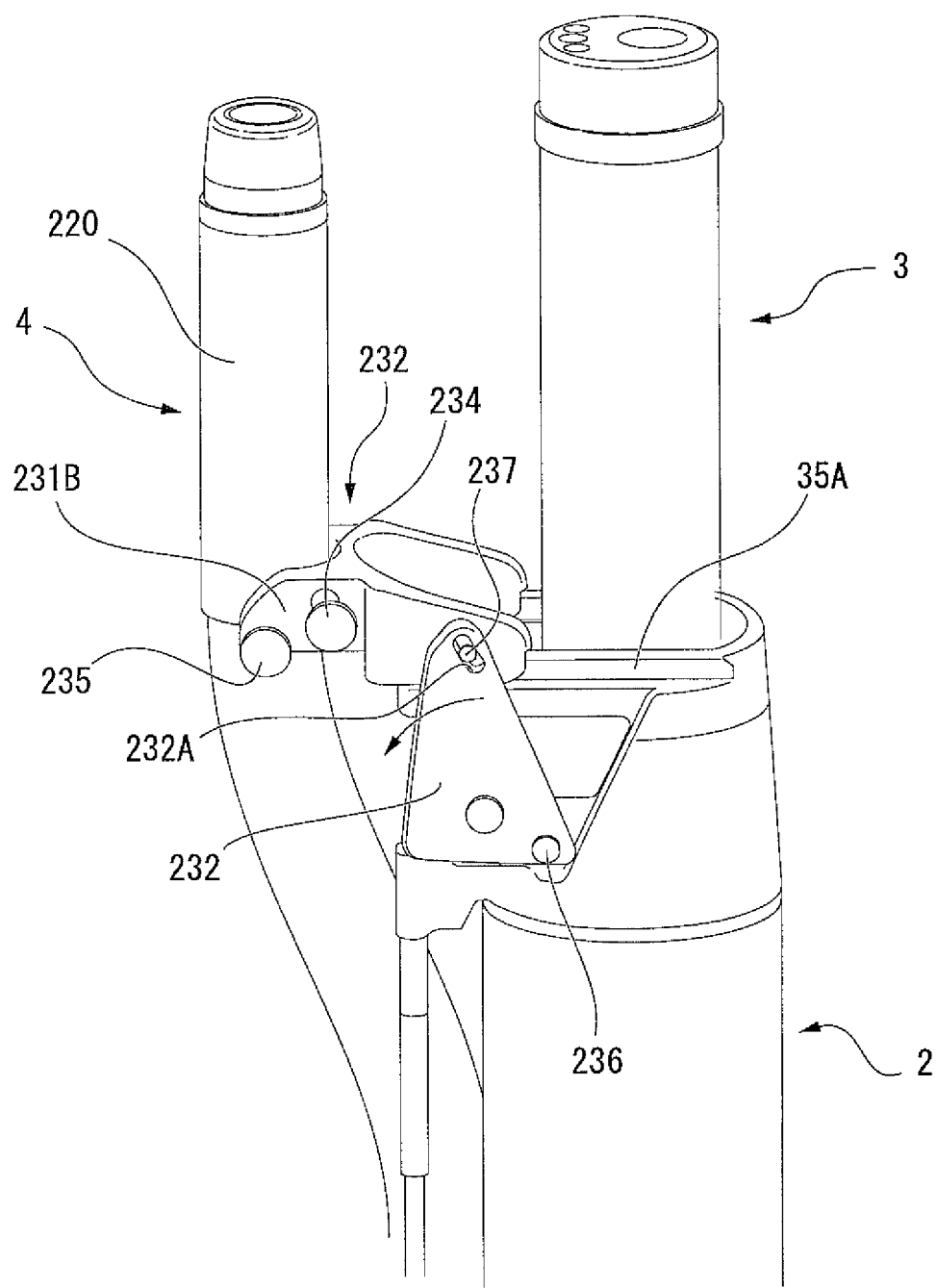
FIG. 5 is an enlarged view showing the distal end side of the endoscope according to the first embodiment of the present invention.

According to the above-mentioned configuration, when the second dial section 52 is manipulated to tow the towing member 233 to a hand side (toward the manipulation section 50), as shown in FIG. 5, the rotating member 232 rotates about the rotating shaft 236. Then, the pin 237 moves through the long hole 232A, and the rotating member 232 moves along the rail 35A in a direction spaced apart from the overtube 2. As a result, the bending section 220 is spaced a predetermined distance from the overtube 2, and the left arm section 4 and the right arm section 3 protruding from the overtube 2 are in a certain position (triangulation as described below) in which treatment by the treatment instrument protruding from the distal end opening thereof can be appropriately performed. A lock mechanism is installed at the second dial section 52. The towing member 233 can hold the towed state by the lock mechanism. The lock mechanism can be appropriately selected from known various configurations, and a specific structure thereof is described later as an example.

Figure 6:
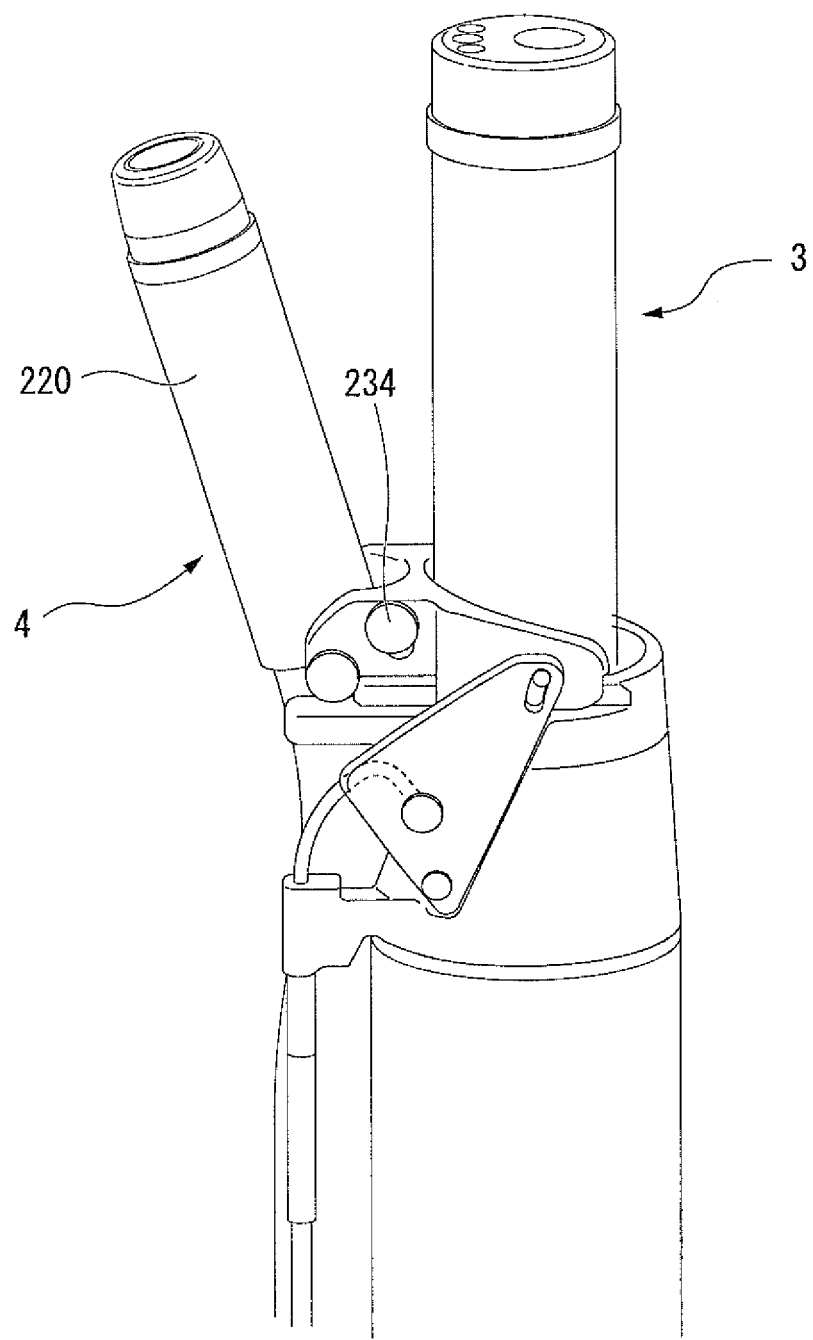
FIG. 6 is an enlarged view showing the distal end side of the endoscope according to the first embodiment of the present invention.

In the support section 231B, since the screw hole into which the one screw 234 is inserted is a long hole, as an insertion position of the screw 234 in the screw hole is adjusted, as shown in FIG. 6, the direction of the bending section 220 can be varied by a predetermined angle, for example, 15 degrees, and the distance between the distal end openings through which the treatment instruments protrude can be further increased within a predetermined range.

Figure 7:
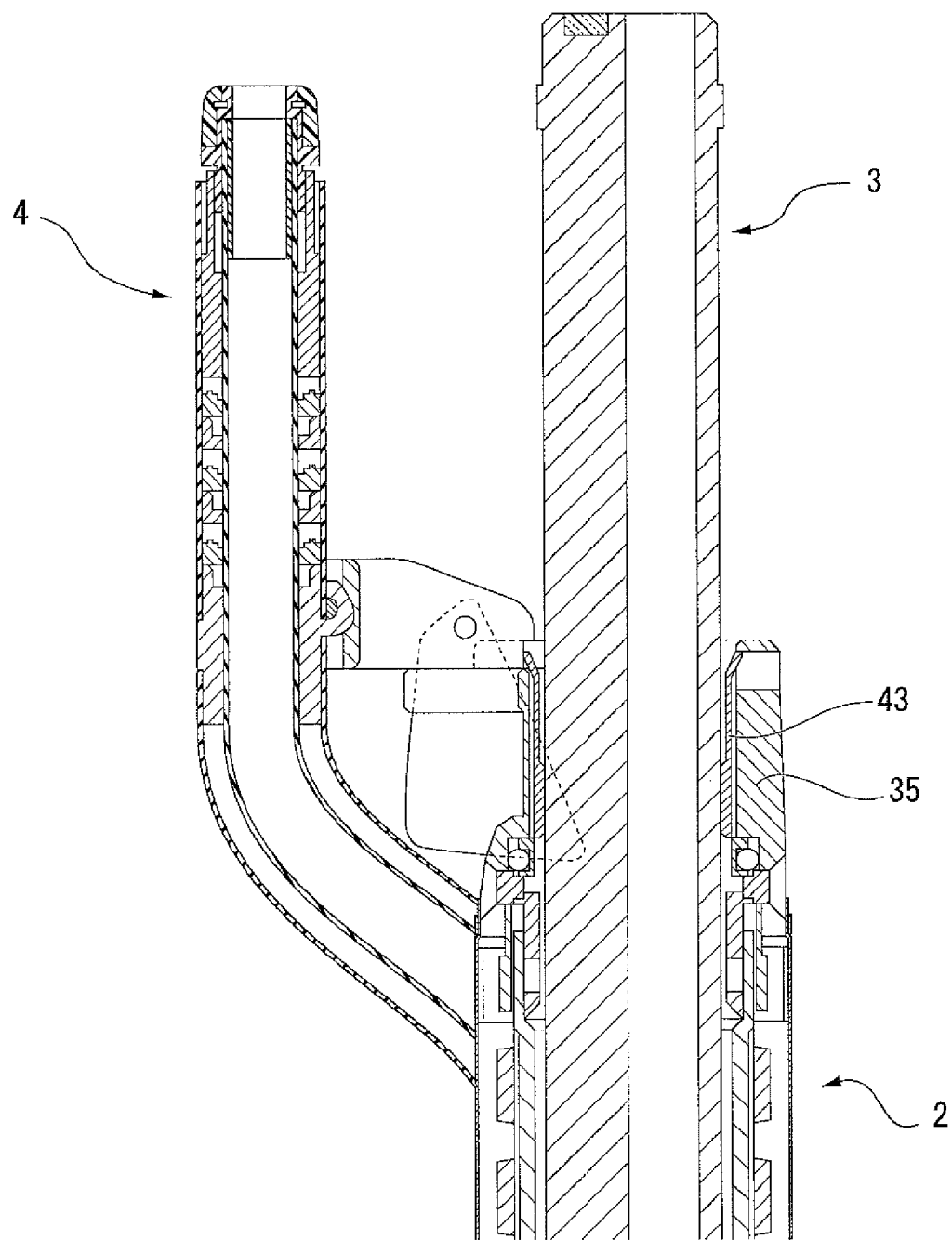
FIG. 7 is an enlarged cross-sectional view showing the distal end side of the endoscope according to the first embodiment of the present invention.

As shown in a cross-sectional view of FIG. 7, a tubular spacer 43 is attached to the inner cavity of the cap 35 of the distal end of the overtube 2. Rattling of the right arm section 3 upon advancing and retracting manipulation can be reduced by the spacer 43.

(Basic Motion in Use)

In the motion in use of the endoscope 1 as configured above, the case in which a portion of the stomach is excised as a target tissue is described as an example.

Before insertion of the distal end section of the endoscope 1 into the body cavity of the patient, the operator makes the bending section 220 of the left arm section 4 into a linear state, and actuation of the bending displacement section 230 is released so that the left arm section 4 is in a state near the overtube 2. In addition, the right arm section 3 is inserted into the opening of the branch member 33, and the distal end thereof protrudes from the distal end of the overtube 2.

Next, the operator inserts the distal end section of the endoscope 1 into the body cavity of the patient. Various natural openings formed in a human body such as the mouth, the anus, the vagina, or the like, can be appropriately selected as an access path. In the description, since the stomach is a target tissue, insertion is performed from the mouth.

Figure 8:
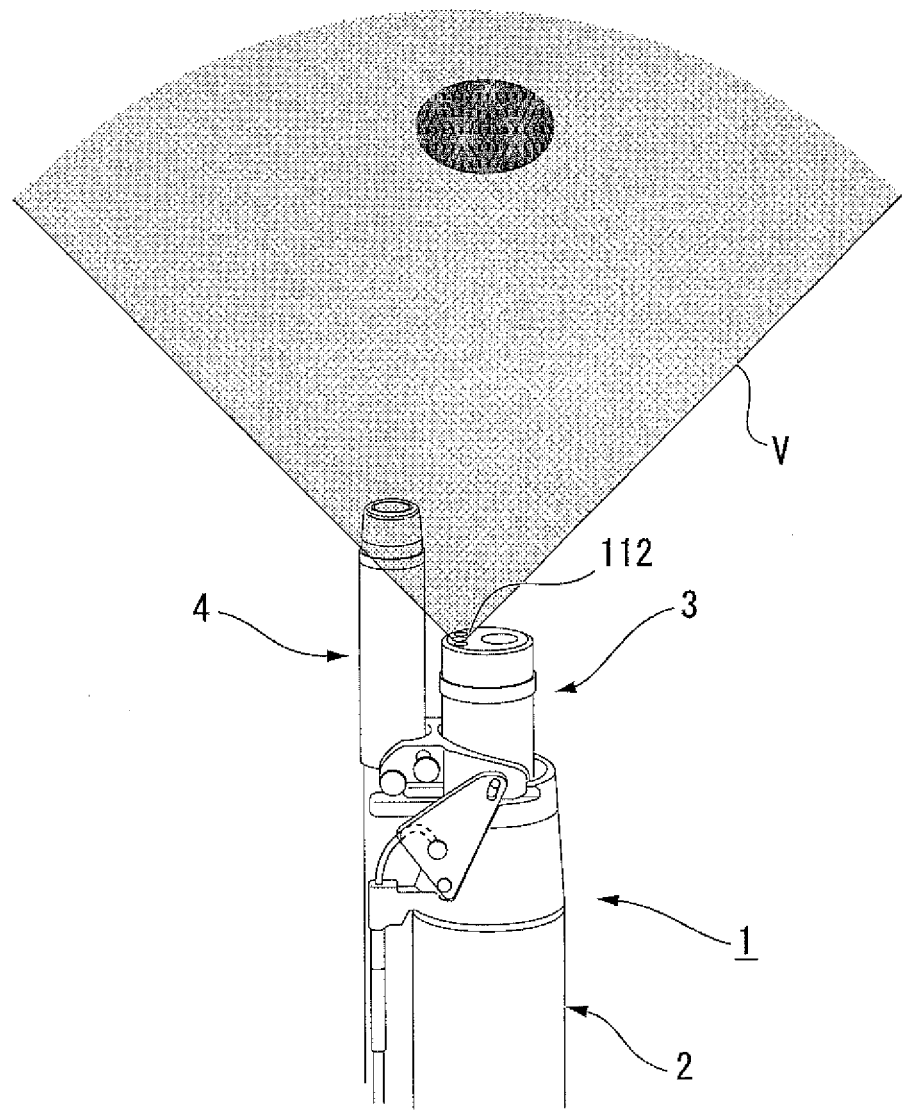
FIG. 8 is a view showing a positional relation of respective parts in use of the endoscope according to the first embodiment of the present invention.

Upon insertion of the distal end section of the endoscope 1 to the vicinity of the target tissue, as shown in FIG. 8, the operator may adjust a protrusion length of the right arm section 3 from the overtube 2 such that the left arm section 4 in the linear state can be checked in the front as possible within a range of a visual field V of the observation unit 112. Since the distal end of the left arm section 4 protrudes forward more than the distal end of the overtube 2, the distal end of the left arm section 4 can be smoothly inserted while the operator surely observes the distal end of the left arm section 4.

When the distal end section of the endoscope 1 arrives at the vicinity of the target tissue, the operator inserts the treatment instrument into the treatment instrument channel 111 from the proximal end side of the manipulation section 130, and makes the treatment instrument protrude from the distal end of the right arm section 3. In addition, another treatment instrument is inserted into the channel section 210 from the forceps hole 55 to protrude from the distal end of the left arm section 4. Further, a lever of the second dial section 52 is manipulated to move the bending displacement section 230, and the bending section 220 is spaced apart from the overtube 2.

As an example, in consideration of an object for excising a portion of the stomach, a known knife configured to perform dissection of the tissue is inserted into the right arm section 3, and a known grasping forceps configured to hold a portion of the tissue to be dissected is inserted into the left arm section 4.

Figure 9:
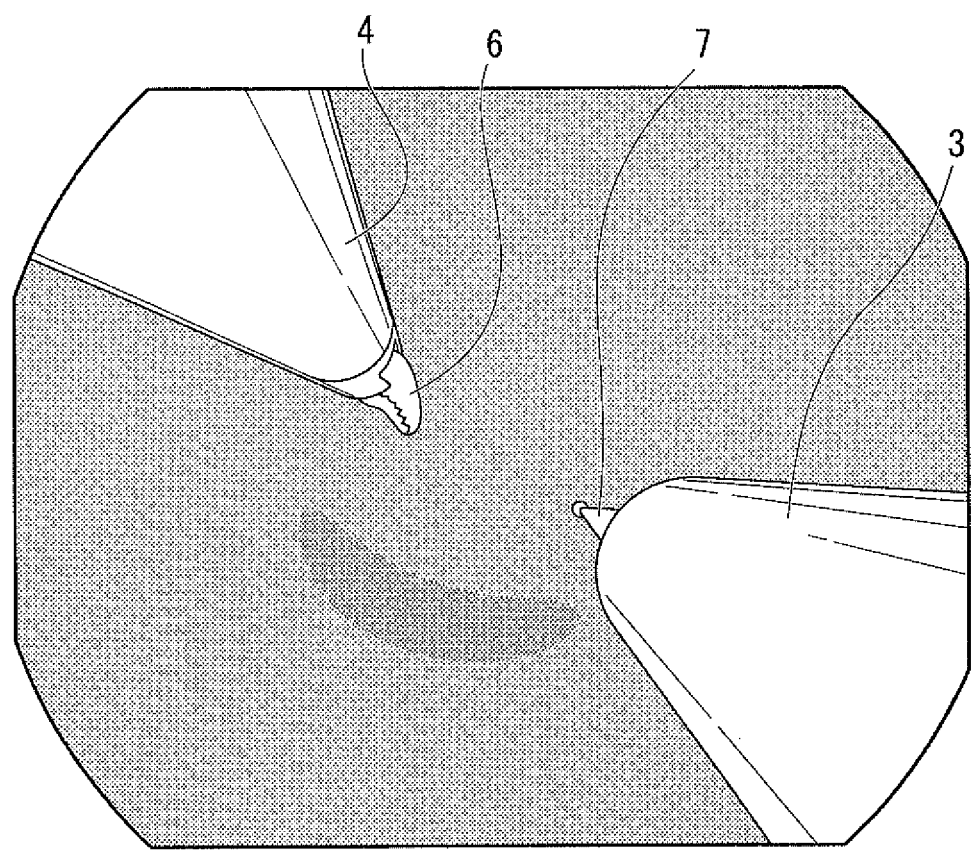
FIG. 9 is a view showing an example of a video of an observation unit of the right arm section of the endoscope according to the first embodiment of the present invention.

FIG. 9 shows an example of a video of the observation unit 112 after actuation of the bending displacement section 230. A grasping forceps 6 inserted into the left arm section 4 and a knife 7 inserted into the right arm section 3 protrude from left and right sides of a visual field, respectively, toward substantially the same position in the vicinity of a center of a rear side of the visual field. For this reason, an appropriate procedure can be performed in the vicinity of the center of the visual field of the observation unit using the grasping forceps 6 and the knife 7. The positional relation of the left arm section 4 and the right arm section 3 that enables such a motion is referred to as triangulation in the embodiment.

Figure 10:
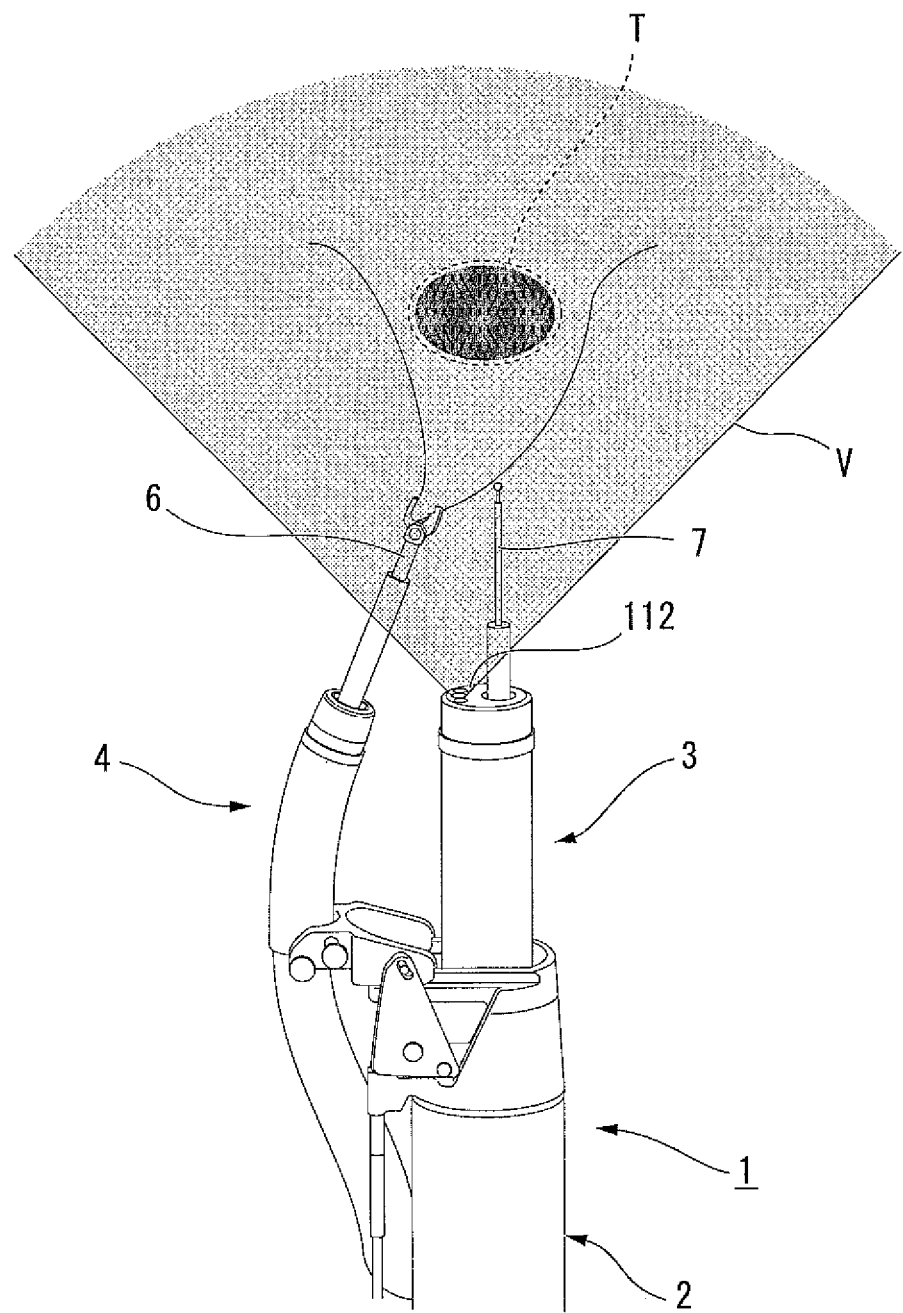
FIG. 10 is a view showing a positional relation of respective parts in use of the endoscope according to the first embodiment of the present invention.
Figure 11:
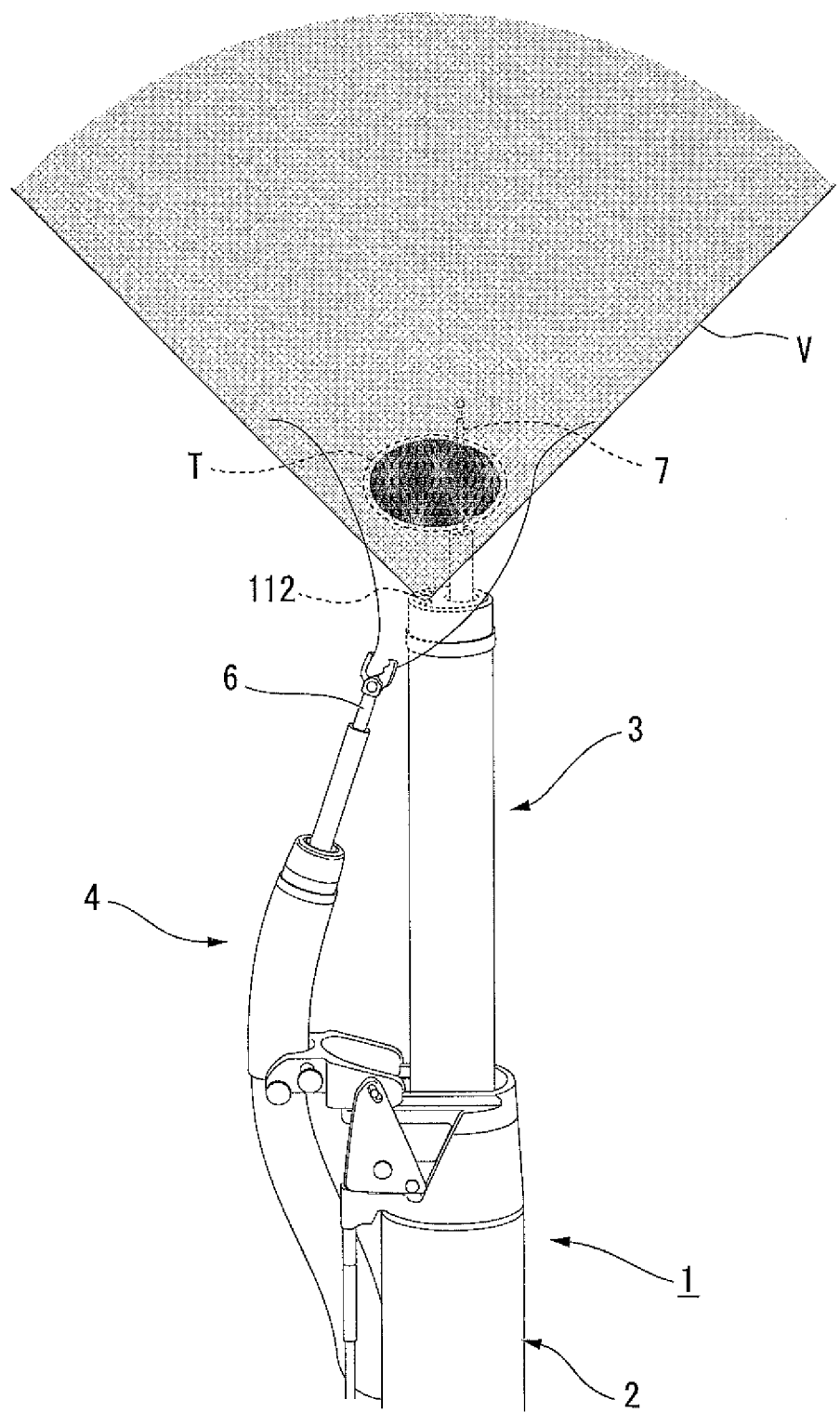
FIG. 11 is a view showing a positional relation of respective parts in use of the endoscope according to the first embodiment of the present invention.

The operator manipulates the grasping forceps 6 to grip a portion of a target tissue T and moves the right arm section 3 forward, to accomplish the positional relation as shown in FIG. 10. Then, the manipulation section 130 is manipulated to dissect (ablate) the target tissue T using the knife 7. Here, when the positional relation is set such that the left arm section 4 protrudes upward to a relatively upside position (for example, a direction of 10 o'clock or the like) in the video of the observation unit 112, the target tissue T gripped by the grasping forceps 6 is raised, and the knife 7 is easily inserted thereunder. A protrusion position of the left arm section 4 in the video can be adjusted by rotating the insertion section 110 of the right arm section 3 with respect to the overtube 2. The operator performs dissection of the target tissue T, moves the right arm section 3 to further advance as shown in FIG. 11 as necessary, and dissects a portion of a rear side of the target tissue T. As the right arm section 3 is moved forward, the procedure can be performed while the distance between an area to be dissected and the observation unit 112 is appropriately maintained.

Figure 12:
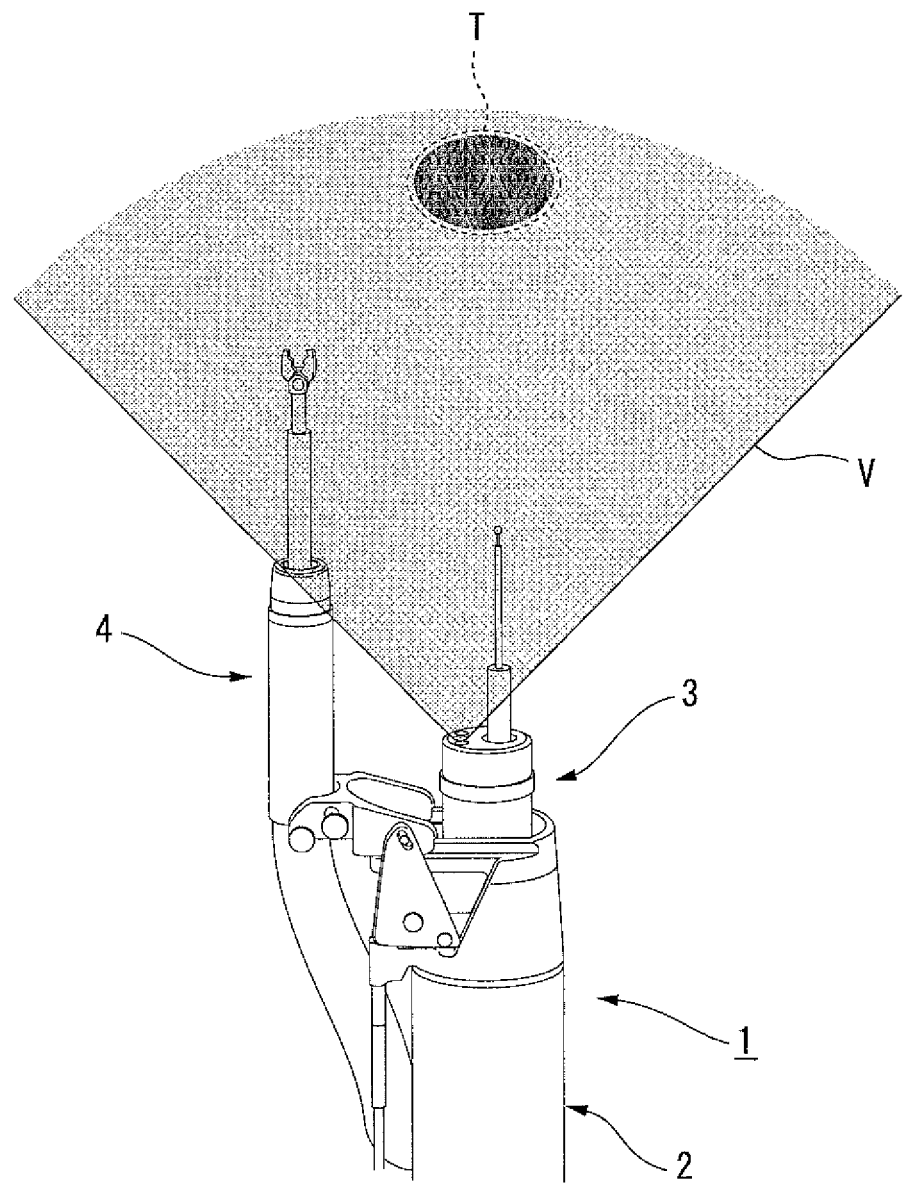
FIG. 12 is a view showing a positional relation of respective parts in use of the endoscope according to the first embodiment of the present invention.
Figure 13:
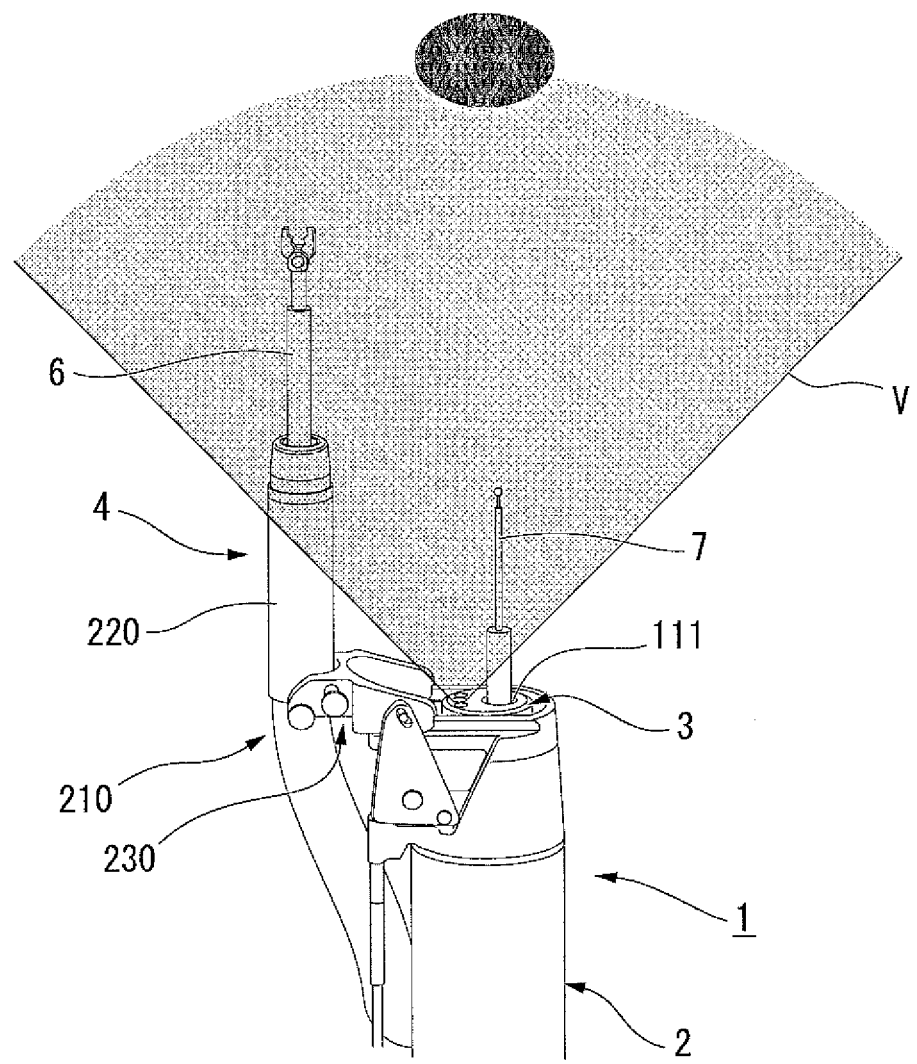
FIG. 13 is a view showing a positional relation of respective parts in use of the endoscope according to the first embodiment of the present invention.

When the right arm section 3 moves forward, since the observation unit 112 also moves forward, as shown in FIG. 11, the left arm section 4 or the grasping forceps 6 may be deviated from the visual field V of the observation unit 112 to be disappeared or only a portion of the target tissue T may be observed, so that a progress status of the procedure may not be recognized. In this case, the operator may move the right arm section 3 rearward as shown in FIG. 12 to be in a position in which the entire target tissue T can be overlooked, or may move the right arm section 3 rearward to a position at which the left arm section 4 and a bending state thereof are recognized in the visual field V, regardless of a direction of the bending section 220, as shown in FIG. 13. As a result, the progress of the procedure or the surroundings can be accurately understood, and the time required for the entire procedure can be reduced.

When the predetermined procedure is completed, the operator releases the actuation state of the bending displacement section 230, and receives the grasping forceps 6 in the channel section 210 or removes the grasping forceps 6 from the left arm section 4. Further, the knife 7 is also accommodated in the treatment instrument channel 111, or is removed from the right arm section 3. The operator removes the endoscope 1 from the patient in this state to complete a series of procedures.

In the conventional procedure using the treatment instrument inserted into the endoscope and the channel, the distal end section of the endoscope is largely bent, and the procedure is performed in a state in which the distal end opening and the observation unit are directed to the manipulation section side. Here, in order to move the endoscope away from the target tissue, it is needed to move the insertion section of the endoscope forward. However, since a direction in the endoscope image is different from the manipulation direction of the hand, skillfulness is required for the manipulation.

According to the endoscope 1 of the embodiment, since the right arm section 3 having the observation unit 112 is inserted into the overtube 2 and used, even when the procedure is performed under the above-mentioned circumstance, the right arm section 3 can be surely spaced apart from the target tissue through an intuitive manipulation in which the right arm section 3 is retracted. Accordingly, even in the case of the operator having little experience, the procedure can be easily performed.

Next, the respective configurations of the treatment instrument appropriately applied to the overtube 2, the right atm section 3, and the endoscope 1 will be described in detail below.

(Overtube)

Figure 14:
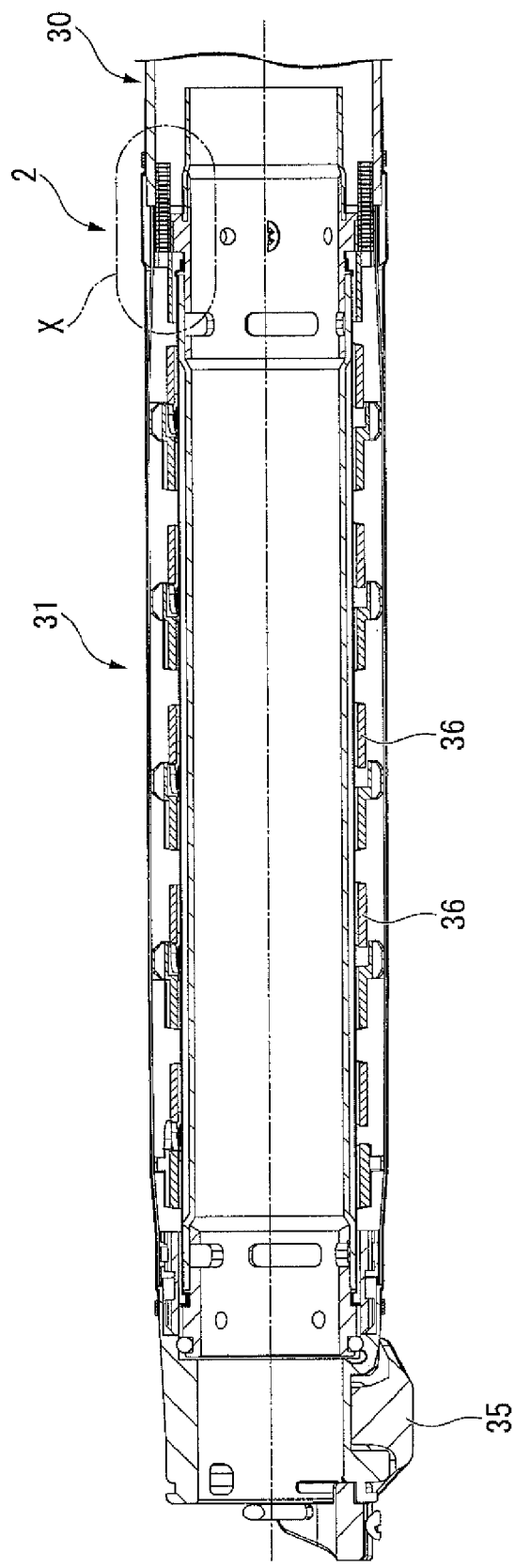
FIG. 14 is a cross-sectional view showing a bending section of an overtube of the endoscope according to the first embodiment of the present invention.

FIG. 14 is a cross-sectional view showing the bending section 31 of the overtube 2. As shown in FIG. 14, the bending section 31 has a known basic configuration in which a plurality of annular bending blocks 36 are parallelly connected to each other in the axial direction. Since connecting sections of the neighboring bending blocks 36 are deviated by a phase of 90 degrees in a circumferential direction of the bending blocks 36, the bending blocks 36 can be bent in two directions perpendicular to each other, and the bending section 31 can be bent in the upward/downward and rightward/leftward directions as a whole. The bending blocks 36 is formed of a stainless steel having a relatively high stiffness, for example, SUS420J2 in Japanese Industrial Standards (JIS), and has a sufficient strength for preventing the bending blocks 36 from being plastically deformed upon bending even when the thickness thereof is about 0.5 mm.

Figure 15:
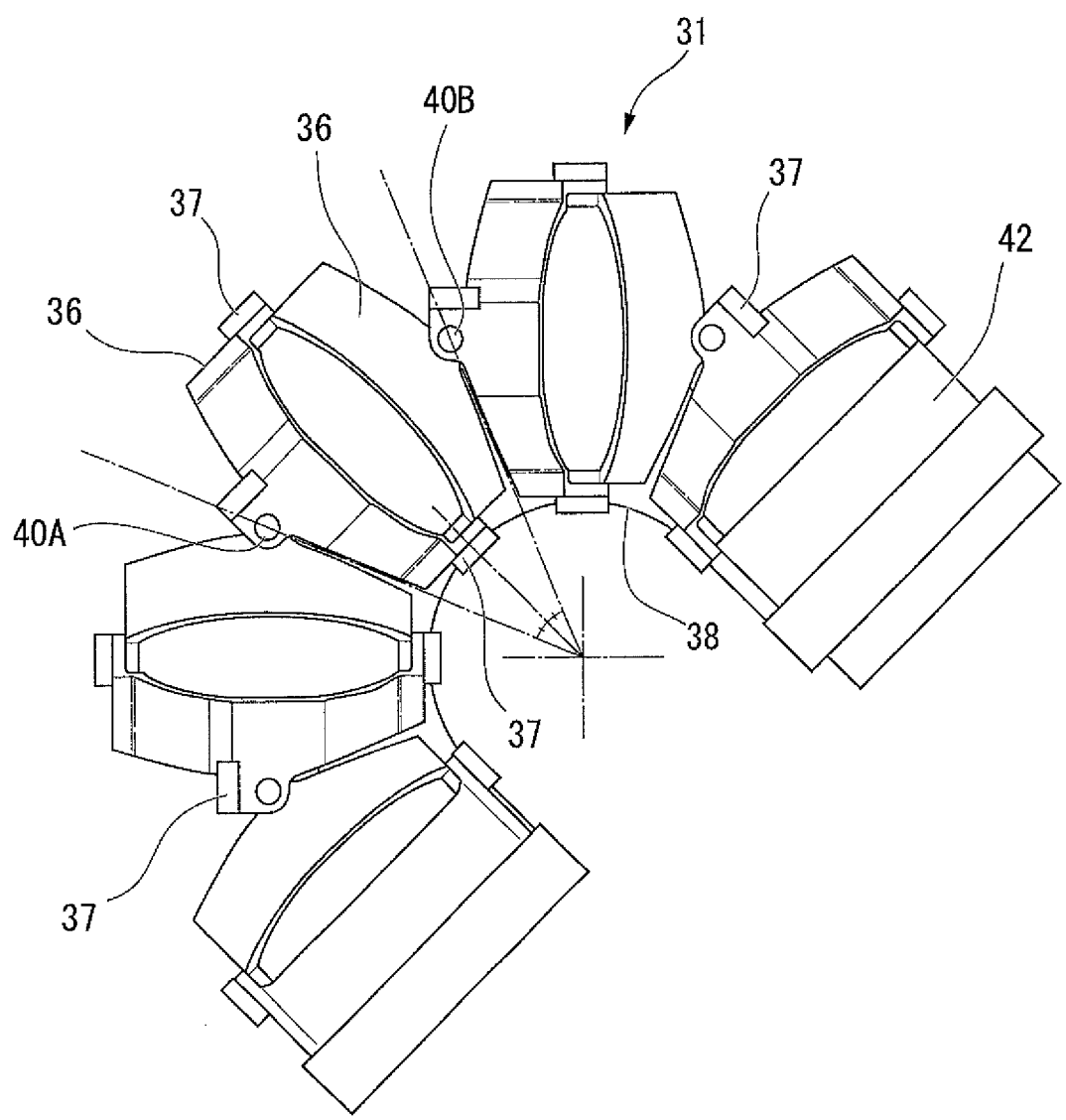
FIG. 15 is a view showing a bending block of the bending section of the endoscope according to the first embodiment of the present invention.

As shown in FIG. 15, shapes of the outer circumferential surfaces of the respective bending blocks 36 are not uniform in the circumferential direction, and as a result, the bending blocks 36 can be most strongly bent in one direction of upward/downward and rightward/leftward directions. The right arm section 3 is inserted into the overtube 2 such that one direction of an initial (default) video of the observation unit 112 is directed upward.

Figure 16:
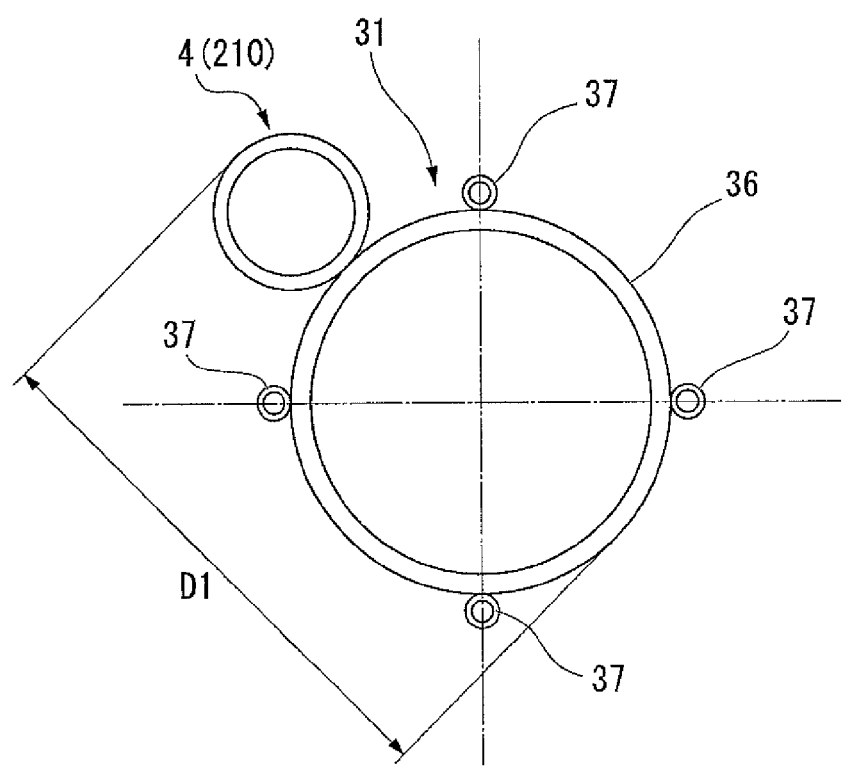
FIG. 16 is a view showing a positional relation between the bending block and a left arm section of the bending section of the endoscope according to the first embodiment of the present invention.

As shown in FIG. 16, four guides 37 into which the manipulation members are inserted, are formed at the outer circumferential surfaces of the bending blocks 36 with 90-degree phase intervals. Accordingly, the inner cavities of the bending blocks 36 can be effectively used. The right arm section having a larger diameter can be inserted into the bending blocks. The outer diameter of the bending blocks can be further reduced while the maximum diameter of the right arm section which can be inserted into the bending blocks is maintained. In addition, the channel section 210 of the left arm section 4 is disposed along the bending section 31 at a position at which the guide 37 is not formed. Accordingly, a maximum dimension D1 in the radial direction of the distal end side of the endoscope 1 can be reduced, and the endoscope 1 can be miniaturized as a whole.

As shown in FIG. 15, formation positions of the guides 37 of the bending blocks 36 in the axial direction are disposed back and forth in the axial direction of the guide, and are set to positions equidistant from two connecting sections 40A and 40B bent according to towing of a manipulation member 38 inserted into the guide. For this reason, when the manipulation member 38 is towed, the guide 37 can be disposed at a place at which the manipulation member 38 between the connecting sections 40A and 40B approaches the bending blocks 36 most, and interference of the guide 37 with respect to advancing and retracting of the manipulation member 38 can be reduced.

Figure 17:
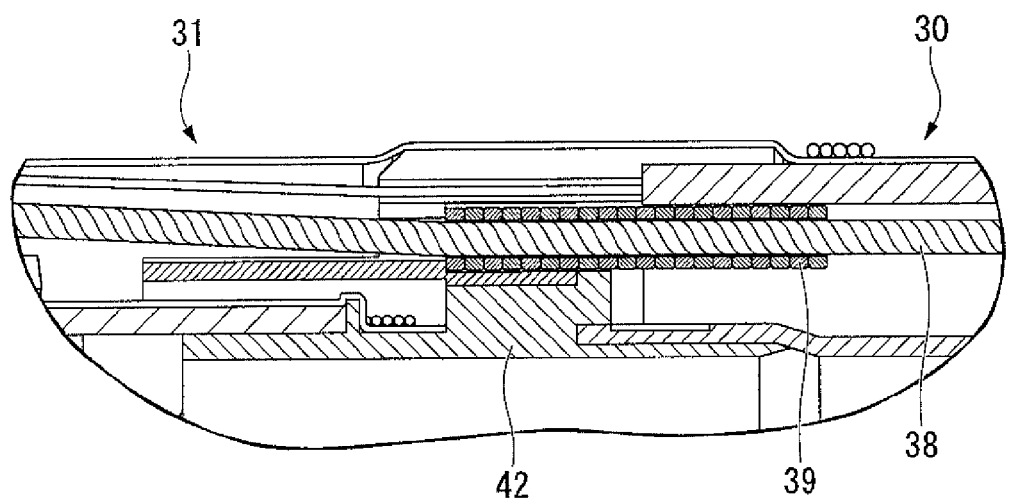
FIG. 17 is an enlarged view of a range X of FIG. 14.

As the guides 37 are formed on the outer circumferential surfaces of the bending blocks 36, the manipulation members inserted into the respective guides 37 are disposed along the outer circumferential surfaces of the bending blocks 36 in the bending section 31. As shown in FIG. 17, in the insertion section 30 of the proximal end side rather than the bending section 31, the manipulation member 38 is inserted into a coil sheath 39 to extend to the first dial section 51 of the manipulation section 50. Since a distal end of the coil sheath 39 is fixed to an outer surface of a final block 42 connected to the bending blocks 36 and disposed at the most proximal end of the bending section 31, the manipulation member 38 extending outward from the bending section 31 extends to the manipulation section 50 in a substantially linear state. As a result, unnecessary resistance is not likely to occur upon advancing and retracting of the manipulation member 38.

The manipulation section 50 of the overtube 2 is described. The second dial section 52 configured to perform manipulation of the left arm section 4 includes a first knob 52A configured to bend the bending section 220 in two directions among the upward/downward and rightward/leftward directions, a second knob 52B configured to bend the bending section 220 in two directions perpendicular to the above two directions, a lever 56 configured to move the bending displacement section 230, and a release button 57 configured to release the motion of the bending displacement section 230. The structures and motions in use of the first knob 52A and the second knob 52B are the same as that of a conventional endoscope apparatus. The structures and motions of the lever 56 and the release button 57 are described in detail.

Figure 18:
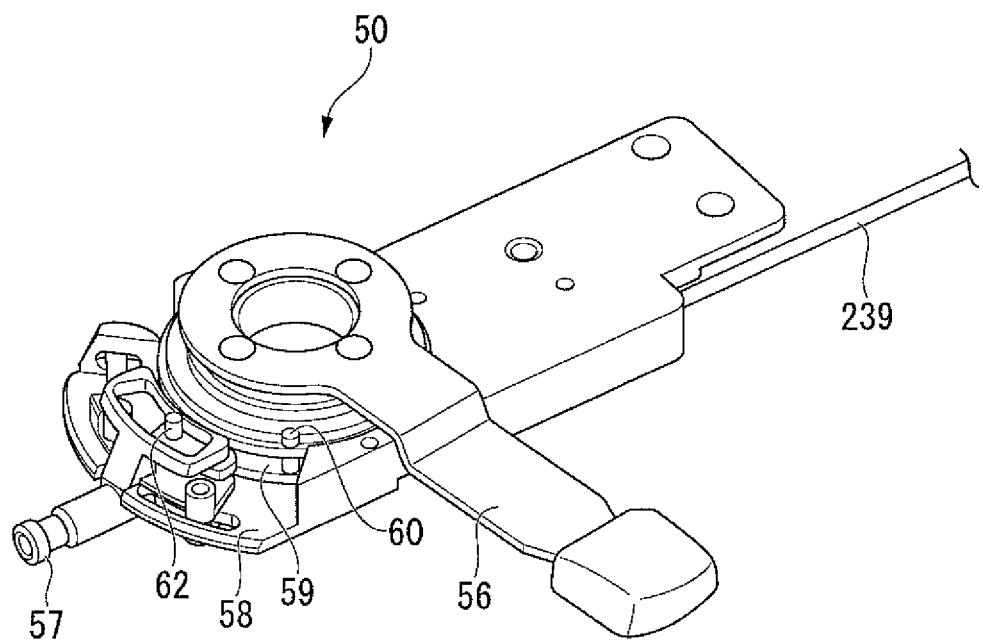
FIG. 18 is a perspective view showing a structure of a second dial section.
Figure 19:
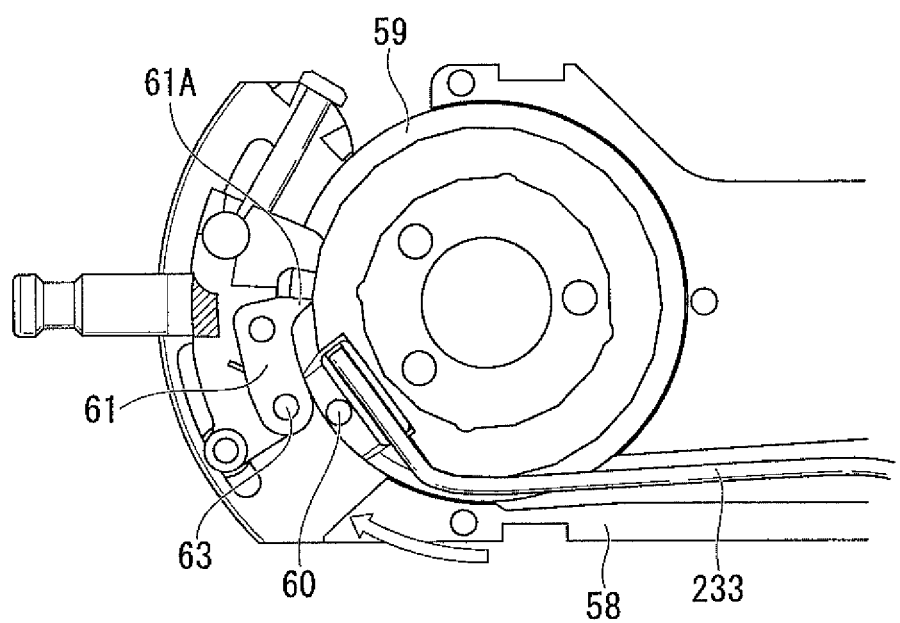
FIG. 19 is a view showing a motion of the second dial section in use.

FIG. 18 is an exploded view showing the manipulation section 50, except for the first knob 52A and the second knob 52B. The proximal end of a towing member (not shown) connected to the bending displacement section 230 through the coil sheath 239 is fixed to a pulley 59 rotatably attached to a manipulation section base 58, and the lever 56 is also fixed to the pulley 59. As shown in FIG. 18 and FIG. 19 (shown except for the lever 56), a pin 60 protrudes from a portion of a rim section of the pulley 59 to which an end of the towing member 233 is fixed. A lock member 61 having a claw 61A is rotatably attached to the manipulation section base 58 about a rotating shaft 63 in the vicinity of a rim of the pulley 59. A biasing member such as a torsion spring or the like (not shown) is attached to the lock member 61, and in a normal state, as shown in FIG. 19, the claw 61A is moved to a position at which the claw 61A is able to interfere with the pin 60.

When the lever 56 is rotation-manipulated, the pulley 59 is rotated to tow the towing member 233. When the pulley 59 is rotated by a predetermined degree, the pin 60 brings in contact with the claw 61A. When the pulley 59 is further rotated, the pin 60 resists against a biasing force of the biasing member to separate the claw 61A from the pulley 59, and gets over the claw 61A. Then, the bending displacement section 230 is actuated, and as described above, the bending section 220 is spaced apart from the overtube 2.

Figure 20:
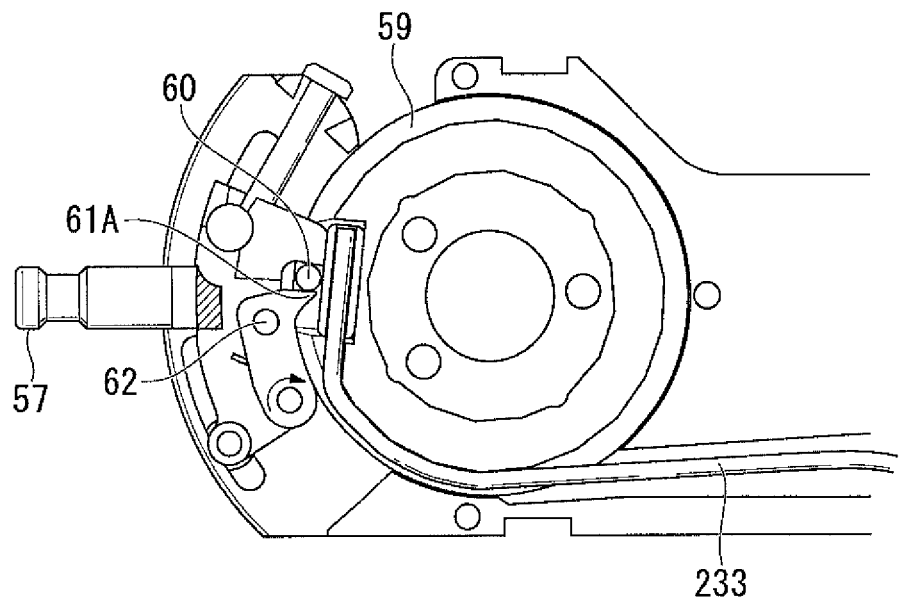
FIG. 20 is a view showing a motion of the second dial section in use.

After the pin 60 gets over the claw 61A, the lock member 61 is returned to a normal position by a force of the biasing member. Here, as shown in FIG. 20, since a surface of the pin 60 side of the claw 61A is substantially perpendicular to the rim of the pulley 59, even when the towing member 233 is to be moved to the distal end side by a tension thereof, the pin 60 in contact with the claw 61A cannot separate the claw 61A from the pulley 59. Accordingly, the pin 60 cannot get over the claw 61A, and the towing state of the towing member 233 is maintained to maintain the actuation state of the bending displacement section 230.

Figure 21:
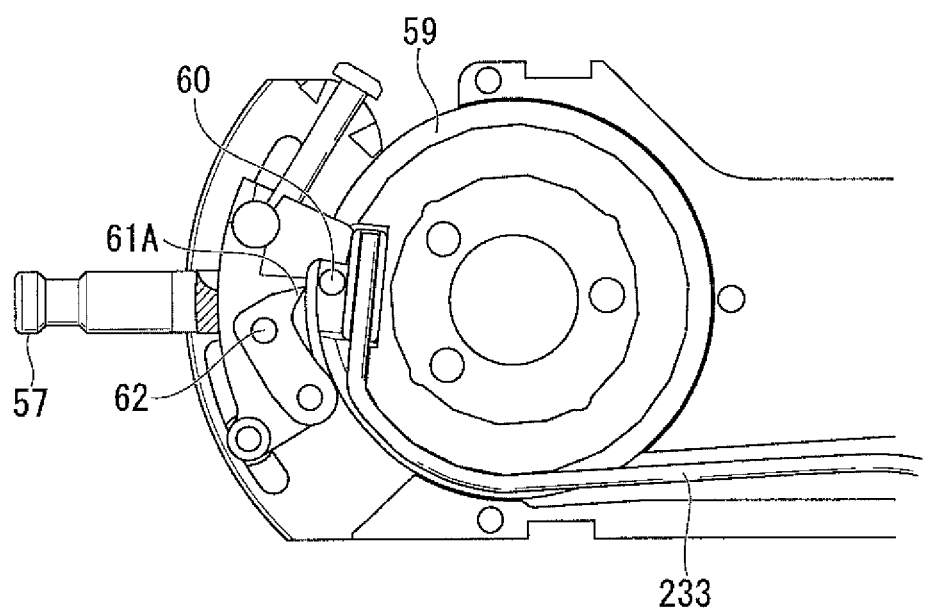
FIG. 21 is a view showing a motion of the second dial section in use.

When the actuation state of the bending displacement section 230 is released, it is necessary that the lever 56 is manipulated to rotate the pulley 59 and the towing member 233 is pushed into the distal end side. However, the pulley 59 is not rotated as it is by engaging the pin 60 with the claw 61A. Therefore, a user such as an operator first raises the release button 57. As shown in FIG. 18, since a portion of the release button 57 is engaged with a protrusion 62 protruding on the lock member 61, the claw 61A as shown in FIG. 21 is separated from the pulley 59 by raising the release button 57, and does not interfere with the pin 60. As a result, the pulley 59 is rotated by tension of the towing member 233. After that, the user releases the release button 57. Even when the lock member 61 is returned to the normal position, since the pin 60 is not engaged with the claw 61A, the pulley 59 can be rotated. In this state, when the lever 56 is manipulated to push the towing member 233, the actuation state of the bending displacement section 230 is released.

Figure 22:
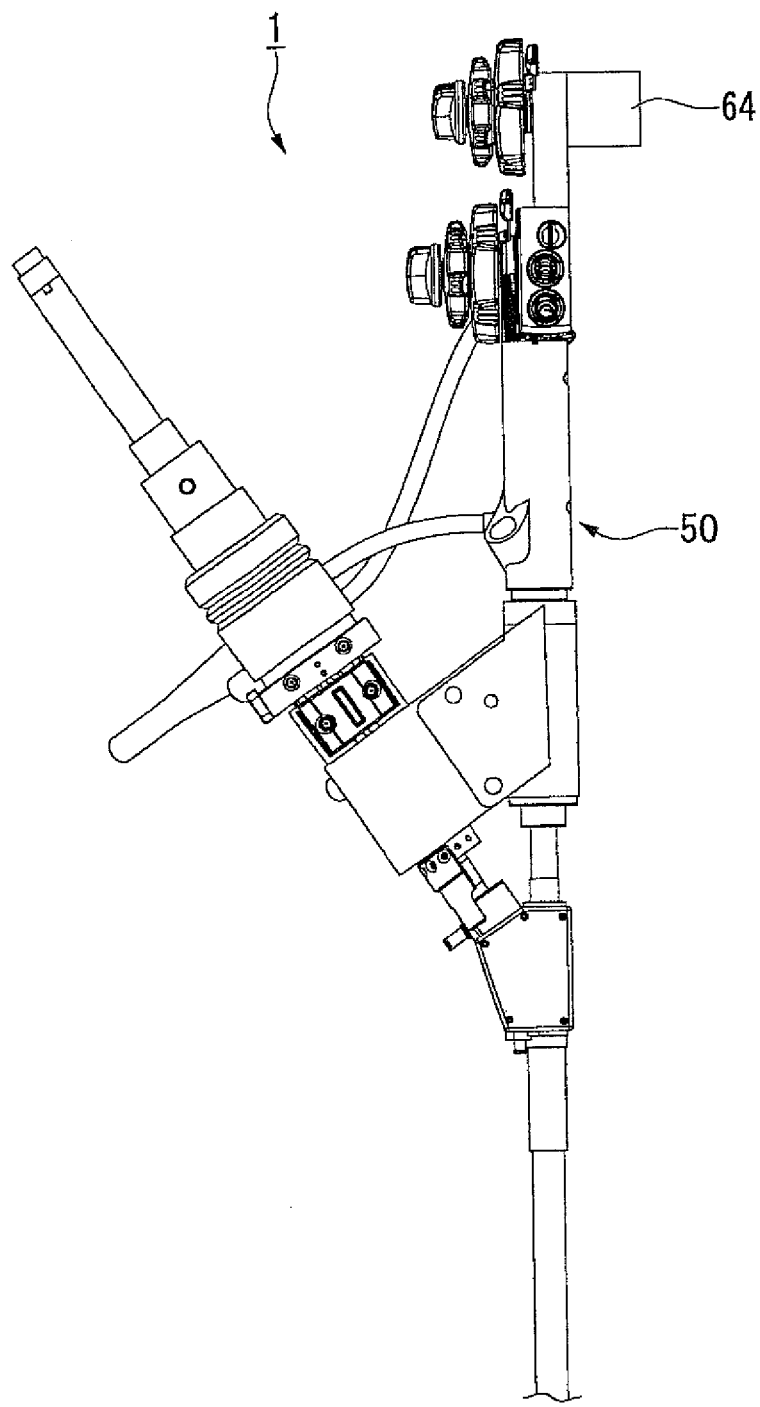
FIG. 22 is a view of a manipulation section of the overtube of the endoscope according to the first embodiment of the present invention when seen from different angles.

As shown in FIG. 22, an engagement protrusion 64 protrudes from the other side of a second dial section 52 in the manipulation section 50. Accordingly, the operator can manipulate the first dial section 51, the second dial section 52, the button section 53, and so on, while stably holding the manipulation section 50 using a weight of the endo scope 1 by hooking the engagement protrusion 64 on his/her hand, while not gripping the manipulation section 50. The engagement protrusion 64 may be detachable with respect to the manipulation section 50, and a plurality of kinds of engagement protrusions may be provided. As a result, an optimal engagement protrusion 64 can be selected and attached according to the size of the operator's hands to further improve manipulation feeling.

In the endoscope 1 of the embodiment, the right arm section 3 including the observation unit 112 may be more frequently manipulated than the left arm section 4. For this reason, even when a mechanism configured to manipulate the left arm section 4 is attached to the overtube 2 as the second dial section 52, the manipulation feeling upon performance of the procedure dose not get worse. Accordingly, the manipulation section can be compact, and can constitute the endoscope with no problem related to the manipulation feeling.

In addition, the button section 53 configured to perform air supply, water supply, and suction is installed in the vicinity of the first dial section 51 and the second dial section 52. For this reason, the air supply, water supply, suction, and so on, can be easily performed while performing bending manipulation via the dial sections 51 and 52. In addition, a portion of the air supply/water supply/suction channel 113 entering the manipulation section 50 from the right arm section 3 is detachable with respect to the manipulation section 50, and can perform cleaning or sterilization.

Figure 23:
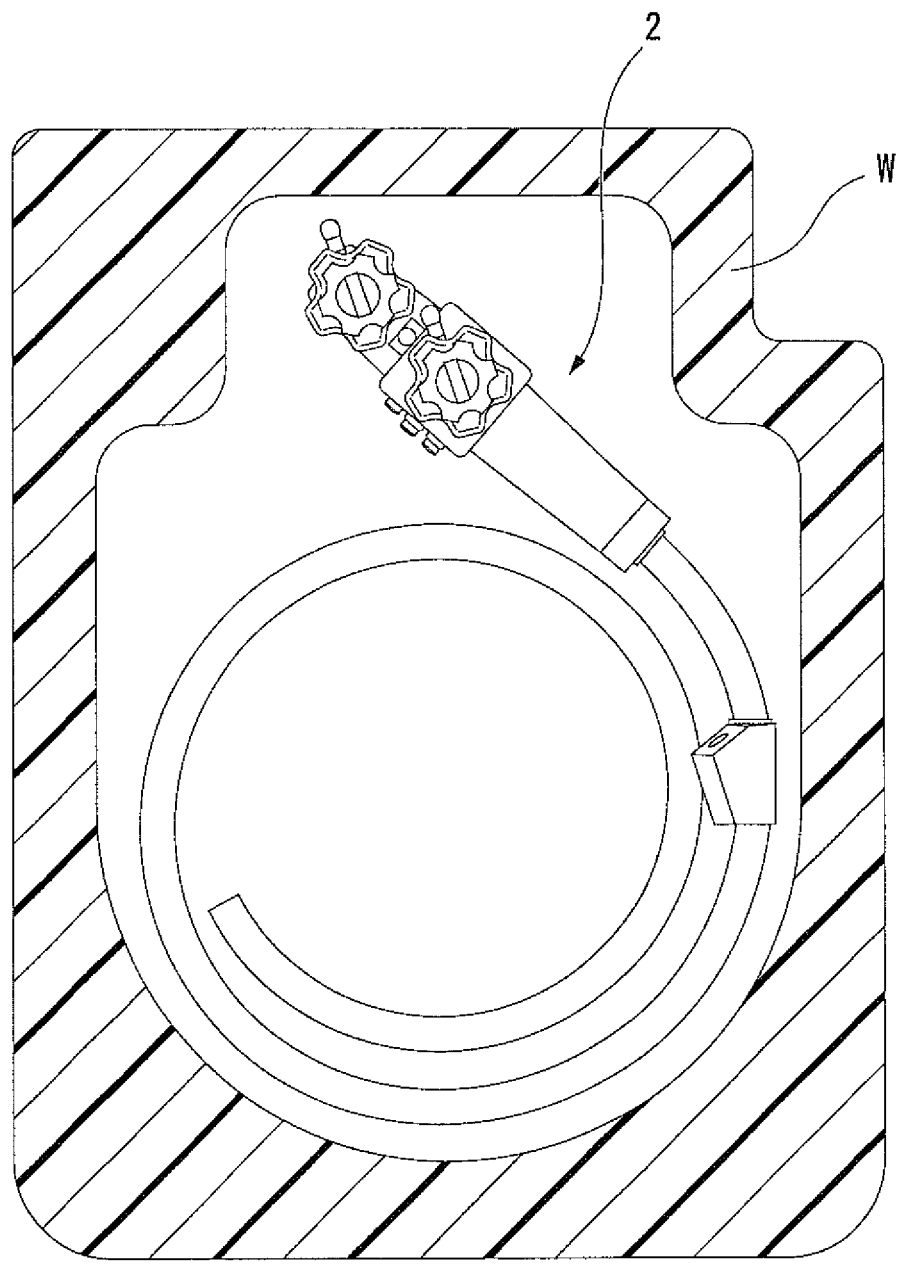
FIG. 23 is a view of a washing apparatus in which the overtube of the endoscope according to the first embodiment of the present invention is accommodated.

In the overtube 2, while the insertion section 30 is formed of a flexible material, when a region between the branch member 33 and the holder 54 is bent during the procedure, the endoscope cannot be easily manipulated. For this reason, the reinforcement member 41 (see FIG. 1) whose cross-sectional surface perpendicular to the axis is C-shaped, formed by removing an outer circumferential surface of a portion of a cylindrical member formed of metal, rigid resin, or the like, is fitted and attached to the region during the procedure, and the region becomes difficult to be bent in use. When the overtube 2 is cleaned after use, the reinforcement member 41 is removed. Therefore, the region becomes flexible, and as shown in FIG. 23, the overtube 2 can be put into a washing apparatus W of a conventional endoscope to be cleaned.

(Right Arm Section)

Figure 24:
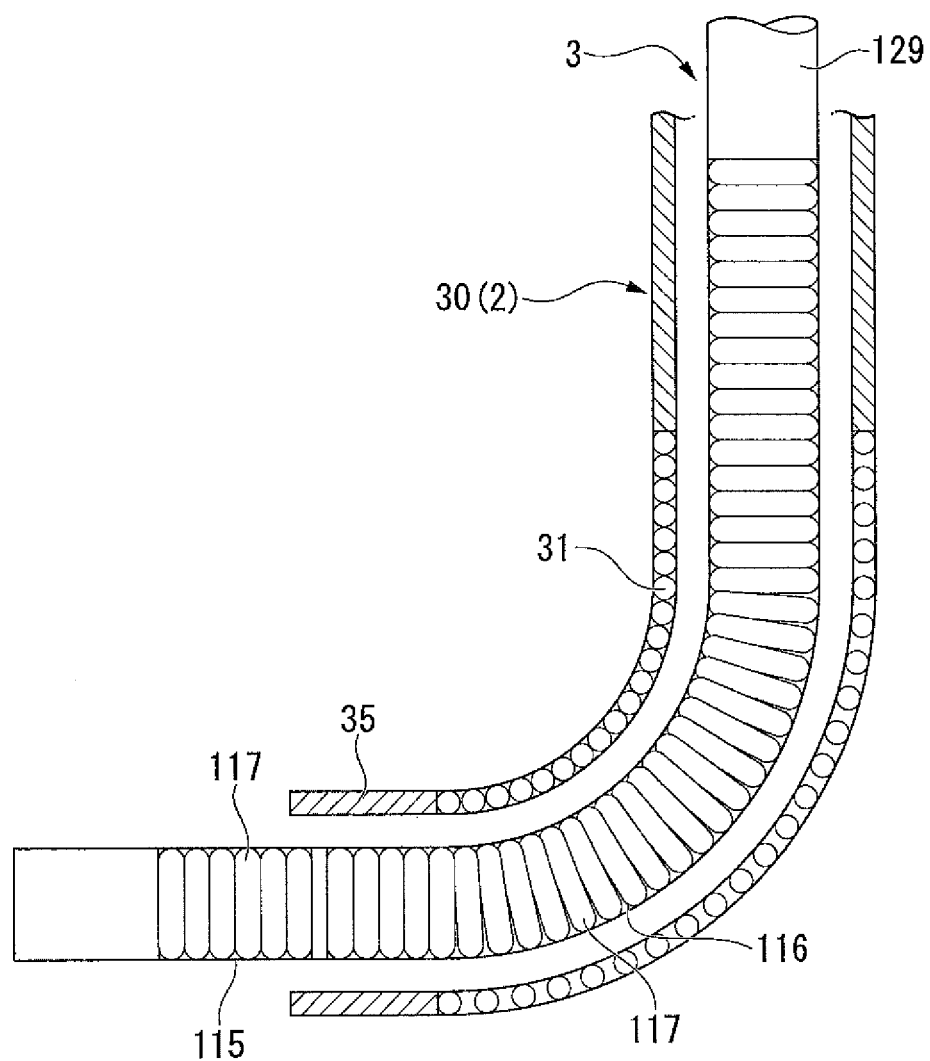
FIG. 24 is a schematic view of the overtube in which the right arm section is inserted.

FIG. 24 is a schematic view showing the overtube 2 into which the right arm section 3 is inserted. It has been previously described that the insertion section 110 has the active bending section and the passive bending section. Both of an active bending section 115 and the passive bending section 116 have annular bending blocks 117 connected in the axial direction. A guide (not shown) is formed at a bending block of the active bending section 115 only, and a manipulation member (not shown) such as a wire or the like is inserted into the guide, unlike the passive bending section 116. The manipulation member is inserted into a coil sheath (not shown), not inserted into the bending block of the passive bending section 116, to pass through the inner cavity of the passive bending section 116 and extend to the manipulation section 130. Accordingly, the passive bending section 116 is flexibly bent according to the shape of the inner cavity of the overtube 2, into which the passive bending section 116 is inserted, without influence of the bending manipulation of the manipulation section 130.

Figure 25:
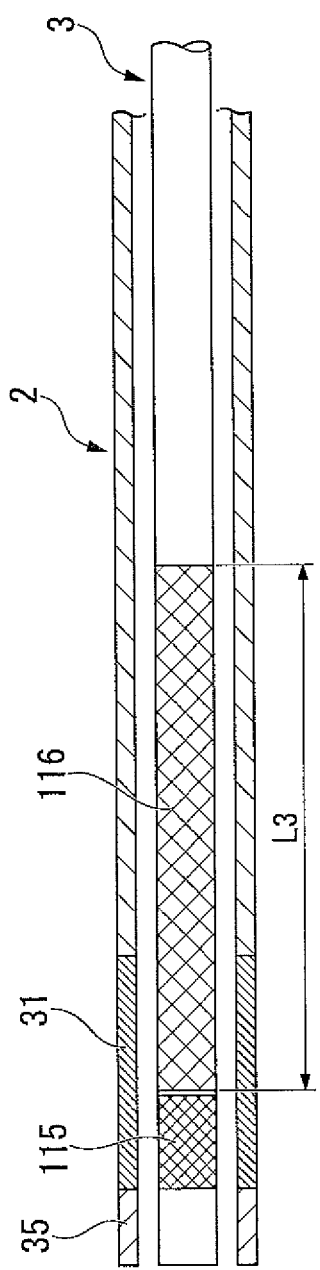
FIG. 25 is a view showing a positional relation between the right arm section and the overtube.
Figure 26:
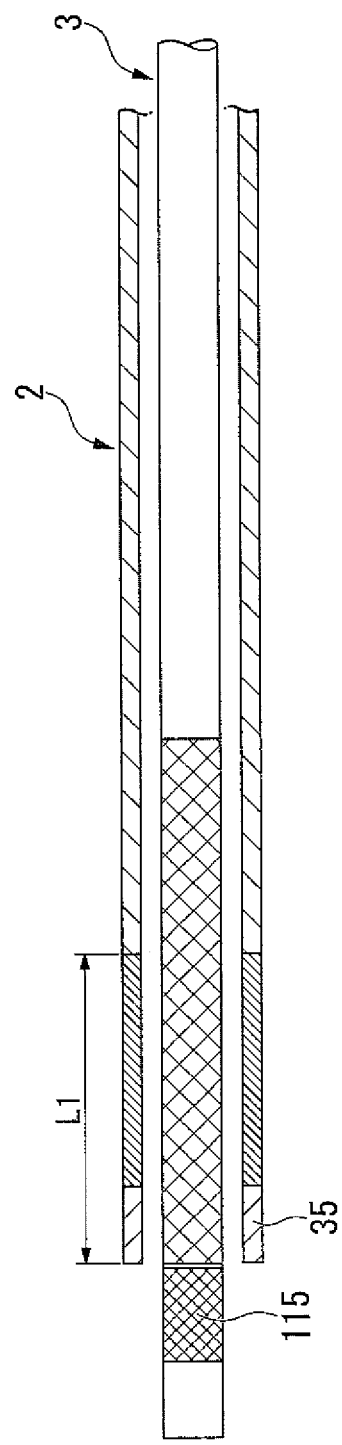
FIG. 26 is a view showing a positional relation between the right arm section and the overtube.
Figure 27:
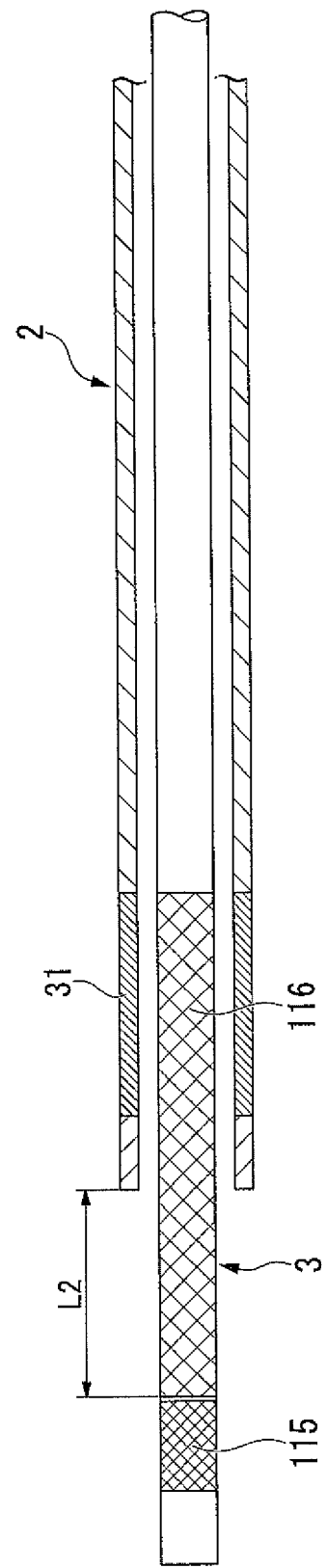
FIG. 27 is a view showing a positional relation between the right arm section and the overtube.

FIG. 25 to FIG. 27 are views showing a positional relation between the right arm section 3 and the overtube 2. When the bending section 31 of the overtube 2 is bent, advancing and retracting of the right arm section 3 becomes difficult. For this reason, in use of the endoscope 1, as a length of the passive bending section 116 is set such that the bending section 31 and the passive bending section 116 overlap each other in the axial direction, smooth advancing and retracting of the right arm section 3 is possible. Specifically, as shown in FIG. 27, in a state in which the right arm section 3 maximally protrudes, a length of the passive bending section 116 is set such that a proximal end of the passive bending section 116 is disposed at the same position as the proximal end of the bending section 31 or nearer a hand side of the endoscope 1. In order to satisfy the above conditions, it is necessary that the length of the passive bending section 116 is equal to or more than a length L1 (see FIG. 26) of a region including the cap 35 and the bending section 31 in the insertion section of the overtube 2, and the difference between the both lengths is equal to or more than a length L2 (see FIG. 27) of an area of the passive bending section 116 protruding from the overtube 2 in a state in which the right arm section 3 maximally protrudes. That is, provided that the length of the passive bending section 116 is L3, the length of each section is set such that a relation of L3−L1≥L2 is satisfied, and thus, smooth advancing and retracting of the right arm section 3 becomes possible.

When the right arm section 3 is moved back into the overtube 2 in a state in which the active bending section 115 of the right arm section 3 is bent, the active bending section 115 interferes with the overtube 2, and the right arm section 3 may be damaged. In order to prevent the damage, a bending release section, configured to release the bending of the active bending section 115 when the right arm section 3 is retracted to a predetermined position, is installed at the right arm section 3.

Accordingly, at a position like the inside of the overtube 2 where the bending of the active bending section 115 of the right arm section 3 is restricted, the active bending section 115 is able to be in a passively bendable state, and at a position like the outside of the overtube 2 where the active bending section 115 of the right arm section 3 is not restricted, the active bending section 115 is able to be in an actively bendable state.

Figure 28:
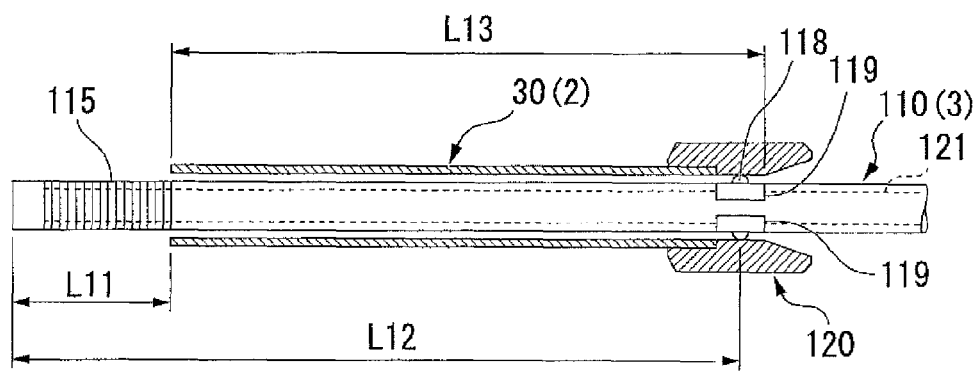
FIG. 28 is a view showing a basic structure of a bending release section.
Figure 29:
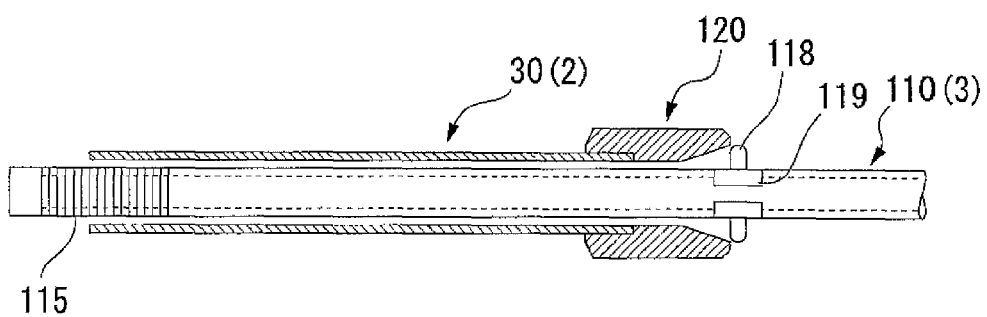
FIG. 29 is a view showing a basic structure of the bending release section.

FIG. 28 and FIG. 29 are views showing a basic structure of the bending release section. Protrusions 118 protruding on the outer circumferential surface are formed at the proximal end side of the insertion section 110. The protrusions 118 are formed one-by-one with respect to four manipulation members corresponding to the bending in the upward/downward and rightward/leftward directions. A switching mechanism 119 configured to switch a towable state of each of the manipulation members on and off is disposed at a position where each of the protrusions 118 is retracted in the insertion section 110. A bending release section 120 of the embodiment is composed of the protrusion 118 and the switching mechanism 119.

As shown in FIG. 29, in a state in which the protrusion 118 completely protrudes, a manipulation member 121 of the distal end side rather than the switching mechanism 119 is in a non-towable state by the switching mechanism 119. For this reason, even when the manipulation section 130 is manipulated, the active bending section 115 is not bent. When the right arm section 3 is inserted into the insertion section 30 and the active bending section 115 completely protrudes from the insertion section 30 as shown in FIG. 28, each of the protrusions 118 is pushed by an inner wall of the insertion section 30 and is retracted, and enters the switching mechanism 119. Then, since the manipulation member 121 is in a towable state by the switching mechanism 119, the active bending section 115 can be bent in a desired direction by manipulating the manipulation section 130. When the right arm section 3 is retracted with respect to the insertion section 30 and the active bending section 115 starts to enter the insertion section 30, since each of the protrusions 118 moves outside the insertion section 30 again, the protrusions 118 protrude and the manipulation member 121 cannot be towed. Accordingly, since the bending shape of the active bending section 115 is not maintained by the manipulation member 121 and follows shapes of the insertion section 30 and the bending section 31 to be easily bent, the probability of damage to the active bending section 115 due to advancing and retracting of the right arm section 3 is reduced.

In order to enable the above-mentioned motion of the bending release section 120 (a first acting section), it is only necessary that a dimensional relation of L11, L12, and L13 shown in FIG. 28 is set to be L11+L13≤L12. In addition, L11 and L12 are a length from the distal end of the right arm section 3 to the proximal end of the active bending section 115 and a length from the distal end of the right arm section 3 to the protrusion 118, respectively. L13 is a distance between the distal end of the overtube 2 and a position of the most proximal end side of the overtube 2 where the protrusion 118 is pushed such that the motion of the switching mechanism 119 is switched.

A specific configuration of the bending release section is described below as several examples, while not particularly limited as long as the function is shown.

Figure 30:
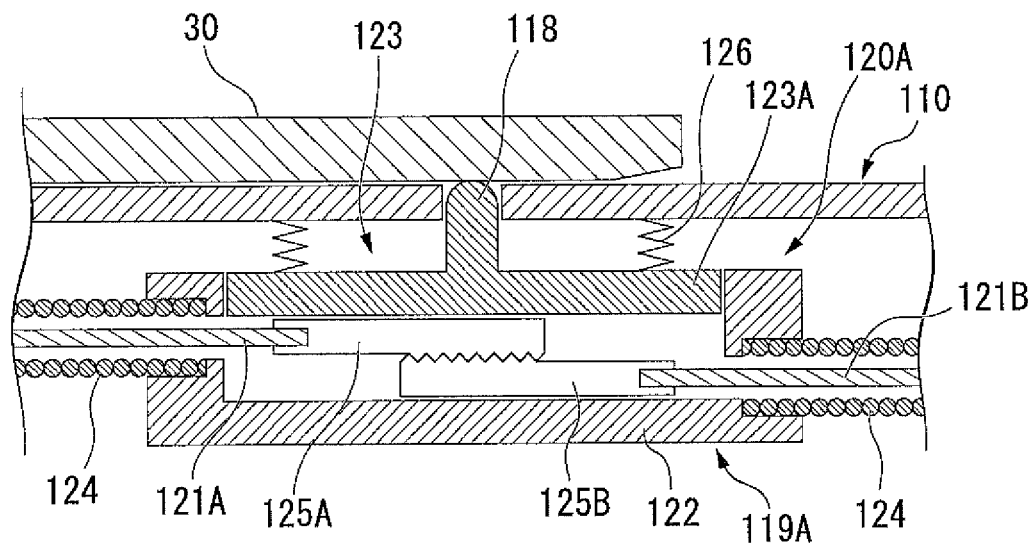
FIG. 30 is a view showing a structure of a first example of a bending release section of the right arm section.
Figure 31:
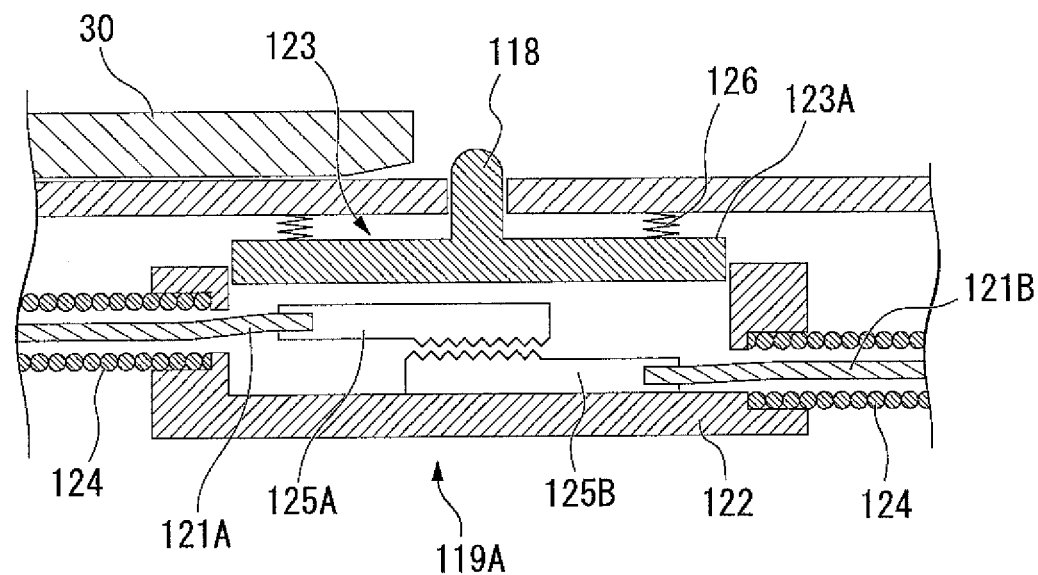
FIG. 31 is a view showing a structure of the first example of the bending release section of the right arm section.

FIG. 30 and FIG. 31 are views showing a structure of a first example of the bending release section. The switching mechanism 119A in the bending release section 120A of the example includes a housing 122 into which the manipulation member 121 is inserted, and a protrusion member 123 disposed to partially enter the housing 122. A coil sheath 124 into which the manipulation member 121 is inserted is connected to a distal end side and a proximal end side of the housing 122.

The manipulation member 121 is divided into the first manipulation member 121A of the distal end side and the second manipulation member 121B of the proximal end side, and the members enter the housing 122 from the distal end side and the proximal end side of the housing 122, respectively. Engagement sections 125A and 125B, which are engageable with each other, are formed at the proximal end section of the first manipulation member 121A and the distal end section of the second manipulation member 121B, respectively.

The protrusion member 123 has a plate-shaped base 123A, and the protrusion 118 protruding onto the base 123A, and the protrusion 118 and the switching mechanism 119A are integrated with each other. The protrusion 118 on the base 123A is biased to protrude to the outside of the insertion section 110 by a tension spring 126 (a second acting section). The protrusion member 123 is disposed such that at least a portion of the base 123A enters the housing 122 even when the protrusion 118 maximally protrudes.

In the switching mechanism 119A having the above-mentioned configuration, when the protrusion 118 is pressed by an inner surface (a restricting surface) of the insertion section 30, as shown in FIG. 30, the protrusion member 123 further enters the housing 122, and presses the engagement sections 125A (a second connecting section) and 125B (a first connecting section) to engage the sections with each other. Accordingly, the right arm section 3 becomes in an ON state in which the first manipulation member 121A can be towed by the manipulation section 130. When the protrusion 118 protrudes, since the protrusion member 123 is separated from the engagement sections 125A and 125B as shown in FIG. 31, the engagement sections 125A and 125B are in a non-engaged state. As a result, the right arm section 3 becomes in an OFF state in which the first manipulation member 121A cannot be towed by the manipulation section 130.

Figure 32:
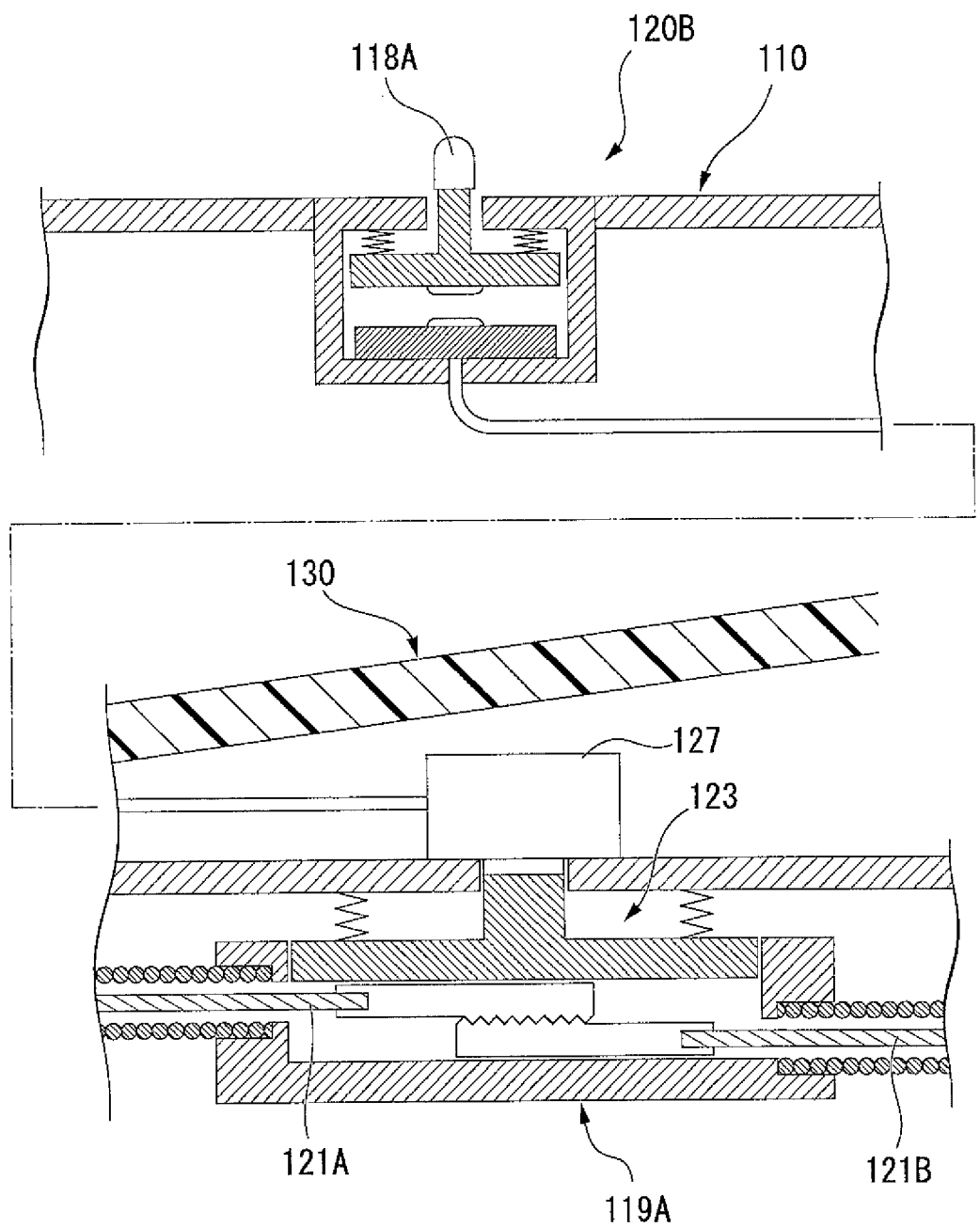
FIG. 32 is a view showing a structure of a second example of the bending release section.

FIG. 32 is a view showing a second example of the bending release section. In the bending release section 120B of the second example, the entire switching mechanism 119A is installed in the manipulation section 130, and a solenoid 127 (a first acting section) configured to drive the protrusion member 123 is attached thereto. In the second example, the protrusion 118A is formed at a place where the protrusion 118 is disposed in the first example, and the bending release section 120B is composed of the protrusion 118A and the switching mechanism 119A. The protrusion 118A is a switch configured to switch between the on and off actions of the solenoid 127. When the protrusion 118A is pressed, the solenoid 127 presses the protrusion member 123. Accordingly, the first manipulation member 121A is connected to the second manipulation member 121B, and the right arm section becomes in the ON state.

In the bending release section 120B of the second example, since it is possible to switch between the ON state and the OFF state by electrical means, the protrusion 118A may be formed at one place, and it is not necessary that the protrusions are respectively formed at each of the manipulation members 121. In addition, the switching mechanism 119A can be disposed in the manipulation section 130, and the diameter of the insertion section 110 can be easily reduced.

When a right arm section including the bending release section 120B of the second example includes the same manipulation section as the known endoscope having a pulley to which a bending knob and the manipulation member are connected and an electromagnetic clutch installed between the bending knob and the pulley, instead of the manipulation section 130, it is possible to switch between the ON state and the OFF state by connecting the switch having the protrusion 118A to the electromagnetic clutch.

In addition, a meshed section of the engagement sections 125A and 125B has a sufficient length. Therefore, even when the second manipulation member 121B is moved to advance and retract by manipulating the stick 131 in the OFF state, and the OFF state is switched to the ON state, the engagement section 125A and engagement section 125B can be engaged with each other.

Figure 33:
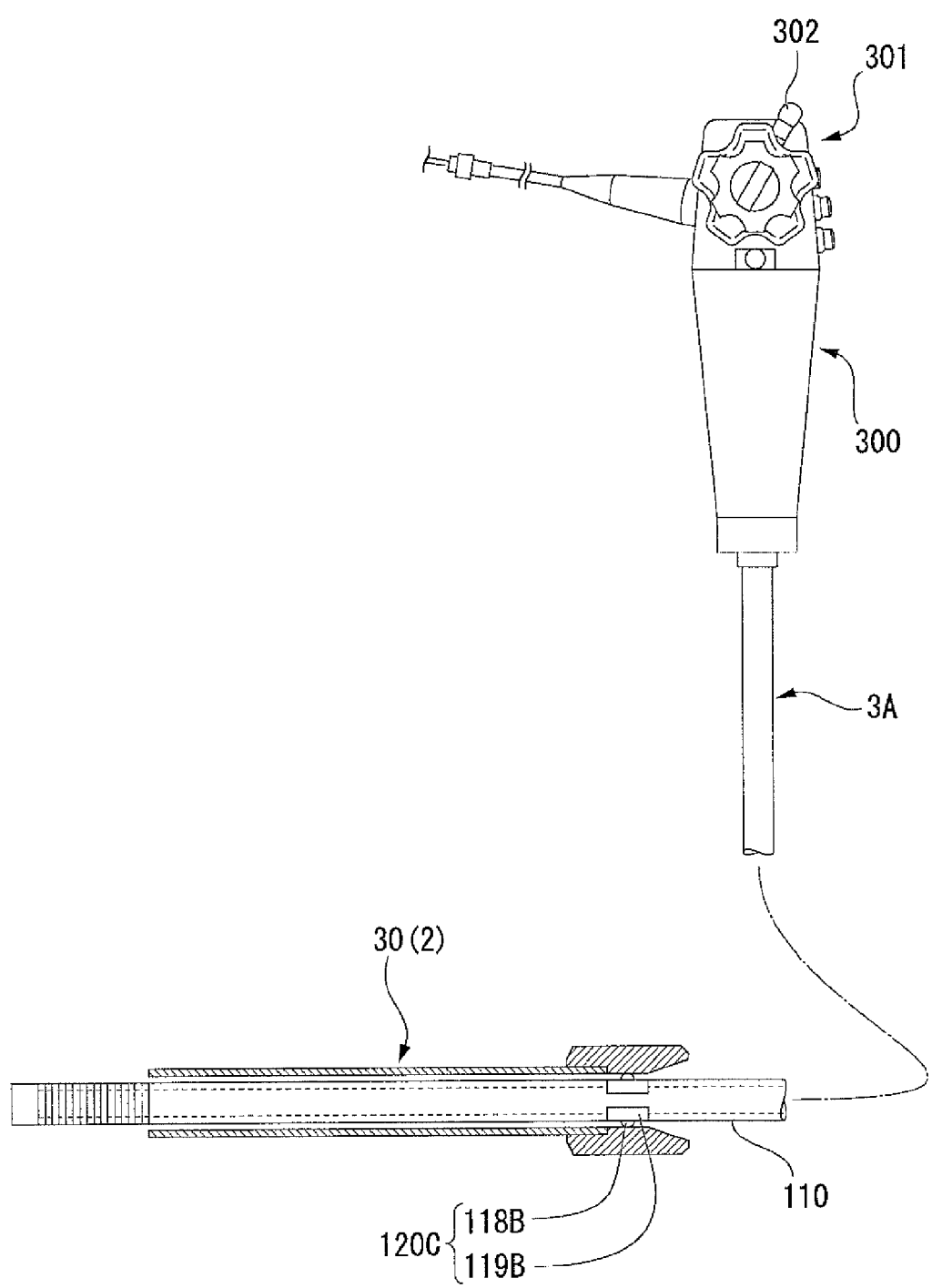
FIG. 33 is a view showing an example of a right arm section including a bending release section of a third example.

FIG. 33 is a view showing the right arm section 3A having a bending release section 120C of a third example. A manipulation section 300 of the right arm section 3A is the same as that of the conventional endoscope apparatus, and includes a knob 301 configured to perform bending manipulation, and a lock lever 302 configured to fix the knob 301.

Figure 34:
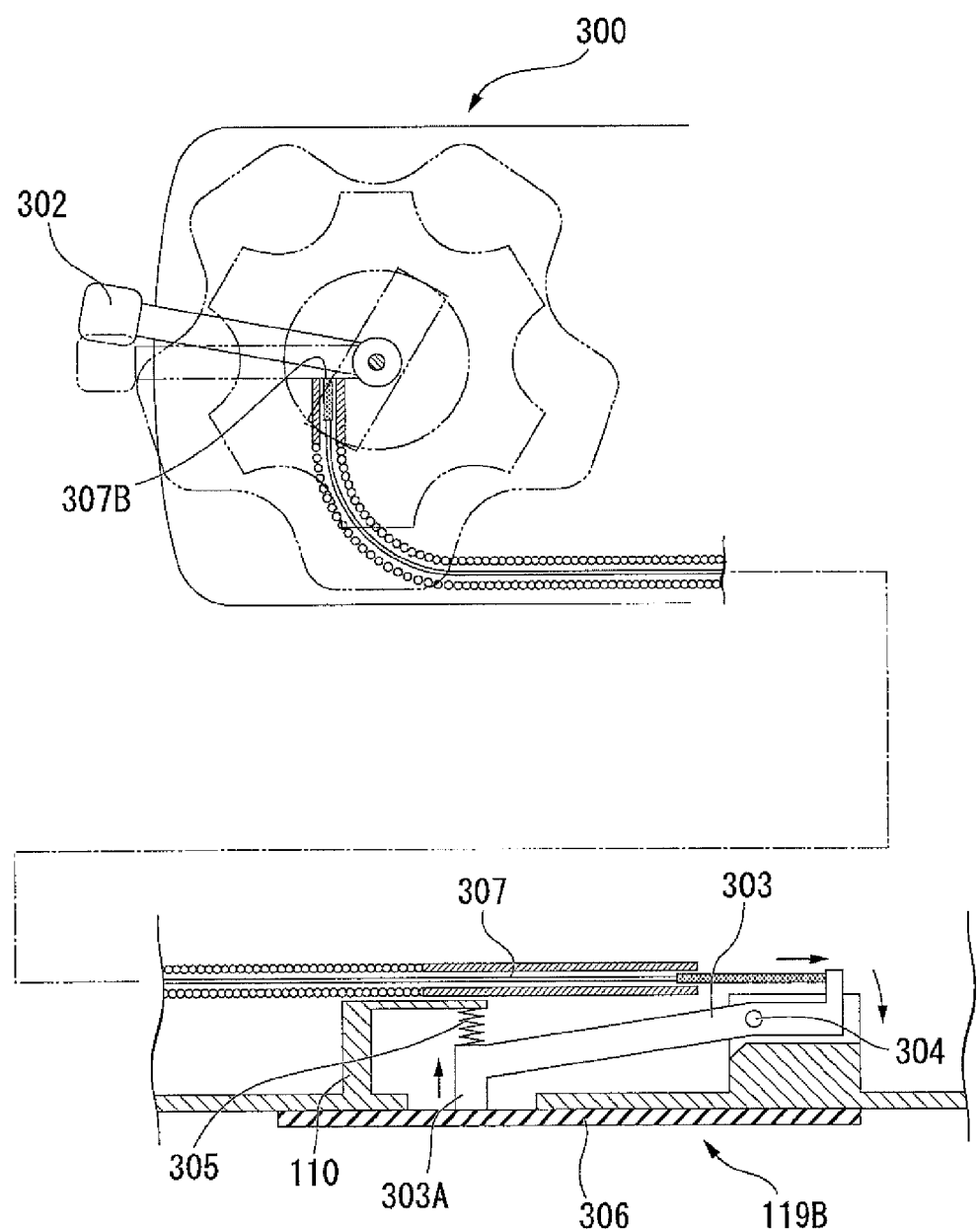
FIG. 34 is a view showing a motion of the bending release section of the third example.

As shown in FIG. 34, a rotating member 303 configured to rotate about a rotating shaft 304 is attached to the switching mechanism 119B. The rotating shaft 304 is fixed to an inner surface of the insertion section 110. A first end 303A of the rotating member 303 can protrude from a hole formed in the insertion section 110 to the outside of the insertion section 110 by rotating the rotating member 303. In addition, the other end of a biasing member 305 (a second acting section) such as a spring or the like is also fixed to the inner surface of the insertion section 110, and the first end 303A of the rotating member is biased by the biasing member 305 (the second acting section) to protrude to the outside of the insertion section 110. Further, when the rotating shaft 304 or the biasing member 305 is fixed to the insertion section 110 and not limited to the inner surface of the insertion section 110, the same function is shown. As the coating 306 formed of rubber or the like is attached to the hole and the protruded first end 303A is coated with the coating 306, the first end 303A functions as the protrusion 118B, which is a portion of the bending release section 120C.

A second end 303B of the rotating member 303 is connected to a distal end of a wire 307. The wire 307 is inserted into a pipe 308 and a coil sheath 309 configured to prevent bucking to extend to the manipulation section 300, and the proximal end thereof is disposed in the vicinity of the lock lever 302. A reinforcement pipe 310 is fitted and fixed onto the distal end and the proximal end of the wire 307 to increase stiffness. In the third example, the bending release section 120C including the protrusion 118A and the switching mechanism 119B is composed of the rotating member 303 and the wire 307 as major configurations.

Figure 35:
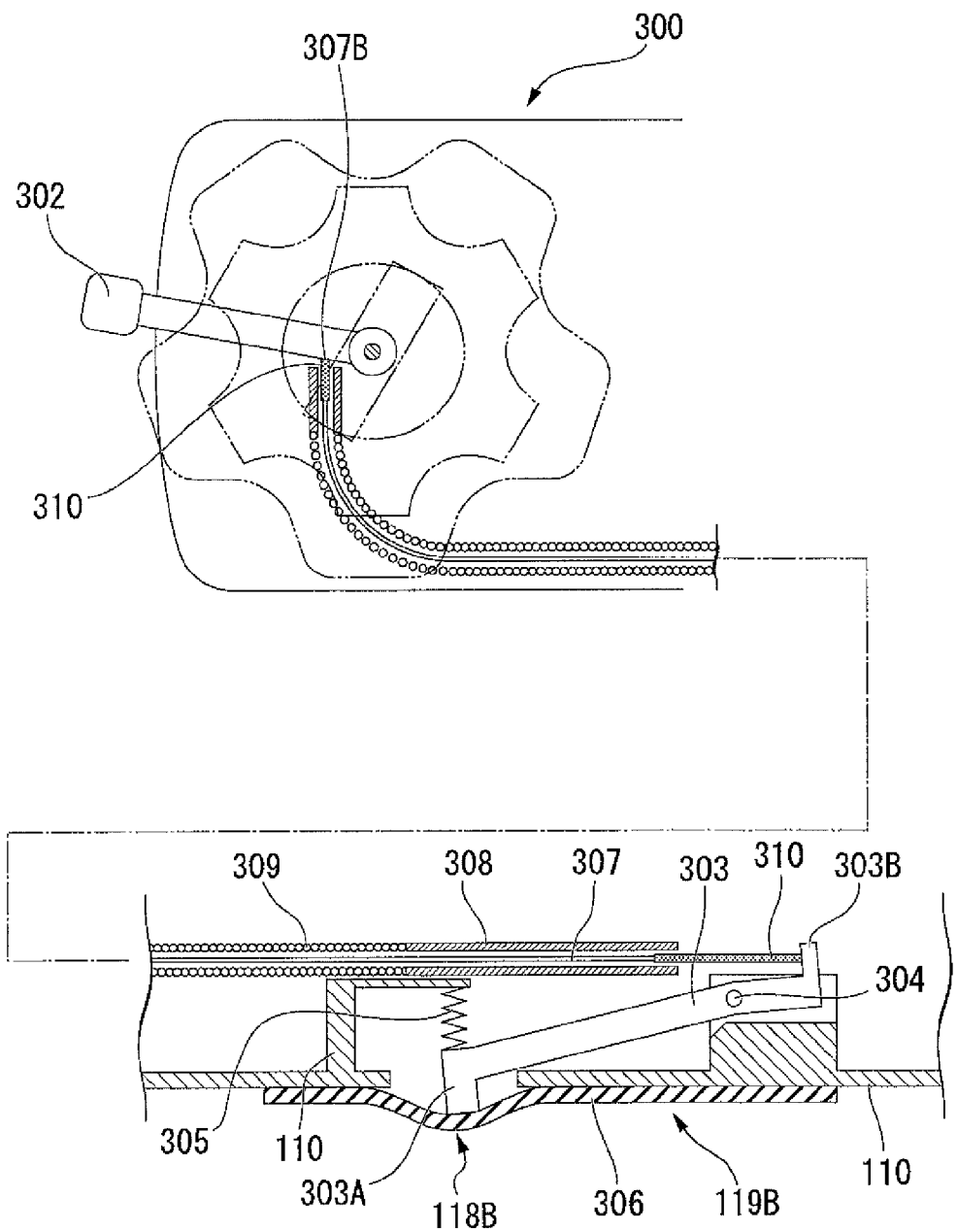
FIG. 35 is a view showing a motion of the bending release section of the third example.

In the bending release section 120C of the third example, when the protrusion 118B is pressed by the overtube 2 to be pushed into the insertion section 110, as shown in FIG. 34, the rotating member 303 rotates and the wire 307 is towed toward the distal end side. Then, a proximal end section 307B of the wire 307 is moved to a position in which the proximal end section 307B does not interfere with the lock lever 302, and the operator can manipulate the lock lever 302. When the protrusion 118B protrudes by the right arm section 3A being retracted with respect to the overtube 2, the wire 307 is retracted, and as shown in FIG. 35, the proximal end section 307B moves to a position in which the proximal end section 307B interferes with the lock lever 302. Accordingly, the lock by the lock lever 302 is released, and the fixed bending in the active bending section 115 is released.

In the state shown in FIG. 35, since the operator cannot manipulate the lock lever 302 to fix the knob 301, damage to the active bending section 115 by the active bending section of the locked right arm section 3A is prevented.

Figure 36A:
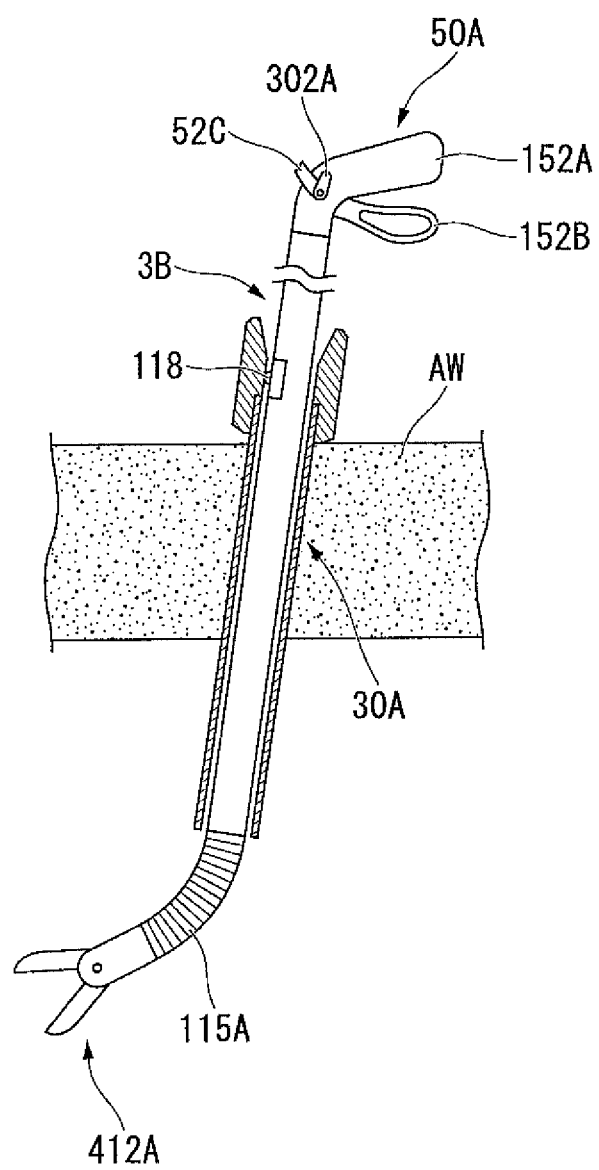
FIG. 36A is a view showing an example in which the right arm section including the bending release section is assembled with a trocar to be used.
Figure 36B:
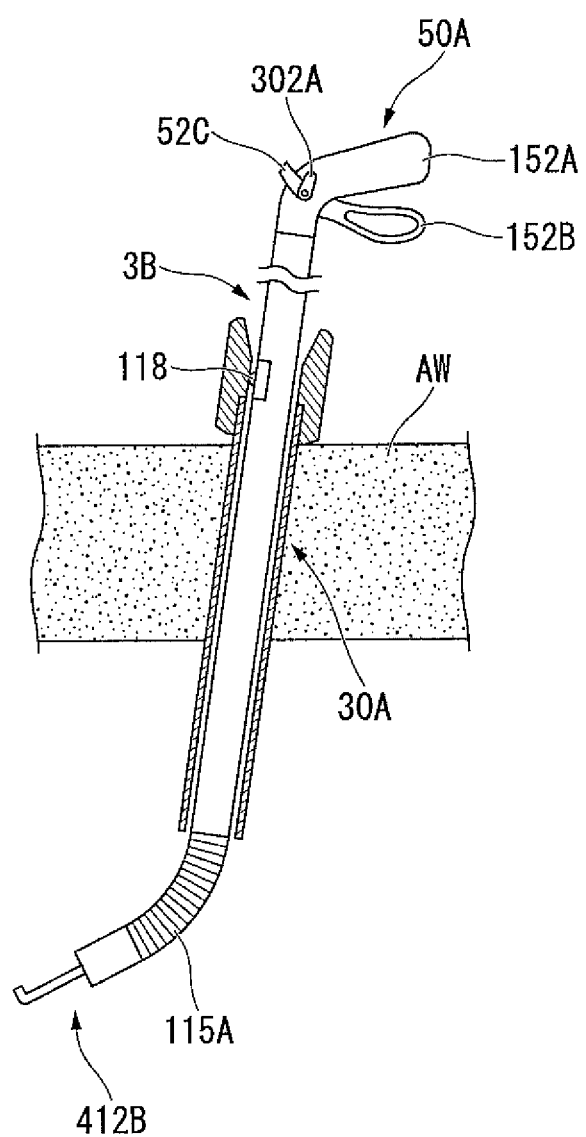
FIG. 36B is a view showing an example in which the right arm section including the bending release section is assembled with the trocar to be used.
Figure 36C:
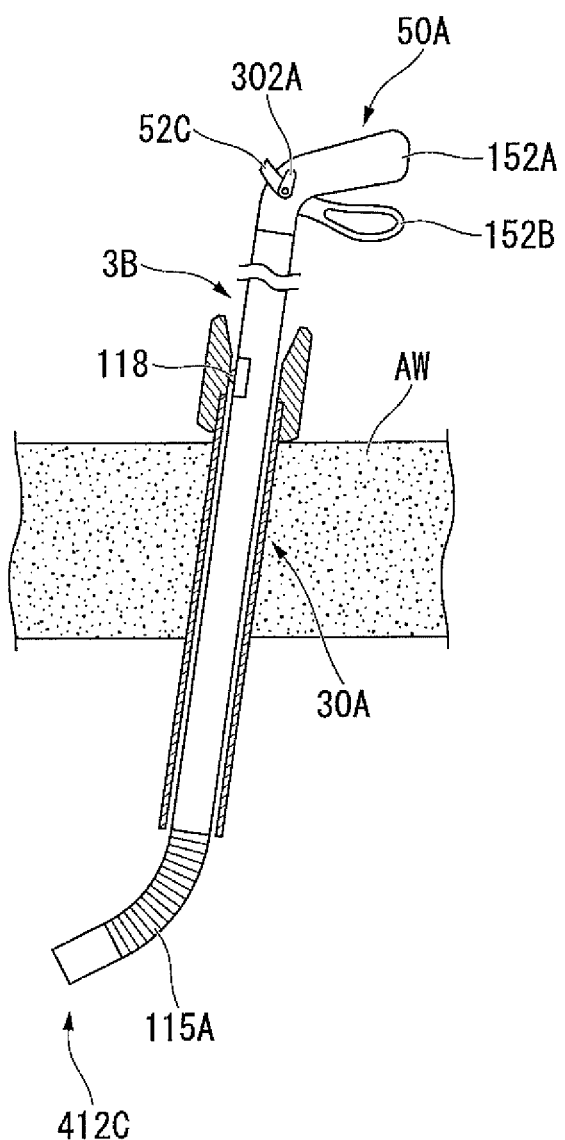
FIG. 36C is a view showing an example in which the right arm section including the bending release section is assembled with the trocar to be used.

The example in which the right arm section including the bending release section is assembled to a trocar and used is shown in FIG. 36A to FIG. 36C.

In FIG. 36A, a state in which the right arm section 3B is inserted into a trocar 30A is shown. The right arm section 3B has an active bending section 115A formed at a distal end of an insertion section, and a bent state is varied by a transmission member (a rod, a wire, or the like (not shown)) by manipulating a bending knob 52C. Further, the right arm section 3B has a lock lever 302A configured to maintain the bent state. In addition, in the right arm section 3B, a forceps section 412A is disposed at a distal side of the active bending section, and the forceps section 412A is opened and closed by a first holding section 152A and a second holding section 152B disposed at the manipulation section 50A. Further, the protrusion 118 is formed at the insertion section. The protrusion 118 is pushed by contacting with the inner surface of the trocar 30A.

When the protrusion 118 is pushed inward, the active bending section 115A is configured to have a length entirely protruding a distal side more than a distal end of the trocar 30A. The above motion is the same motion in FIG. 28 to FIG. 35 in that as the protrusion 118 is pushed inward, a manipulation member (a wire) is in a towable state to bend the active bending section 115A, and the lock lever 302 is in a manipulatable state.

Here, while an example of the grasping forceps having the forceps section 412A disposed at the distal side of the active bending section 115A has been shown, instead of the forceps section 412A, a high frequency knife (FIG. 36B) on which an electrode 412B is disposed, and an endoscope (FIG. 36C) on which an imaging sensor and an optical part are disposed may be provided.

Next, the manipulation section 130 of the right arm section 3 is described in detail. An anti-dropping mechanism configured to prevent the mounted treatment instrument from being dropped during the procedure is installed at the stick 131, and a detailed configuration is described with a description of the treatment instrument.

A basic structure of the swing mechanism 140 is the same as disclosed in United States Patent Publication Application No. 2010/0063354, and as a swing center of the stick is switched when swing is performed in two directions (for example, right and left directions of the upward/downward and rightward/leftward directions) spaced apart from each other in the same swing surface, towing efficiency of the manipulation member is improved. In the structure disclosed in United States Patent Publication Application No. 2010/0063354, a mechanism configured to swing the stick on a first swing surface and a mechanism configured to swing the stick on a second swing surface perpendicular to the first swing surface are parallelly installed in an axial direction of the manipulation section. For this reason, a difference in a moment during manipulation between the mechanisms and generation of difference in manipulation feeling remain as problems. In the swing mechanism 140 of the embodiment, as the two mechanisms are disposed at substantially the same position in the axial direction of the manipulation section 130, manipulation feelings of the two mechanisms are the same and the entire swing mechanism can be further miniaturized. Hereinafter, a detailed description is provided.

Figure 37:
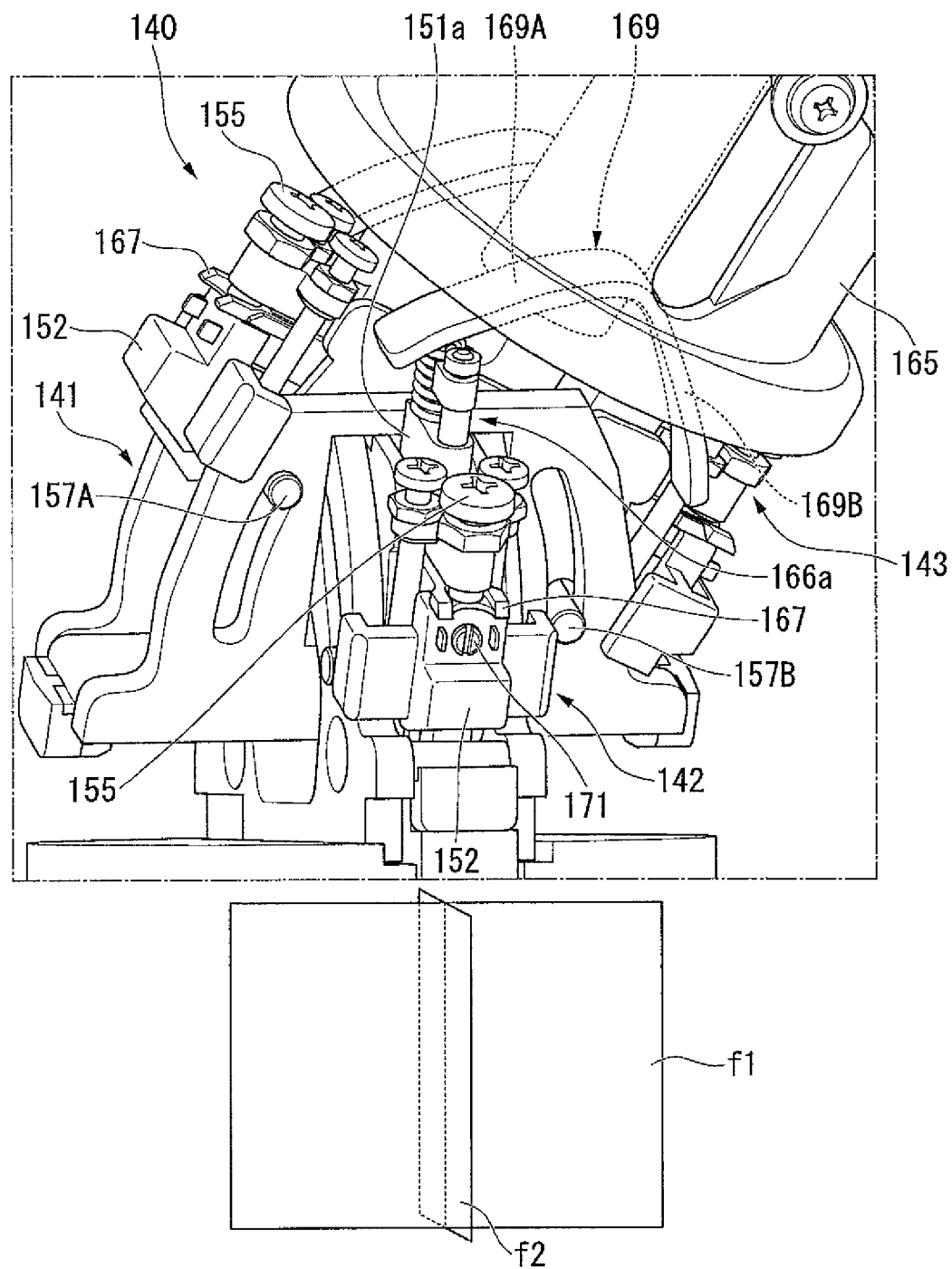
FIG. 37 is an enlarged view showing the inside of a swing mechanism of the manipulation section of the right arm section.

FIG. 37 is an enlarged view showing the inside of the swing mechanism 140, illustrating a state in which the stick 131 (not shown) is pulled down. The swing mechanism 140 includes a first swing section 141 configured to swing the stick 131 in two direction parallel to a first swing surface f1 among the upward/downward and rightward/leftward directions, a second swing section 142 configured to swing the stick 131 in the other two directions parallel to a second swing surface f2 perpendicular to the first swing surface f1, and an arbitrary locking section 143 configured to apply an arbitrary lock with respect to the first swing section 141 and the second swing section 142. In the embodiment, a swing direction of the first swing section 141 corresponds to a vertical direction of a visual field of the observation unit 112, and a swing direction of the second swing section 142 corresponds to a horizontal direction of the visual field. While the first swing section 141 and the second swing section 142 have some differences in shapes of components to be disposed perpendicular to each other, since basic structures are the same except for the above, structures of the first swing section 141 and the arbitrary locking section 143 are described below in detail.

Figure 38:
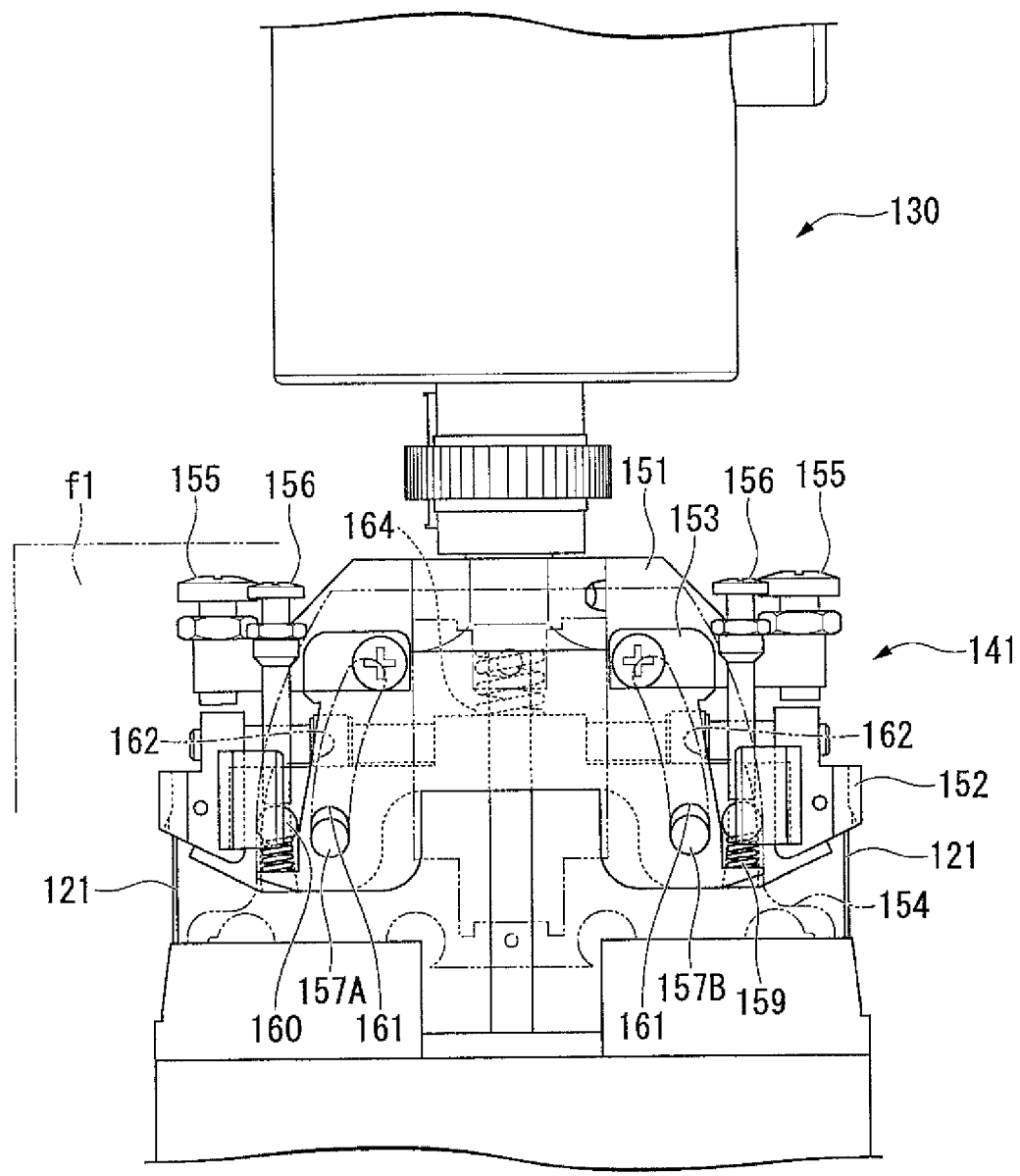
FIG. 38 is a view showing a first swing section of the swing mechanism of the third example.

FIG. 38 to FIG. 44 are views showing the structure and the motion of the first swing section 141. As shown in FIG. 38, the first swing section 141 includes a base frame 151 fixed to the stick 131 (not shown), a towing body 152 to which the manipulation member 121 connected to the active bending section 115 is connected, a pair of sandwich members 153 attached to a base frame to sandwich the base frame 151 and the towing body 152, and a pair of bases 154 disposed to sandwich and face the base frame 151, the towing body 152, and the sandwich members 153. In addition, hereinafter, a direction parallel to the first swing surface f1 and perpendicular to a central axis of the manipulation section 130 is defined and described as a widthwise direction of the respective parts.

In the base frame 151, push screws 155 are attached to both ends in the widthwise direction, and release screws 156 are attached to the insides of the push screws 155, respectively. The release screws 156 are attached to both sides with respect to the base frame 151 in a direction (hereinafter, referred to as "a thickness direction") perpendicular to the first swing surface f1. That is, four release screws 156 are attached to the base frame 151.

Figure 39:
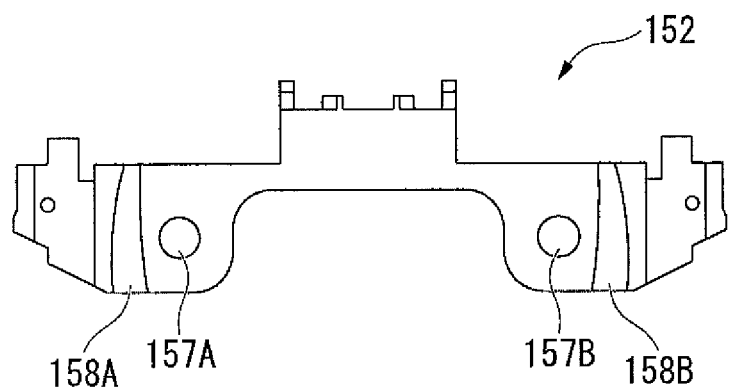
FIG. 39 is a view showing a towing body of the first swing section of the third example.

FIG. 39 is a view showing the towing body 152. A pair of pins 157A and 157B configured to be a swing center is formed on the towing body 152, and is disposed at positions opposite to each other with respect to a center in the widthwise direction.

As shown in FIG. 38, the manipulation members 121 configured to bend the active bending section 115 in an upward direction and a downward direction respectively are connected to both ends in the widthwise direction of the towing body 152. In an area between the each pins 157A and 157B and the each manipulation members 121 in the widthwise direction of the towing body 152, as shown in FIG. 39, a pair of locking grooves 158A and 158B configured to lock a swing state of the first swing section 141 is formed. While the locking grooves 158A and 158B have an arc shape centered at the pin 157B and the pin 157A, respectively, bottom surfaces of the locking grooves 158A and 158E are inclined several angles to be shallowed toward the proximal end side (a side at which the stick 131 is disposed, upper sides of FIG. 38 and FIG. 39). As a result, the widths of the locking grooves 158A and 158B are narrow at the proximal end side and broad at the distal end side. A pin and a locking groove are formed at both surfaces in a thickness direction of the towing body 152.

Figure 41:
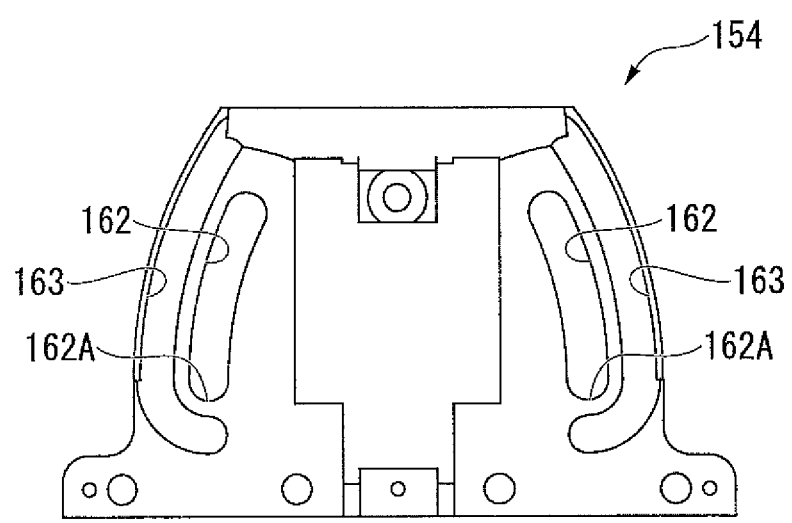
FIG. 41 is a view showing a base of the first swing section of the third example.

FIG. 41 is a view showing a surface of the base frame 151 side of the base 154. The base 154 is fixed to the manipulation section 130 not to move even when the stick 131 is pulled down, and has a pair of guide holes 162. One of the guide holes has an arc shape centered at a lower end 162A of the other of the guide holes, and functions as a guide configured to restrict movement of the towing body 152 when the first swing section 141 is swung. In addition, guide grooves 163 having a shape corresponding to the locking grooves 158A and 158B are formed in surfaces of the base frame 151 side of the base 154. The guide grooves 163 are different from the locking grooves 158A and 158B, and are formed to a certain depth throughout the entire length.

Figure 40:
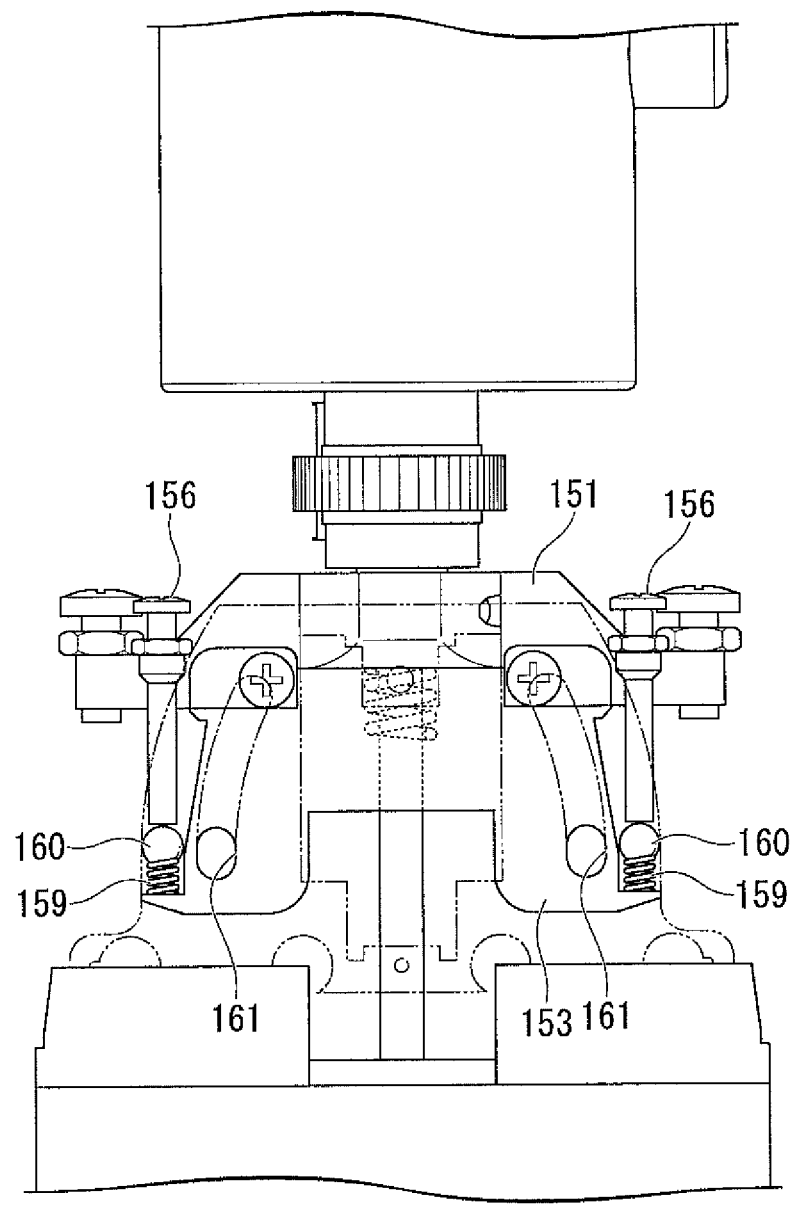
FIG. 40 is a view showing a sandwich member of the first swing section of the third example.

The sandwich members 153 are integrally attached to the base frame 151 and disposed between the towing body 152 and the pair of bases 154. As shown in FIG. 40, biasing members 159 such as springs disposed at both ends in the widthwise direction are attached to the sandwich members 153, respectively. Locking balls 160 are disposed between the respective biasing member 159 and the respective release screws 156. A diameter of the locking ball 160 is smaller than the width of a distal end side of ball moving grooves formed between the locking grooves 158A and 158B and the guide grooves 163 corresponding thereto and larger than the width of the proximal end side. In the widthwise direction of the sandwich members 153, a pair of long holes 161 is formed at an area more inside than the biasing member 159. The long holes 161 have a size into which the pins 157A and 157B can be inserted and a shape conforming to guide grooves (described later) of the base 154.

As shown in FIG. 38, the pair of sandwich members 153 is attached to the base frame 151 such that the pins 157A and 157B are inserted into the long holes 161. Since a spring 164 is disposed between the base frame 151 and the towing body 152, the towing body 152 is biased in a direction away from the base frame 151, and the pins 157A and 157B are biased toward a lower end of the long hole 161. That is, the base frame 151 and the towing body 152 are integrally swingably connected to each other via the sandwich members 153. However, the towing body 152 can relatively move to a small extent with respect to the sandwich members 153 and the base frame 151 by adding a larger force than the biasing force of the spring 164.

The base frame 151 and the towing body 152 integrated by the sandwich members 153 are disposed between the pair of bases 154 such that the pins 157A and 157B are engaged with the long holes 161 and the guide holes 162, respectively. In this state, the locking balls 160 are disposed between the locking grooves and the guide grooves, and biased toward the proximal end sides of the locking grooves by the biasing members 159, respectively.

A motion of the first swing section 141 having the above-mentioned configuration is described.

In a state in which the operator is not touching the device, as shown in FIG. 38, since the release screw 156 and the locking ball 160 are spaced slightly apart from each other, the locking ball 160 is biased by the biasing member 159 to move to a position in which the locking ball cuts into the locking groove. Accordingly, since the towing body 152 is fixed with respect to the base 154, the first swing section 141 does not automatically swing.

Figure 42:
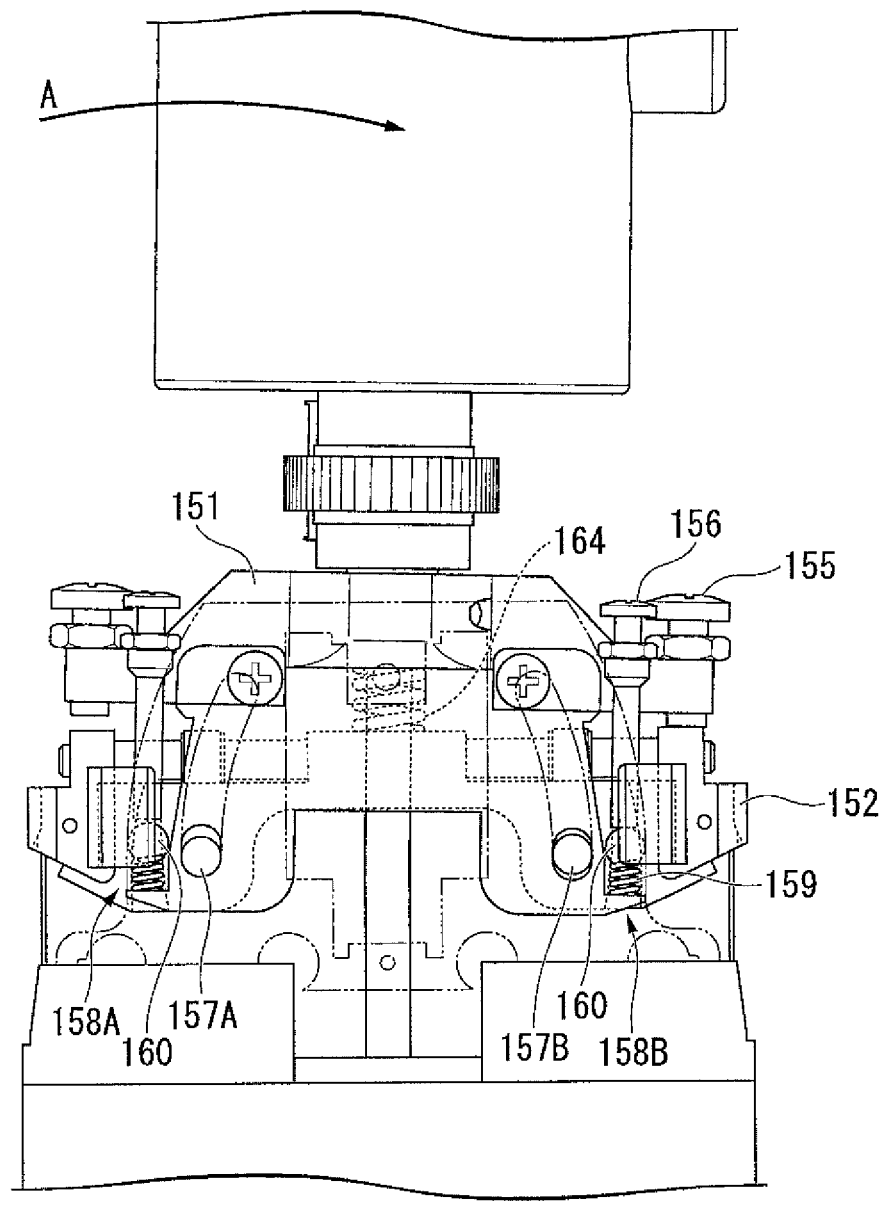
FIG. 42 is a view showing a motion of the first swing section of the third example.

When the operator pulls the stick 131 down in a direction parallel to the first swing surface f1, for example, a direction of an arrow A shown in FIG. 42, the base frame 151 is swung about the pin 157A. As a result, a distal end of the base frame 151 from the pin 157A in the widthwise direction approaches the towing body 152 while compressing the spring 164. Then, first, the release screw 156 comes in contact with the locking ball 160 to resist the biasing member 159 and move the locking ball 160 to a distal end side of a locking groove 158B. Next, the push screw 155 comes in contact with the towing body 152 to press the towing body 152.

As the locking ball 160 is moved, since the locking ball 160 of the pin 157B side does not invade the locking groove 158B, an end of the pin 157B side of the towing body 152 is in a swingable state. Accordingly, as pressed by the push screw 155, the towing body 152 is swung.

Figure 43:
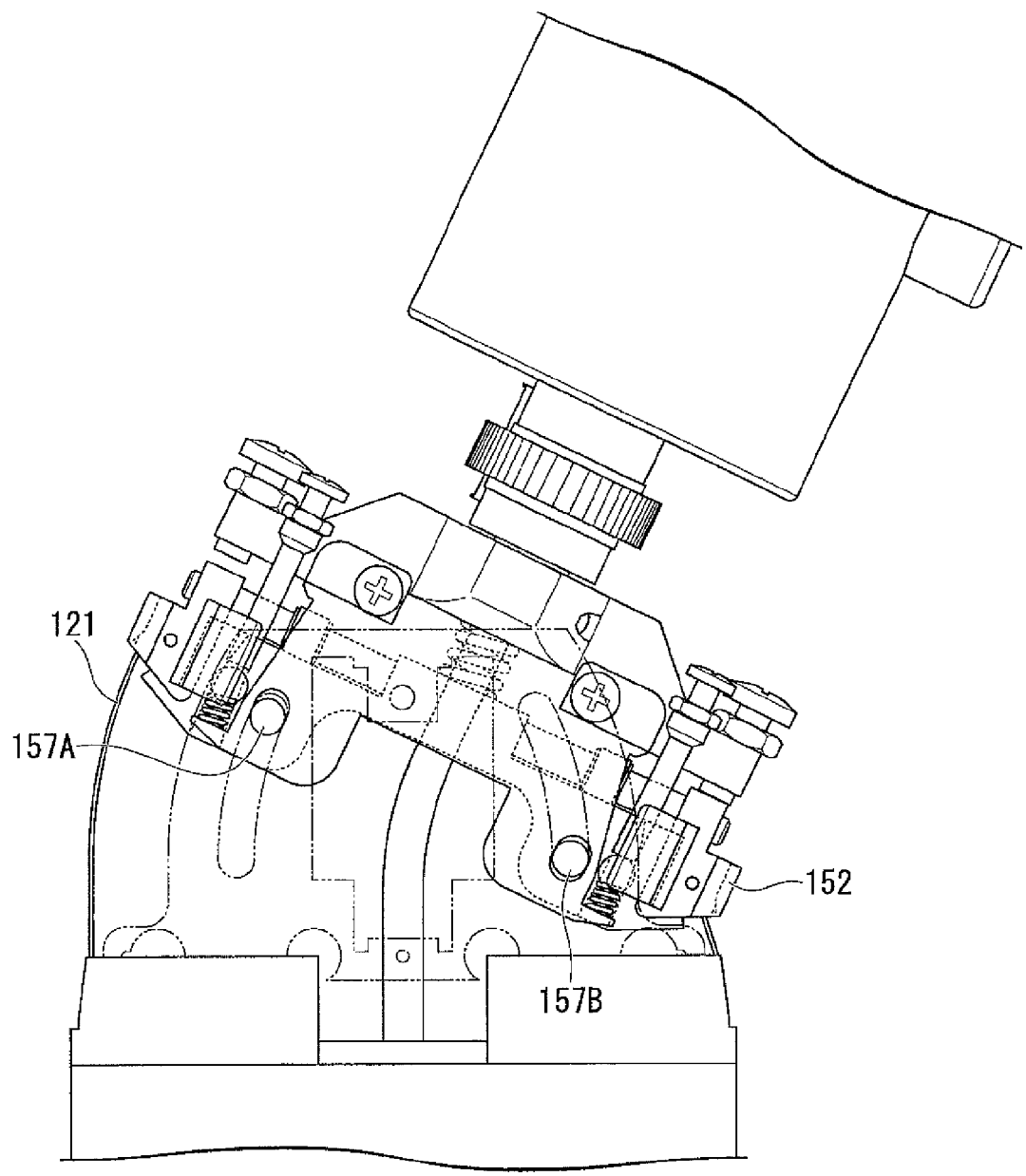
FIG. 43 is a view showing a motion of the first swing section of the third example.

As the end of the pin 157B side of the towing body 152 is swung, at the end of the pin 157A side, a locking groove 158A moves in a direction away from the locking ball 160, and the end of the pin 157A side is also in the swingable state. When the operator further applies a force, as shown in FIG. 43, the towing body 152 is swung about the pin 157B. As a result, the manipulation member 121 of the pin 157A side is towed at a swing diameter larger than in the case in which the towing body 152 is swung about a center in the widthwise direction as a swing center. Accordingly, towing of the manipulation member 121 can be more efficiently performed while performing substantially the same swing manipulation about the center in the widthwise direction as the swing center.

Figure 44:
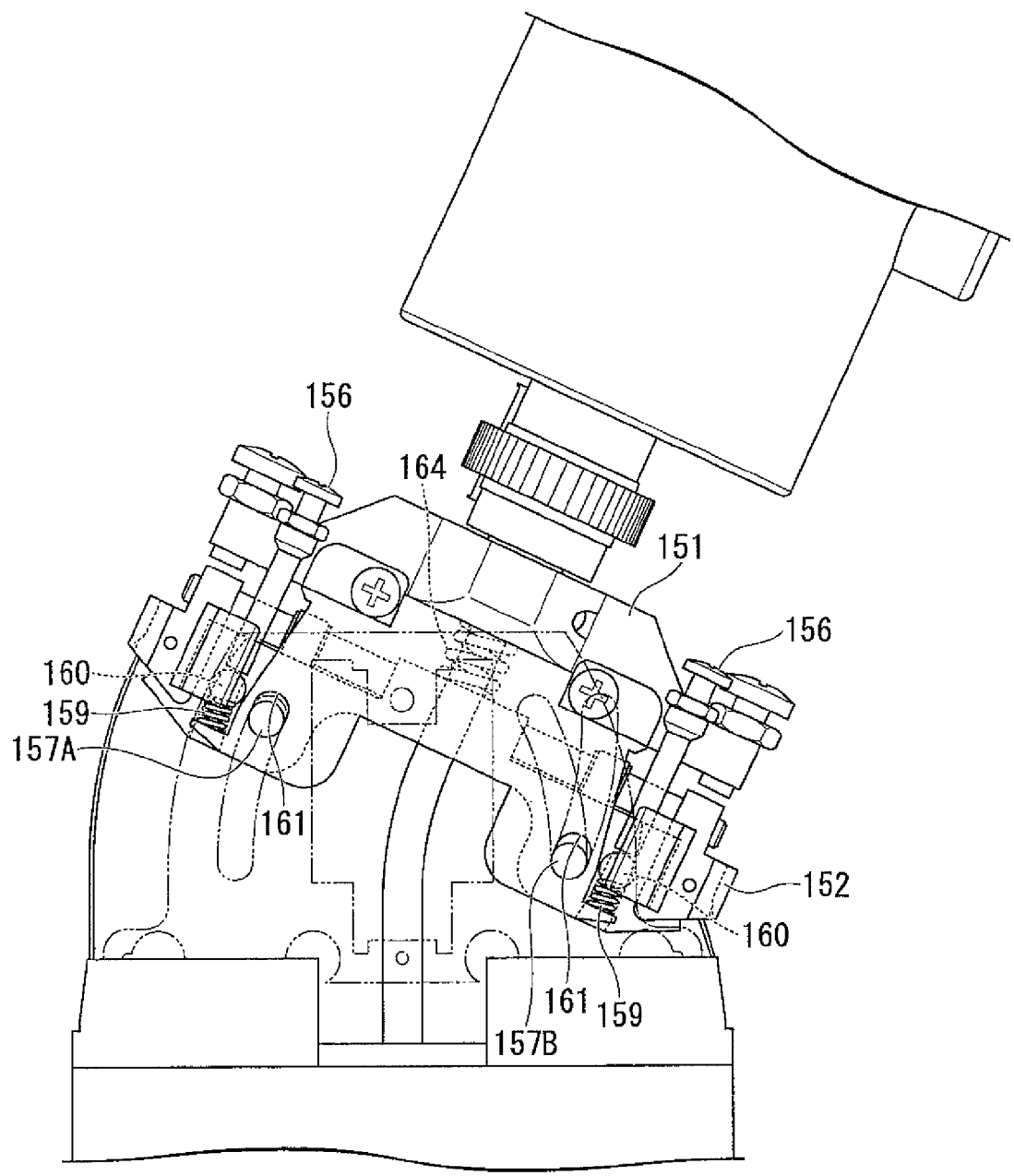
FIG. 44 is a view showing a motion of the first swing section of the third example.

When a force applied to the stick 131 is disappeared by releasing the operator's hands from the stick 131 during the swing manipulation, the towing body 152 is separated from the base frame 151 by action of the spring 164 so that the pins 157A and 157B are pressed against a lower end of the long hole 161. Then, since the release screw 156 is separated from the locking ball 160 as shown in FIG. 44, the locking ball 160 cuts into the locking groove by the biasing member 159, and the swing state of the first swing section 141 is maintained. The swing state of the second swing section 142 is also maintained with the same structure.

In the swing mechanism 140 of the embodiment, an automatic lock mechanism configured to maintain the swing state of the first swing section 141 and the second swing section 142 when a force applied to the stick 131 is absent is composed of the locking grooves 158A and 158B, the biasing member 159, the locking ball 160, and so on. The automatic lock mechanism is installed inside the manipulation member 121 in the widthwise direction of the each swing sections 141 and 142. In the structure disclosed in United States Patent Publication Application No. 2010/0063354, since the mechanism having the same function is installed outside the manipulation member in the widthwise direction of the swing sections, the entire mechanism is apt to be increased. However, according to the swing mechanism 140, further miniaturization is possible.

In addition, as shown in FIG. 38, the first swing section 141 and the second swing section 142 are disposed perpendicular to each other, and pins of the swing sections having a swing center are disposed on the same plane perpendicular to the axis of the manipulation section 130. Accordingly, a dimension of the swing mechanism in the axial direction of the manipulation section 130 can be reduced, and the manipulation feeling of the first swing section 141 can be substantially the same as the manipulation feeling of the second swing section 142.

While the structure disclosed in United States Patent Publication Application No. 2010/0063354 includes the mechanism configured to lock the manipulation state as described above, it is a problem that when the operator's hand unintentionally contacts the stick or the like to apply a force, the stick may be moved by the force. In the swing mechanism 140, the arbitrary locking section 143 is installed and is configured to securely fix (arbitrarily lock) the state of the swing mechanism while resisting an external force such that the stick 131 is not swung even in this case.

Figure 45:
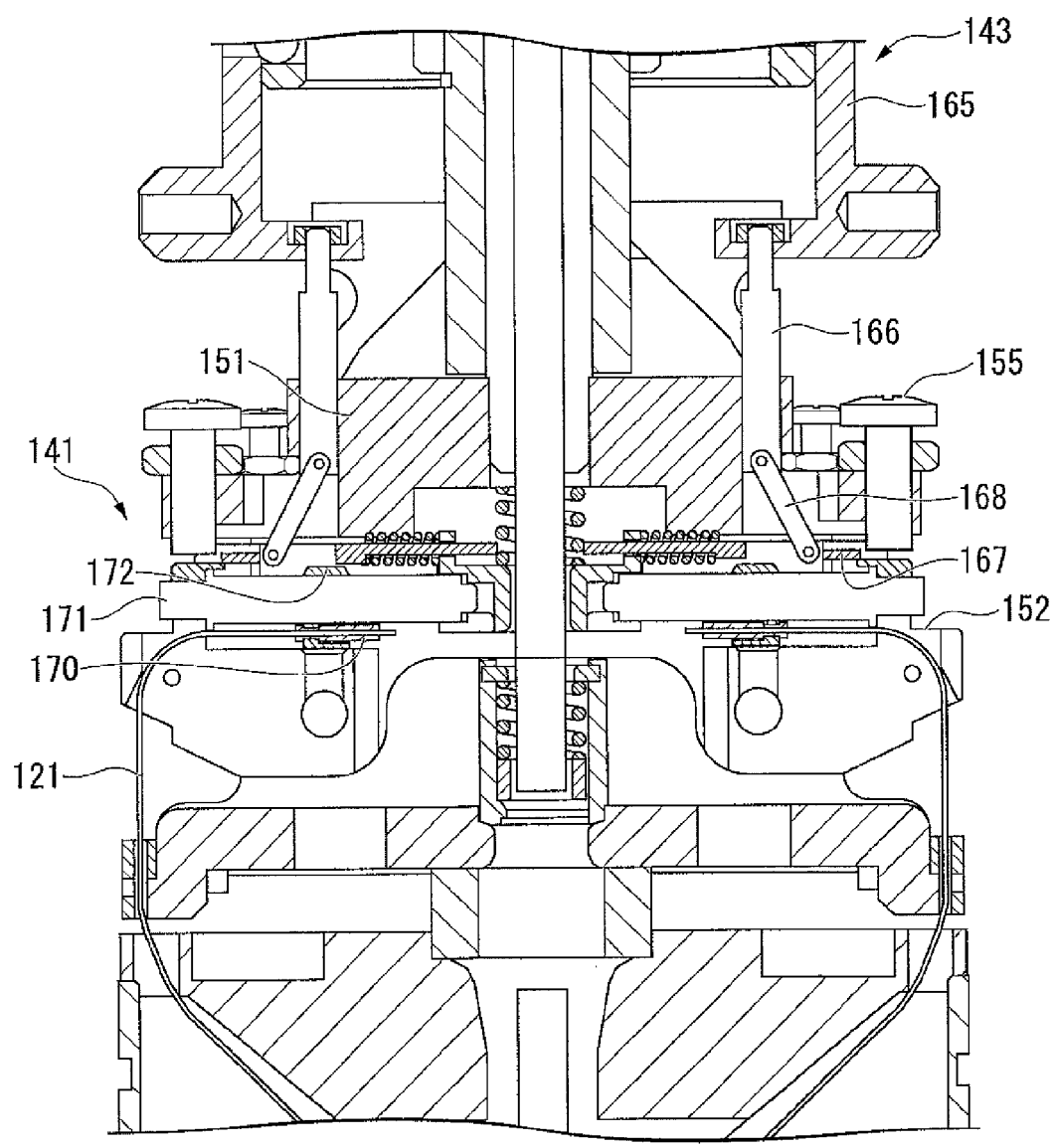
FIG. 45 is a cross-sectional view of a first swing surface of the swing mechanism of the third example.

FIG. 45 is a cross-sectional view of the first swing surface f1 of the first swing section 141. The arbitrary locking section 143 includes a hood 165 installed at an upper side of the first swing section 141, a cylinder 166 inserted into the base frame 151, a spacer 167 disposed to enter between the push screw 155 and the towing body 152, and a link 168 connecting the cylinder 166 to the spacer 167. The hood 165 is connected to the cylinder 166.

Figure 46:
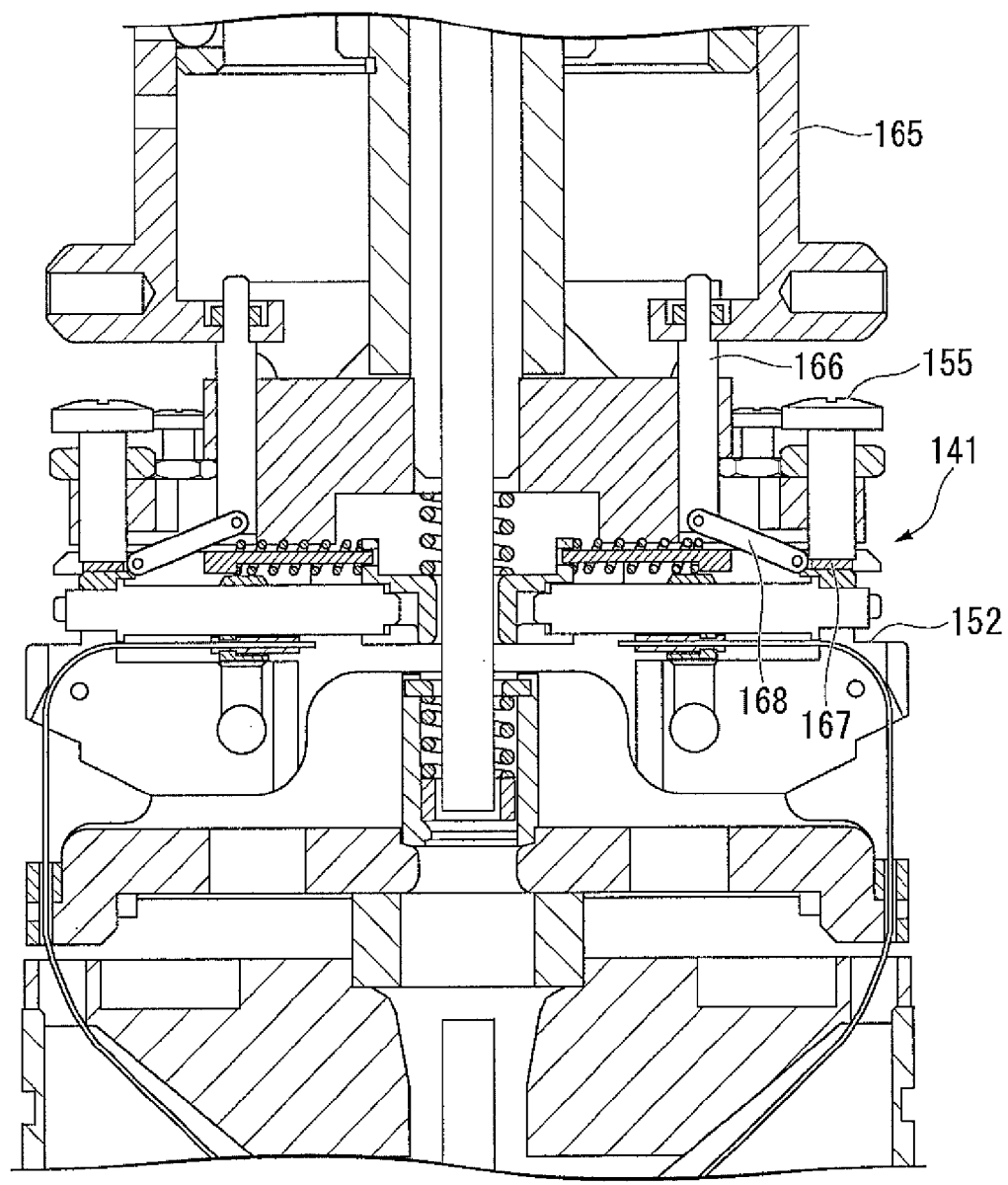
FIG. 46 is a cross-sectional view of a first swing surface of the swing mechanism of the third example.

When the operator slides the hood 165 to approach the first swing section 141, as shown in FIG. 46, the cylinder 166 is pushed into the base frame 151. Then, the spacer 167 enters between the push screw 155 and the towing body 152 by the link 168. As a result, since the release screw 156 does not perform a series of motions of pushing the locking ball 160 out of the locking groove, the stick 131 is fixed not to move even when the external force is applied. FIG. 37 shows a state in which the arbitrary locking section 143 is manipulated, and the spacer 167 enters between the push screw 155 and the towing body 152.

Since the cylinder 166 of the first swing section 141 is connected to the hood 165, even if the first swing section 141 is in any posture, a positional relation between the hood 165 and the base frame 151 is not varied. Meanwhile, in the second swing section 142, since a cylinder section 166a having the same function as the cylinder 166 is not connected to the hood 165, a positional relation between the hood 165 and the base frame 151a is varied by the posture of the first swing section 141. For this reason, in the arbitrary lock mechanism of the second swing section 142, the cylinder section 166a is configured to be pressed by an adjuster 169 attached to the hood 165.

The adjuster 169 is disposed on the upper side of the cylinder section 166a, substantially parallel to the widthwise direction of the first swing section 141. The adjuster 169 has a first arc section 169A extending to the pin 157A side and a second arc section 169B extending to the pin 157B side. The first arc section 169A has an arc shape centered at an axis of the pin 157B, and the second arc section 169B has an arc shape centered at an axis of the pin 157A. For this reason, the shortest distance between a lower surface of the adjuster 169 and a distal end of the cylinder section 166a is varied very little by the posture of the first swing section 141. Accordingly, as the operator slides the hood 165 and the lower surface of the adjuster 169 comes in contact with the cylinder section 166a, the cylinder section 166a can be appropriately pressed to arbitrarily lock the state of the second swing section 142 regardless of the posture of the first swing section 141.

The other characteristics of the swing mechanism 140 are described.

As shown in FIG. 45, a stopper 170 is attached to an end of the manipulation member 121, and a dimension in the radial direction is increased. An adjustment screw 171 is rotatably attached to an upper portion of the towing body 152 to be parallel to the widthwise direction of the towing body 152, and a fixing member 172 which the stopper 170 is engaged with and fixed to is screw-fitted to the adjustment screw 171. A cross-section of the stopper 170 has a shape of a large diameter section and a small diameter section, and an engagement hole (not shown) having a large diameter section and a small diameter section and into which the stopper 170 can be inserted is formed in the fixing member 172. Since the small diameter section of the engagement hole is shorter than the large diameter section of the stopper 170, as the manipulation member 121 is rotated about the axis after insertion of the stopper 170, the manipulation member 121 can be easily engaged with and fixed to the fixing member 172.

In addition, as shown in FIG. 45 and FIG. 37, since the end of the adjustment screw 171 is exposed, the positional relation between the adjustment screw 171 and the fixing member 172 can be varied and fine adjustment of the length of the manipulation member 121 can be performed by rotating the adjustment screw 171 using a driver or the like.

Further, the swing mechanism 140 can rotate about the axis of the insertion section 110 with respect to the insertion section 110 within a certain range. Accordingly, fine adjustment can be performed by fitting a bending direction of the active bending section 115 to the first swing surface f1 and the second swing surface f2.

The positional relation after the adjustment can be fixed and released by a screw 173 (see FIG. 2).

(Treatment Instrument)

Next, a configuration of the treatment instrument that can be appropriately used in the endoscope 1 is described. The most remarkable feature of the treatment instrument of the embodiment is to provide a grip that can be fitted onto the stick 131 of the manipulation section 130.

Figure 47:
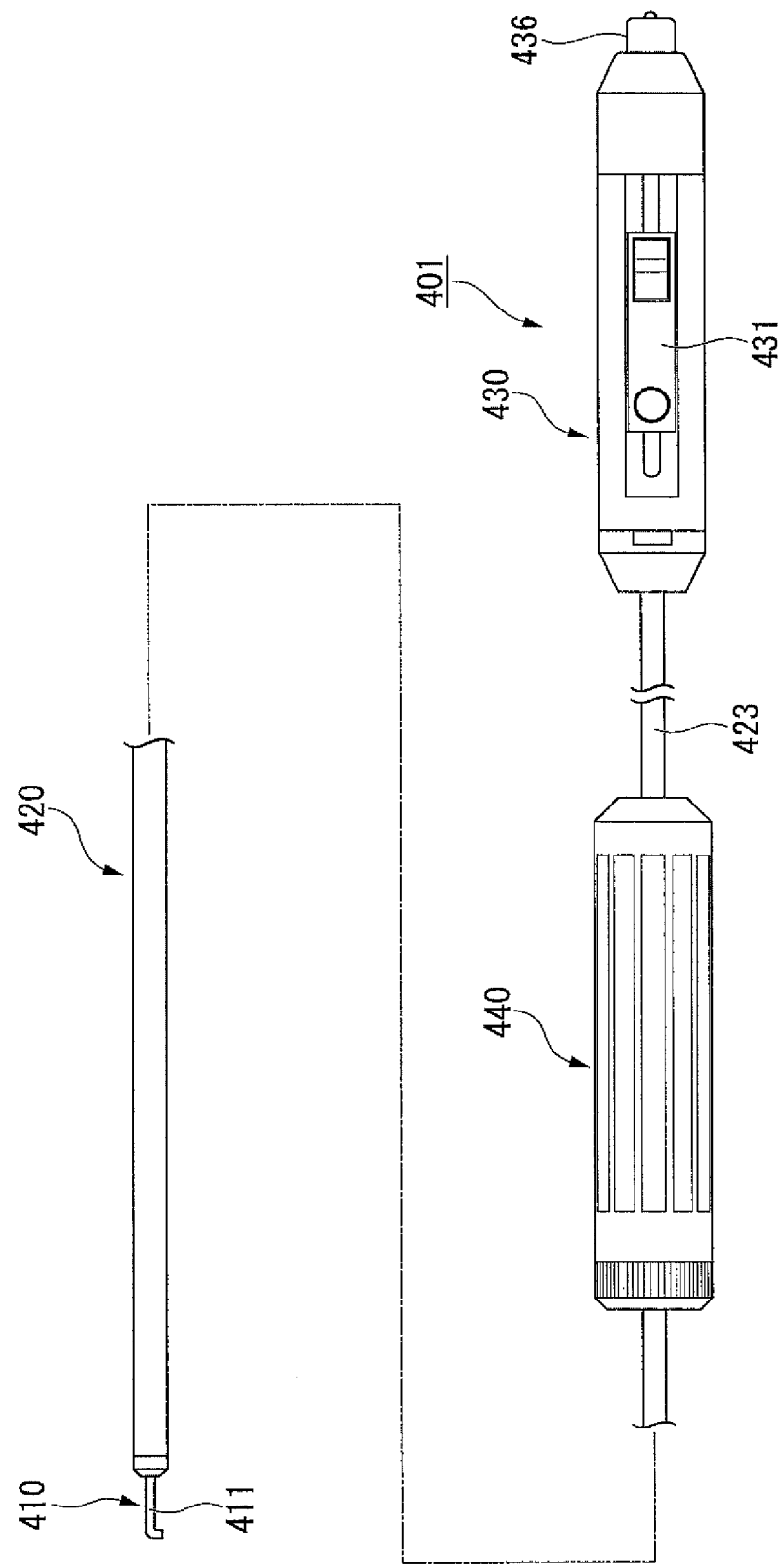
FIG. 47 is a view of a treatment instrument of the first example of the present invention.

FIG. 47 is a view showing a treatment instrument 401 of the first example of the embodiment. The treatment instrument 401 includes a treatment unit 410 configured to perform treatment with respect to a living body, a soft sheath 420 having flexibility, a manipulation section 430 configured to manipulate the treatment unit 410, and a grip 440 formed between the treatment unit 410 and the manipulation section 430.

In FIG. 47, while a treatment unit having a knife 411, which is energized and used, is shown as an example of the treatment unit 410, various treatment units of a known treatment instrument for an endoscope (described later) can be applied. Known various flexible sheaths can be also applied to the soft sheath 420.

The manipulation section 430 is connected to the treatment unit 410 by the manipulation wire (not shown) inserted into the soft sheath 420, and the treatment unit 410 can protrude from and retract into the distal end of the soft sheath 420. A specific configuration of the manipulation section 430 can be selected from known various structures according to the treatment unit 410. The manipulation section 430 of the first example includes a slider 431 configured to cause the treatment unit 410 to protrude and retract, and a power feed unit 436 connected to a power supply (not shown).

Figure 48:
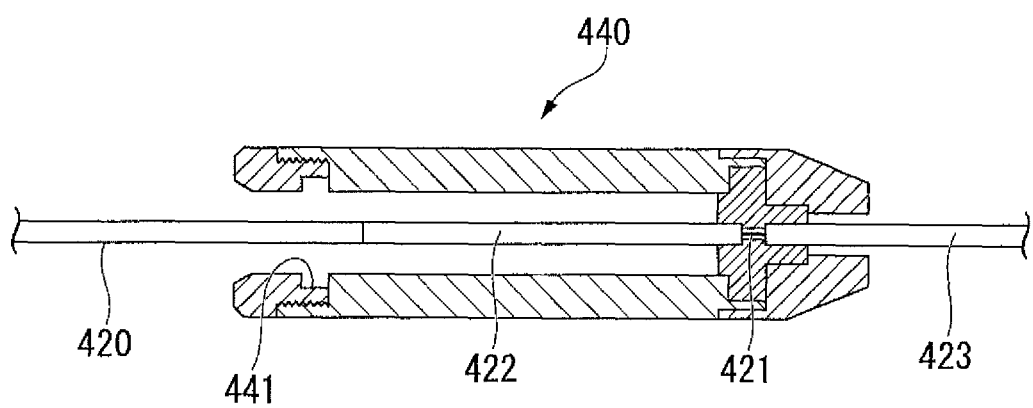
FIG. 48 is a cross-sectional view showing a grip of the treatment instrument of the first example of the present invention.

FIG. 48 is a cross-sectional view of the grip 440. The grip 440 has a certain stiffness and substantially a cylindrical shape, and an engagement groove 441 engaged with a lock claw (described later) installed at the stick 131 of the manipulation section 130 is formed in the inner surface of the grip in the circumferential direction.

A manipulation wire 421 is inserted into the inner cavity of the grip 440. The proximal end of the soft sheath 420 into which the manipulation wire 421 is inserted is disposed in the inner cavity of the grip 440. The manipulation wire 421 is inserted into a hard sheath 422 formed of a metal pipe or the like, at the proximal end side, rather than the soft sheath 420. The proximal end of the hard sheath 422 is fixed with respect to the grip 440. A gap between a wall surface of a grip inner cavity, and the soft sheath 420 and the hard sheath 422 is set such that the stick 131 can enter and smoothly advance and retract.

The grip 440 and the manipulation section 430 are connected to each other via a soft tube 423. As the tube 423, the same material as the soft sheath 420 may be used.

A motion in use of the treatment instrument 401 having the above-mentioned configuration is described. The operator inserts the treatment unit 410 from the proximal end of the stick 131 of the manipulation section 130 and moves the treatment unit 410 into the treatment instrument channel 111 in communication with the inner cavity of the stick 131.

Then, the grip 440 is fitted onto the stick 131 such that an outer circumferential surface of the stick 131 is covered with the grip 440.

Figure 49:
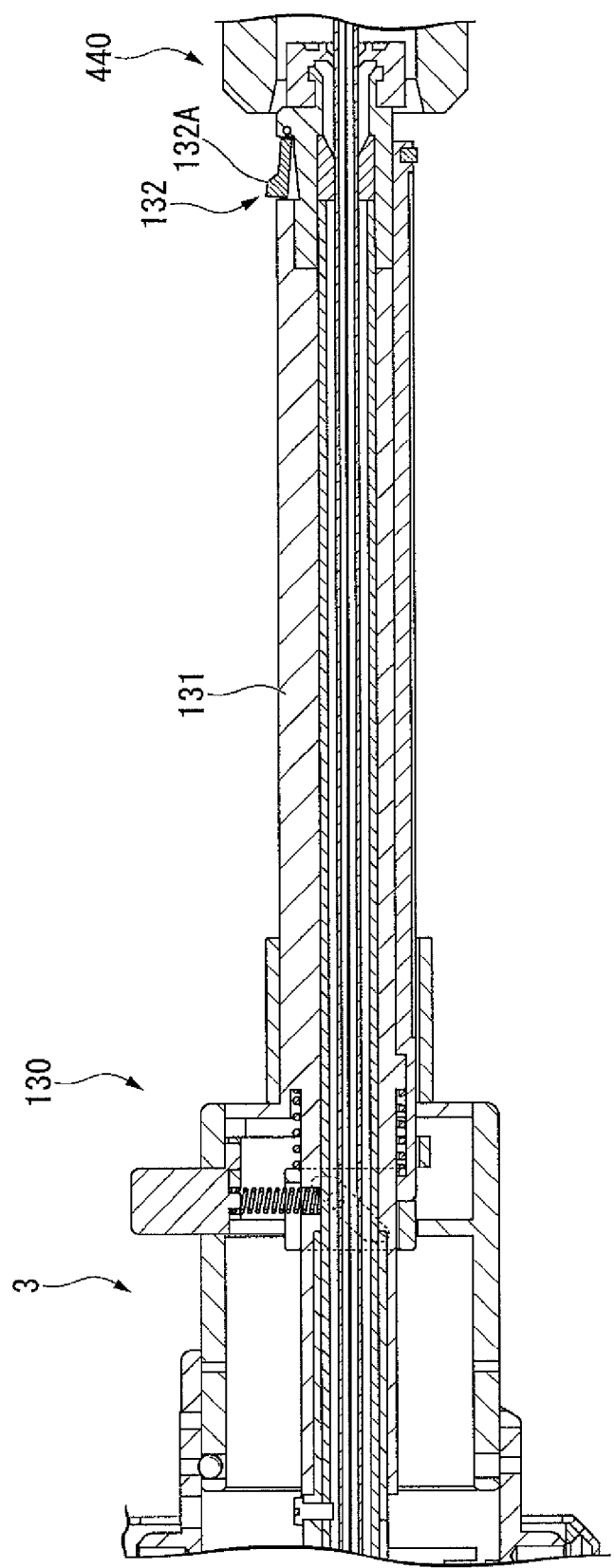
FIG. 49 is a cross-sectional view showing a grip of the treatment instrument and a stick of the right arm section of the first example of the present invention.

As shown in FIG. 49, a lock claw 132 protrudes from the outer circumferential surface of the proximal end side of the stick 131. The lock claw 132 rotates along the outer circumferential surface of the stick 131 as an inclined surface 132A of the proximal end side is pressed by the grip 440. For this reason, the grip 440 can be fitted thereonto.

When the treatment unit 410 protrudes from the distal end of the treatment instrument channel 111, the operator holds the grip 440 and performs the manipulation of the treatment instrument 401. As the grip 440 is rotated with respect to the stick 131, the entire treatment instrument 401 can be rotated to adjust the direction of the treatment unit 410. As the grip 440 is moved to advance and retract with respect to the stick 131, the entire treatment instrument 401 can be moved to advance and retract with respect to the right arm section 3. A protruding and retracting manipulation of the treatment unit 410 from the soft sheath 420 by the manipulation section 430 is performed by an assistant as necessary.

Figure 50:
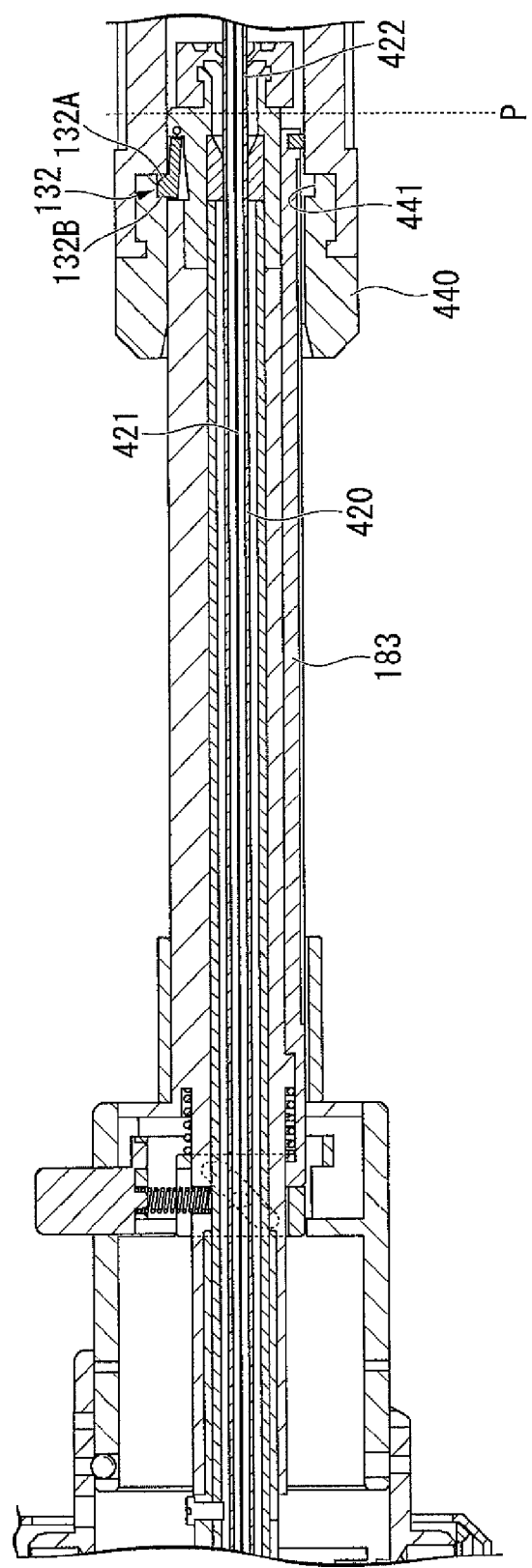
FIG. 50 is a cross-sectional view showing the grip of the treatment instrument and the stick of the right arm section of the first example of the present invention.

An inclined surface 132B of the distal end side of the lock claw 132 is steeper than the inclined surface 132A of the proximal end side with respect to the outer circumferential surface of the stick 131. For this reason, even when the operator mistakenly moves the grip 440 rearward by too much, as shown in FIG. 50, the grip 440 does not get over the lock claw 132 engaged with the engagement groove 441, and a drop of the grip 440 from the stick 131 during the procedure is appropriately suppressed.

A distal end position P of the hard sheath 422 is set such that at least a portion of the hard sheath 422 is disposed in the inner cavity of the stick 131 when the lock claw 132 is engaged with the engagement groove 441.

Figure 51:
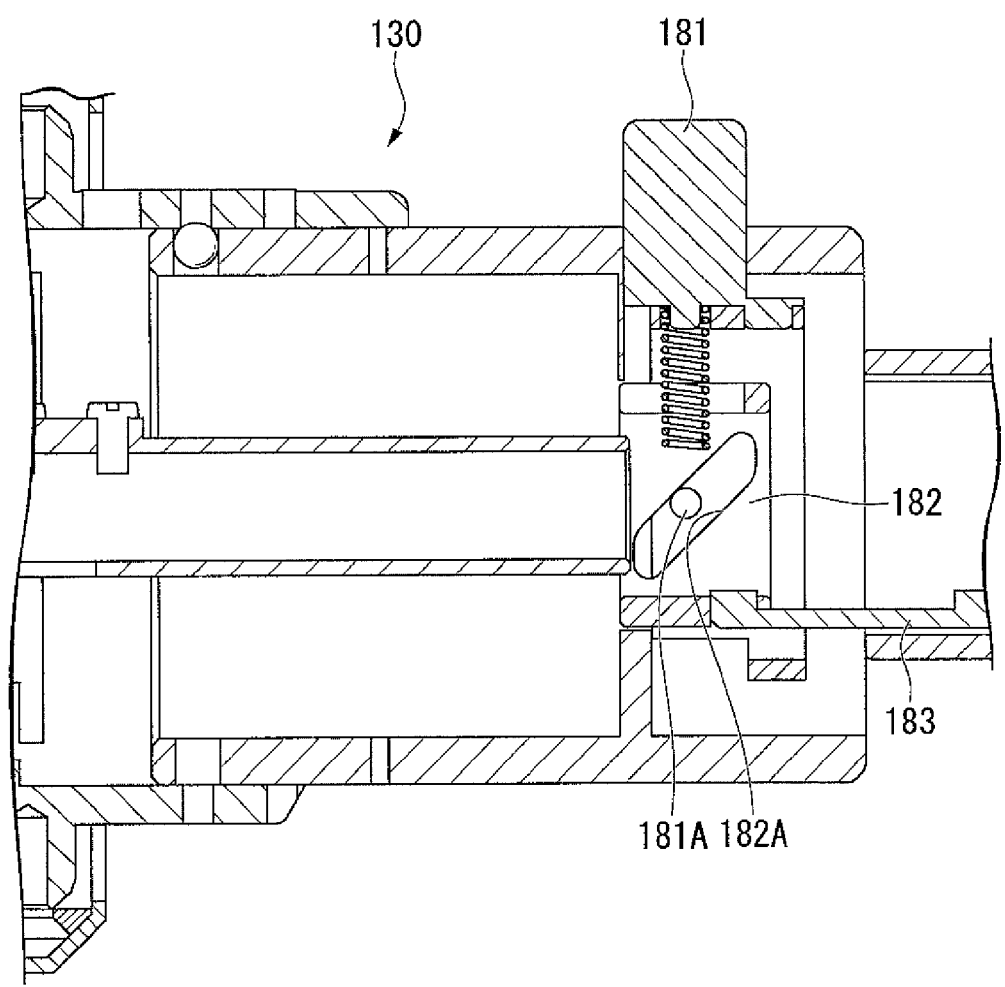
FIG. 51 is a cross-sectional view showing a portion of the manipulation section of the right arm section.
Figure 52:
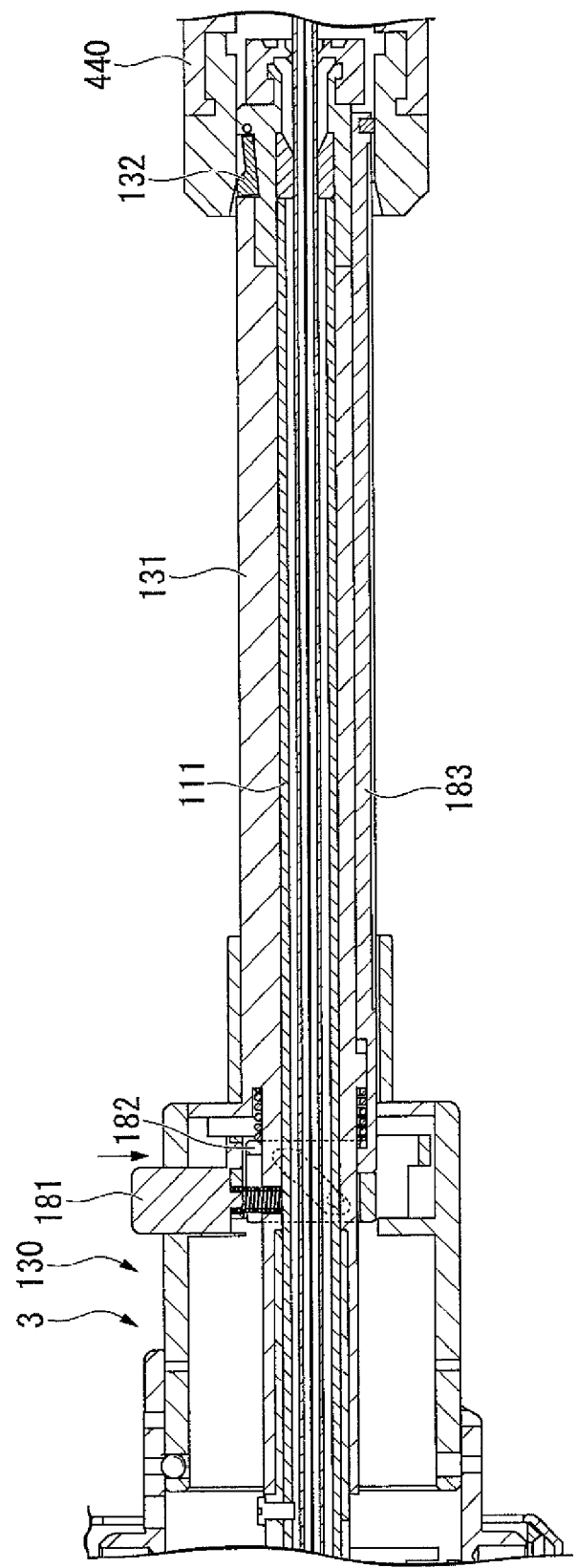
FIG. 52 is a cross-sectional view showing the grip of the right arm section and the stick of the right arm section.

After completion of the procedure, when the treatment instrument 401 is removed from the right arm section 3, a button 181 installed at the manipulation section 130 is pressed. In FIG. 51, in the manipulation section 130, surroundings of the button 181 are shown except for the treatment instrument channel 111 and so on. As a cam pin 181A installed at the button 181 moves in a cam groove 182A formed in a cam slider 182, the cam slider 182 is moved to the proximal end side. A rod 183 is connected to the cam slider 182. As shown in FIG. 52, the rod 183 extends to the vicinity of the proximal end of the stick 131 along the stick 131, and is connected to the lock claw 132. When the cam slider 182 is moved to the proximal end side, the rod 183 is also moved to the proximal end side. As a result, the lock claw 132 is swung to move to a position at which the lock claw 132 does not protrude from the outer circumferential surface of the stick 131, and the grip 440 can be removed.

United States Patent Publication Application No. 2010/0063354 discloses that a conventional known treatment instrument for an endoscope is inserted into the arm manipulation section of the medical instrument and a procedure is performed. In this case, while the stick of the manipulation section is held when the arm is bent, when advancing and retracting or rotation manipulation of the treatment instrument is performed, it is necessary to hold the manipulation section of the treatment instrument, and therefore the manipulation becomes a problem which is complex.

While it is possible to hold the manipulation section of the treatment instrument and perform the bending manipulation of the arm, in this case, a bending load may be easily applied to an area disposed in the vicinity of the proximal end opening of the stick of the treatment instrument, and the treatment instrument may be damaged. Further, a position of the hand may be separated from the swing mechanism, and the positional relation with respect to the endoscope manipulation section may be varied to decrease the entire manipulation performance.

According to the treatment instrument 401 of the first example, since the grip 440 that can be fitted onto the stick 131 is provided, both of the bending manipulation of the active bending section 115 and the advancing/retracting and rotation manipulations of the treatment instrument 401 can be easily performed by gripping the grip 440.

In addition, since the lock claw 132 is installed at the stick 131 and the engagement groove 441 engaged with the lock claw is installed at the grip 440, the grip 440 is not removed from the stick 131 during the procedure, and the manipulation is easy.

Further, when the hard sheath 422 is disposed in the grip 440 and the lock claw 132 is engaged with the engagement groove 441, at least a portion of the hard sheath 422 is disposed in the inner cavity of the stick 131. That is, during the advancing and retracting manipulation of the grip 440, a state in which a portion of the hard sheath 422 is inserted into the stick 131 is always maintained. Accordingly, the sheath is not bent in the grip 440, and force of the advancing and retracting manipulation can be surely transmitted to the distal end side of the treatment instrument 401. In addition, even when the treatment instrument 401 is inclined with respect to the stick 131, the resistance during the advancing and retracting manipulation does not excessively increase, and the advancing and retracting manipulation can be smoothly performed.

Figure 53:
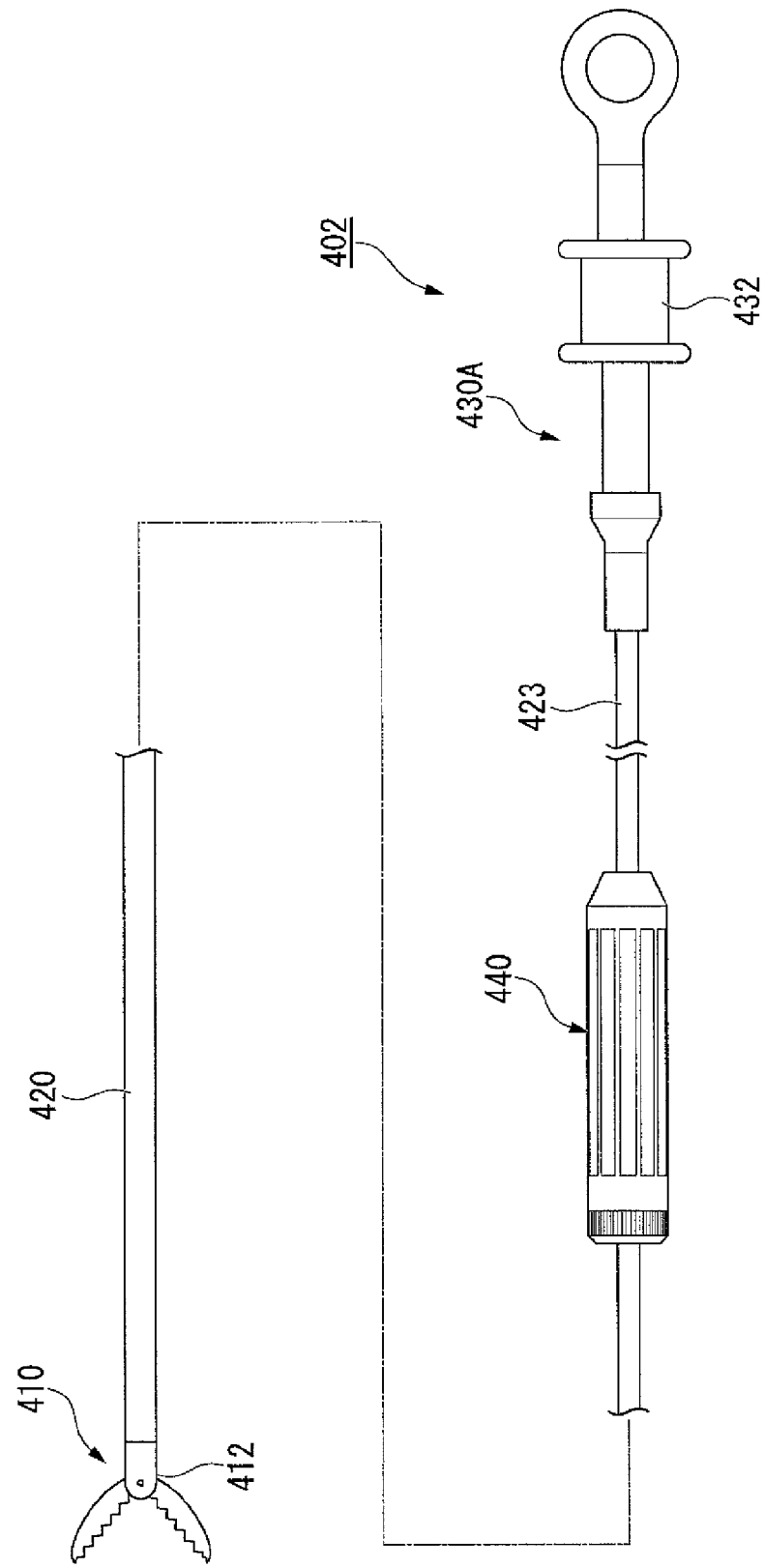
FIG. 53 is a view showing a treatment instrument of the second example of the present invention.

A treatment instrument 402 of a second example shown in FIG. 53 has a forceps section 412 including a pair of forceps pieces disposed in the treatment unit 410, instead of the knife 411. The manipulation section 430A has a finger-grip type slider 432 according to a configuration of the treatment unit 410. As seen above, in the treatment unit and the manipulation section, known various configurations can be appropriately selected according to the target procedure or the like.

Figure 54:
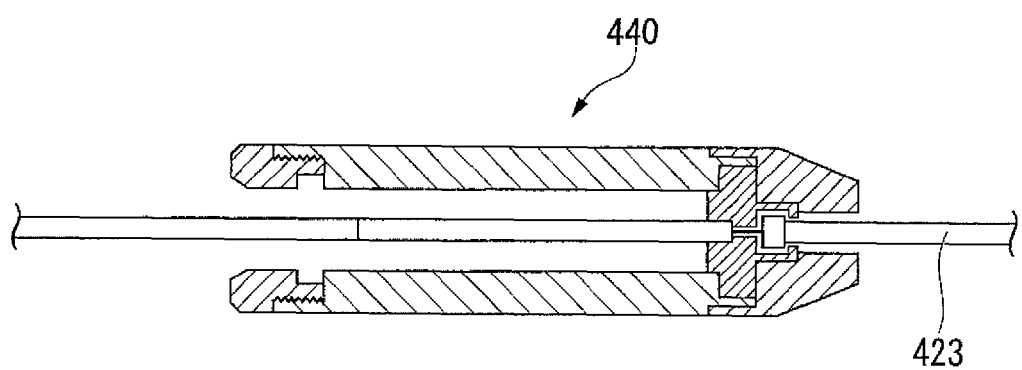
FIG. 54 is a cross-sectional view showing a grip of a treatment instrument of a modified example of the present invention.

In the treatment instrument of the first example and the second example, like a modified example shown in FIG. 54, the distal end of the tube 423 may be rotatably connected to the grip 440. As a result, since the rotation manipulation of the grip 440 by the operator is not transmitted to the tube 423 or the manipulation section of the treatment instrument, interference with manipulation of the assistant can be prevented.

Figure 55:
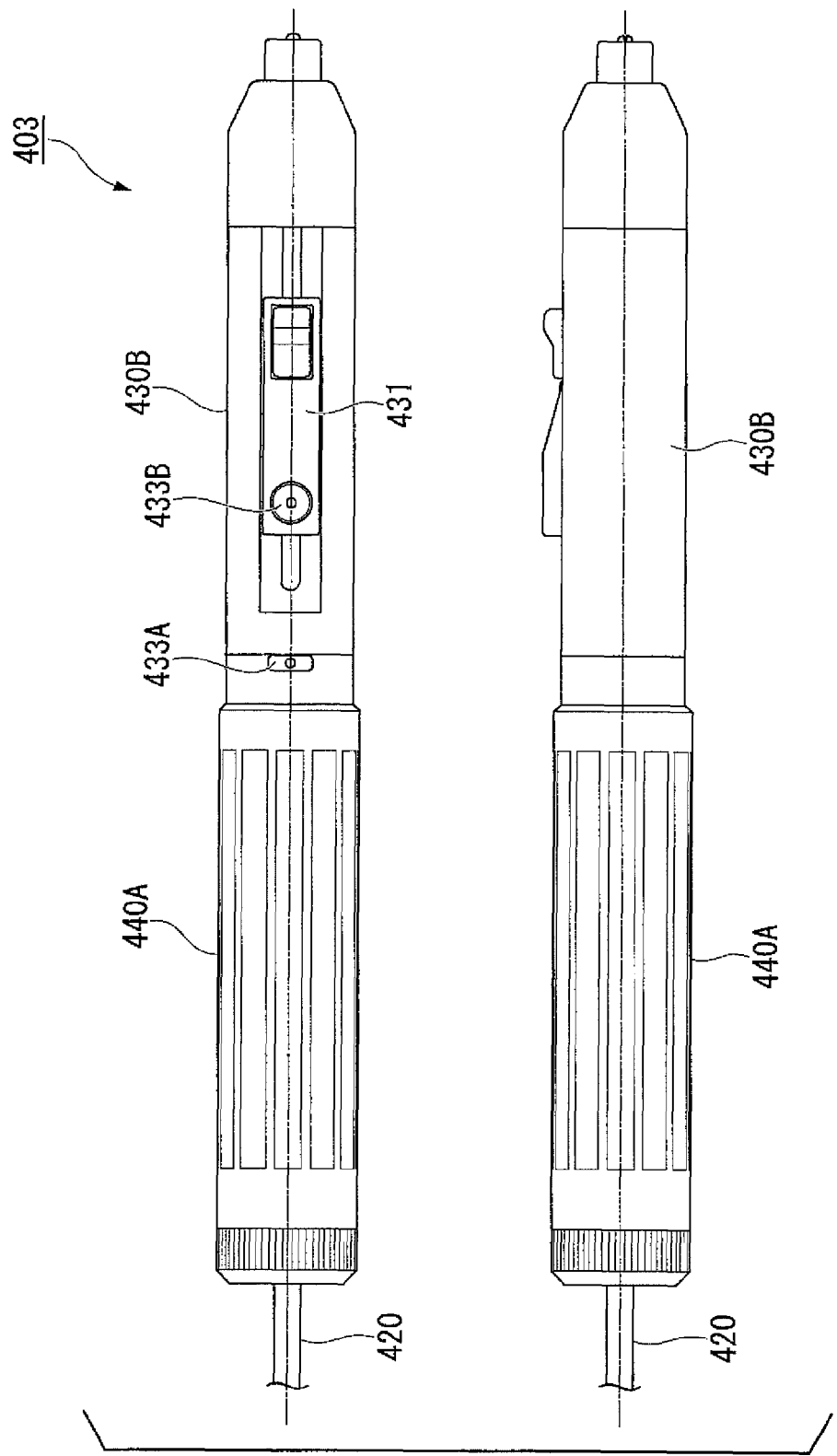
FIG. 55 is a view showing a grip and a manipulation section of a treatment instrument of the third example of the present invention.

FIG. 55 is a view showing a grip 440A and a manipulation section 430B of a treatment instrument 403 of a third example. In the treatment instrument 403, since the configuration of the distal end side rather than the grip 440 is the same as that of the treatment instrument 401, an illustration thereof is omitted here. Unlike the first example, the grip 440 and the manipulation section 430B are directly connected to each other without using the tube 423. In addition, the hard sheath 422 (not shown) is not fixed to the grip 440A, and is detachably engaged with the manipulation section 430B.

In the treatment instrument 403, as two buttons of a first button 433A and a second button 433B installed at the manipulation section 430B are pressed, the treatment unit can be separated from the grip 440A and the manipulation section 430B. The first button 433A configured to disengage the hard sheath 422 from the manipulation section 430B is installed at the distal end side of the manipulation section 430B, and the second button 433B configured to disengage the manipulation wire 421 from the slider 431 is installed at the slider 431. As shown in FIG. 55, both of the first button 433A and the second button 433B are formed at an outer surface of manipulation section 430A and an outer surface of the slider 431, respectively, not to protrude therefrom, such that the buttons are not pressed during the procedure by mistake.

Figure 56:
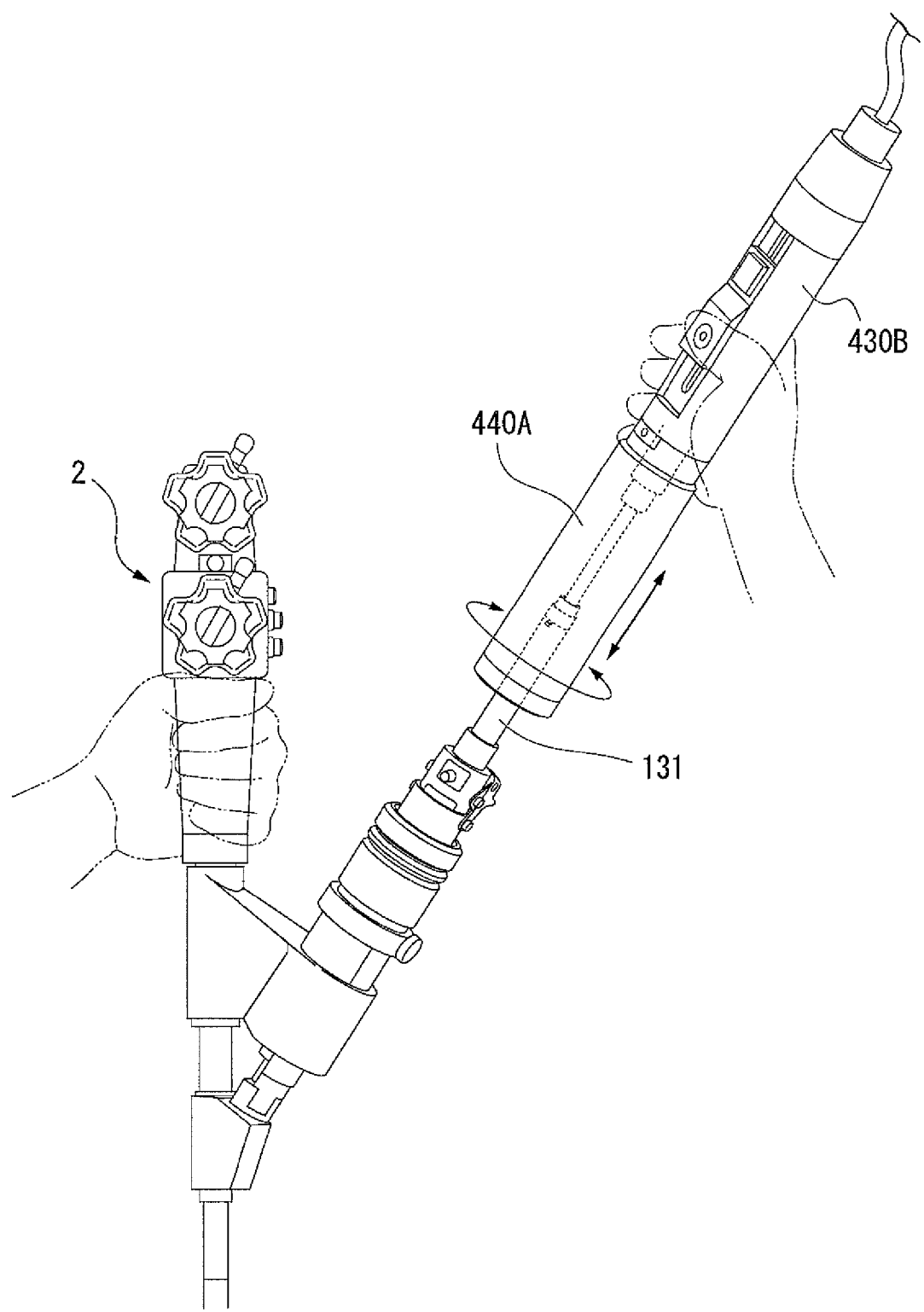
FIG. 56 is a view showing a motion in use of the treatment instrument of the third example of the present invention.

When the treatment instrument 403 is used, after the grip 440A is fitted onto the stick 131, as shown in FIG. 56, the manipulation section 430B can be gripped to perform the advancing/retracting and rotation manipulations. Since the grip 440A and the manipulation section 430B are integrally connected to each other and have a certain stiffness, very little bending load is applied to the soft sheath 420 or the hard sheath 422 inserted into the stick 131. Accordingly, since the operator can perform the bending manipulation of the active bending section 115, the advancing/retracting and rotation manipulation of the treatment instrument 403, and the protruding and retracting manipulation of the treatment unit 410, while holding the manipulation section 430B, the operator can appropriately perform the manipulation by oneself without the need of the assistant.

In addition, as described in the entire configuration, the right arm section 3 can advance and retract with respect to the overtube 2. The advancing and retracting manipulation is performed by moving the manipulation section 130 to advance and retract along the axis. Meanwhile, the advancing and retracting of the treatment instrument is also performed by moving the grip 440A to advance and retract along the axis of the manipulation section 130. Since both the advancing and retracting manipulations are performed on the same axis, the operator can perform exchange of the manipulation section 130 and the grip 440A with no confusion.

Figure 57:
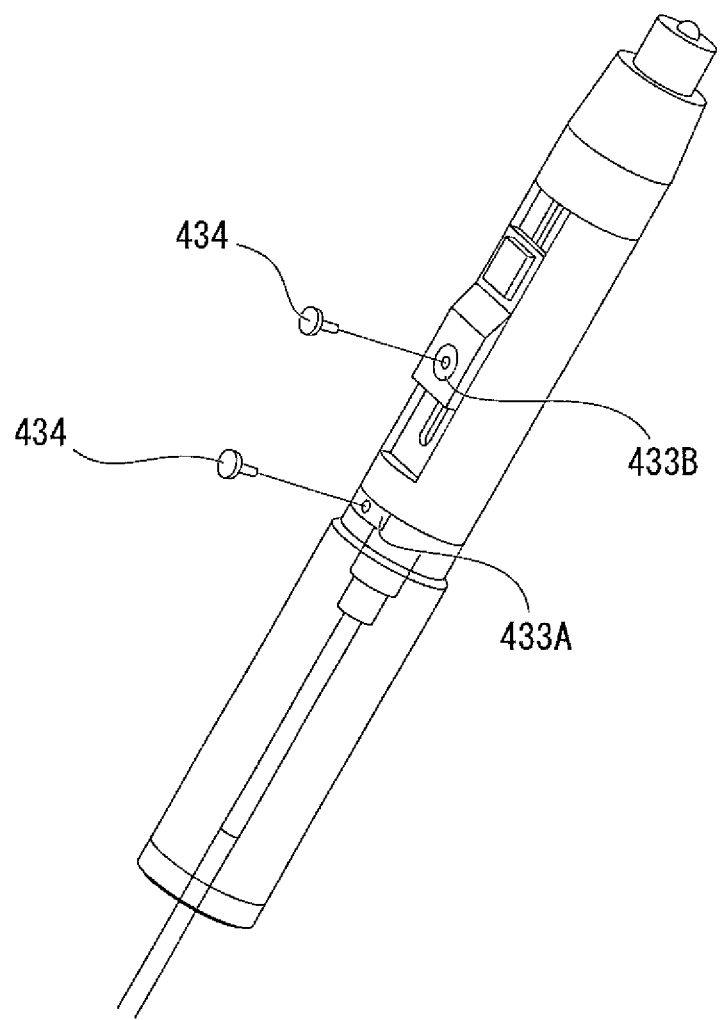
FIG. 57 is a view showing an example of a pushing tool mounted on the treatment instrument of the third example of the present invention.
Figure 58:
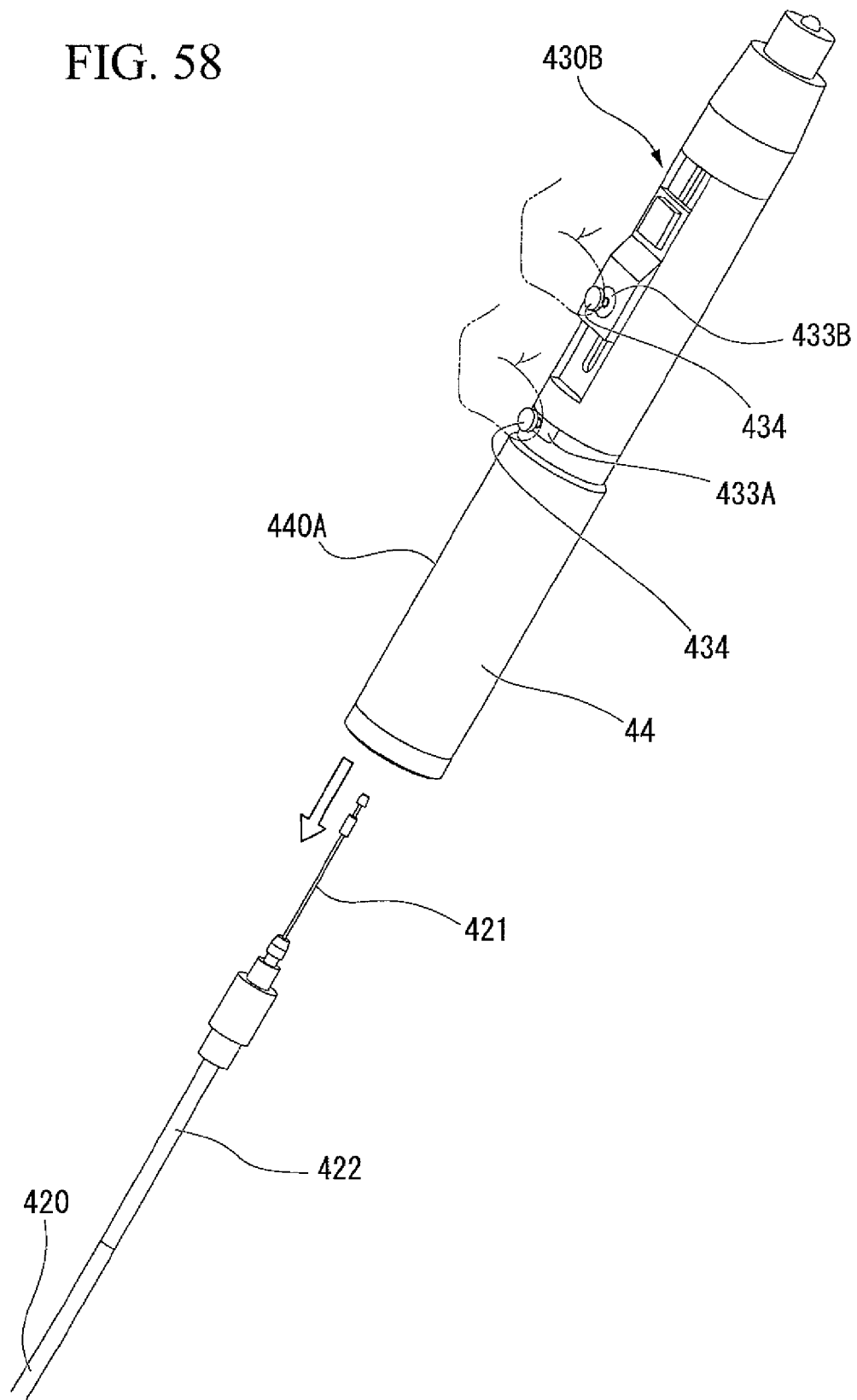
FIG. 58 is a view showing a motion in use of the treatment instrument of the third example of the present invention.

When the hard sheath 422 and the manipulation section 430B are separated from each other, pushing tools 434 as shown in FIG. 57 are mounted on the first button 433A and the second button 433B. As shown in FIG. 58, when the pushing tool 434 is pressed to push the first button 433A and the second button 433B, a region of the distal end side including the treatment unit 410 rather than the hard sheath 422 and the manipulation wire 421 can be separated from the grip 440A and the manipulation section 430B. Accordingly, the distal end side of the treatment instrument can be replaced with a treatment unit having a different configuration, or the distal end side of the treatment instrument can be replaced with a disposable new one or can be disassembled and cleaned.

Figure 59:
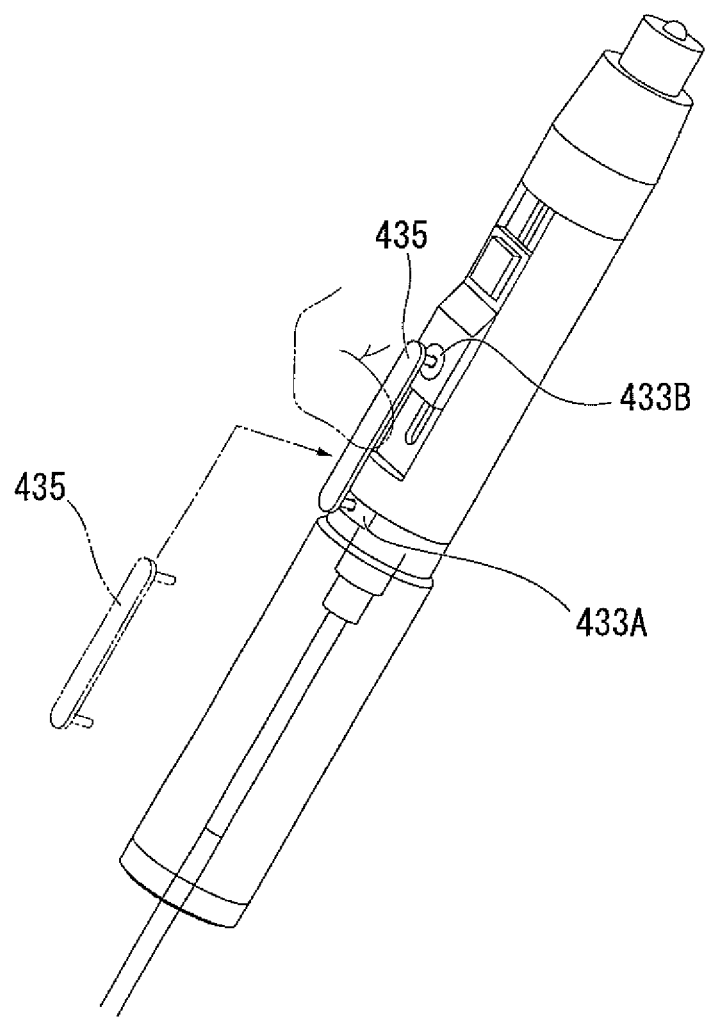
FIG. 59 is a view showing a motion in use of the treatment instrument of the third example of the present invention.

Instead of the two pushing tools 434, as shown in FIG. 59, one pushing tool 435 configured to push the first button 433A and the second button 433B can be used. As a result, separation manipulation becomes easier.

Figure 60:
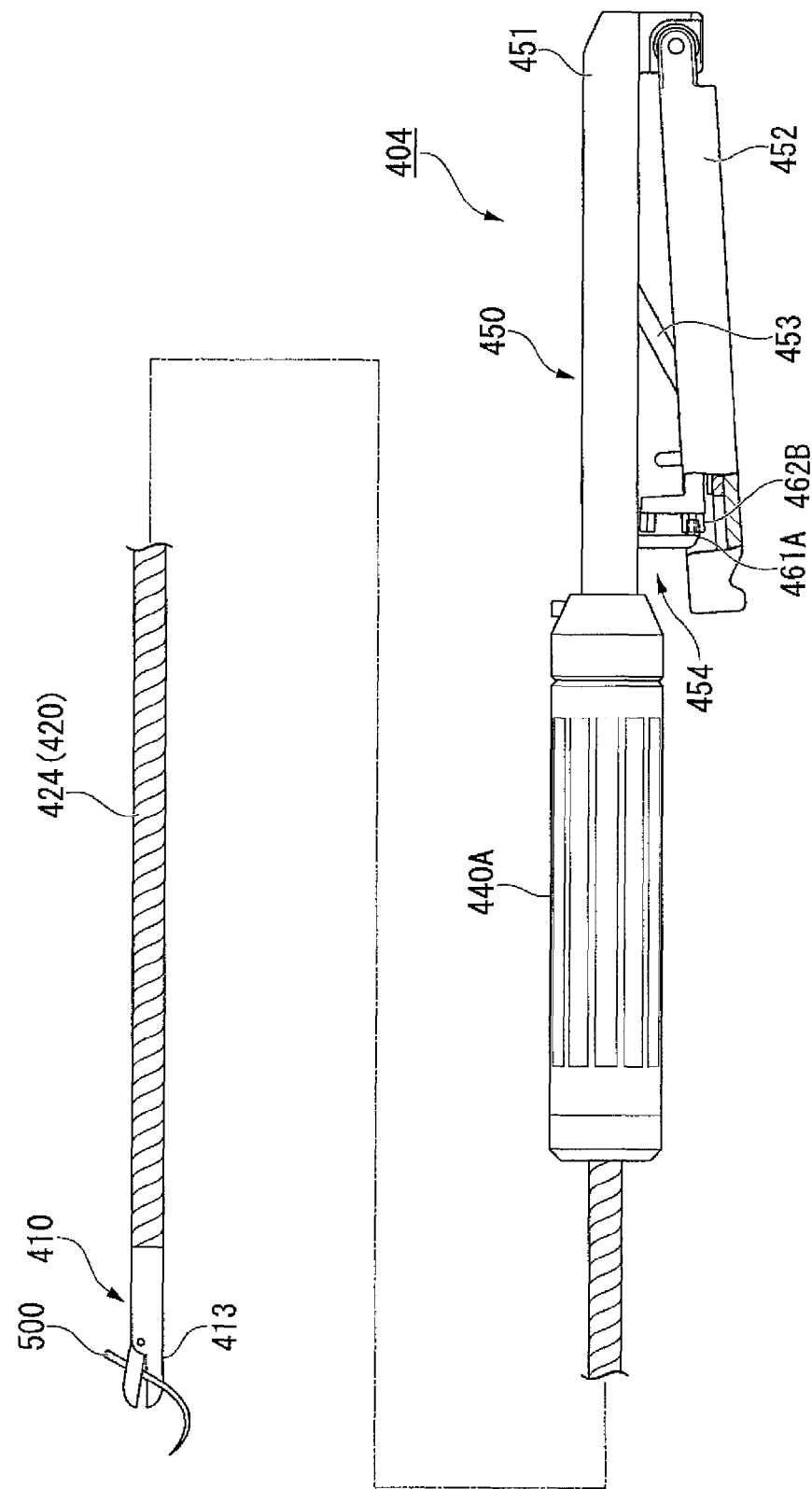
FIG. 60 is a view showing a treatment instrument of the fourth example of the present invention.

FIG. 60 is a view showing a treatment instrument 404 of a fourth example. In the treatment instrument 404, the treatment unit 410 has a forceps section 413 of a one-side open type in which only one of the forceps pieces rotates, and the forceps section 413 is configured to be a needle holder to hold a curved needle 500 or the like. In addition, a known coil sheath 424 is used as the soft sheath 420.

A manipulation section 450 of the treatment instrument 404 includes a first holding section 451, a second holding section 452 having a proximal end section rotatably attached to the proximal end section of the first holding section 451, a link 453 configured to connect the first holding section 451 with the second holding section 452, and a ratchet section 454 configured to maintain the positional relation between the first holding section 451 and the second holding section 452. Since the first holding section 451 is directly connected to the grip 440A, similar to the treatment instrument 403, the operator can grip the manipulation section 450 to perform the advancing/retracting and rotation manipulations of the treatment instrument 404.

Figure 61:
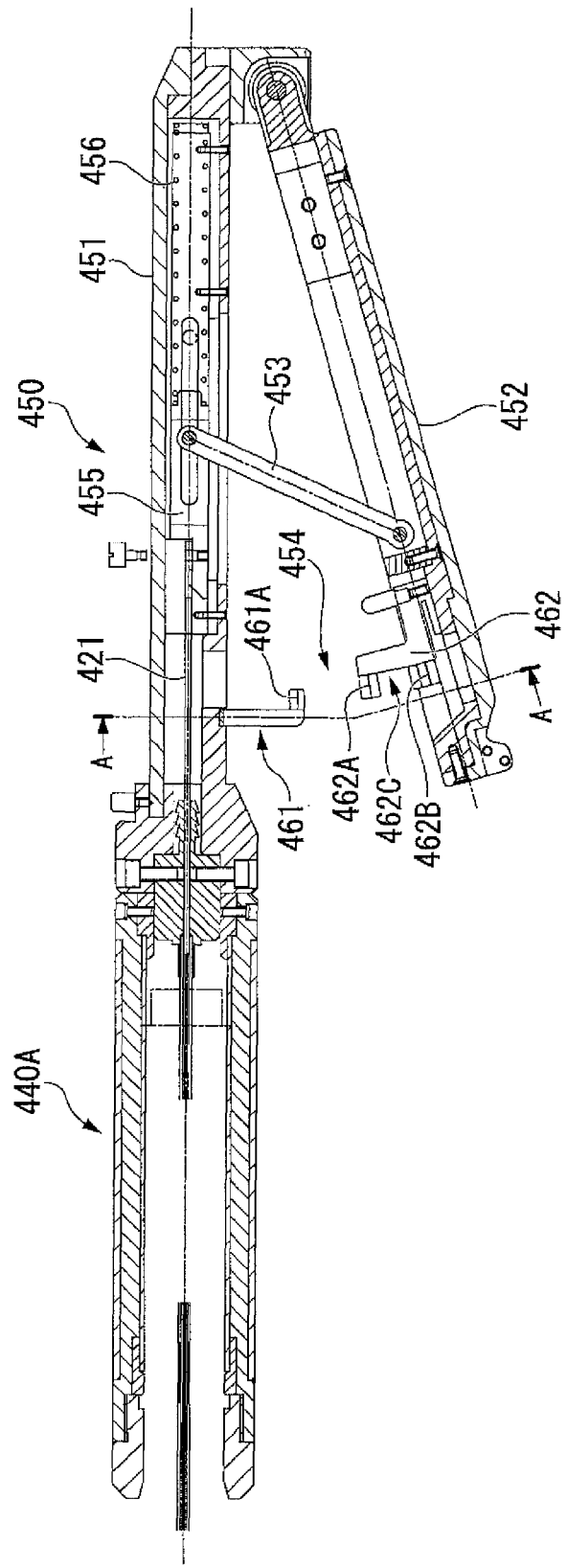
FIG. 61 is a cross-sectional view of a grip and a manipulation section of the treatment instrument in the longitudinal direction thereof of the fourth example of the present invention.

FIG. 61 is a cross-sectional view of the grip 440A and the manipulation section 450 in a longitudinal direction thereof. The proximal end of the manipulation wire 421 is connected to a distal end side of a wire slider 455 disposed in the first holding section 451 to enable the wire slider 455 to advance and retract. A spring 456 is disposed at the proximal end side of the wire slider 455, and biases the wire slider 455 to separate the wire slider 455 from the proximal end of the first holding section 451 by a certain distance or more. Since one end of the link 453 is rotatably connected to the wire slider 455, when the hand is separated from the manipulation section 450, the distal end section of the second holding section 452 and the first holding section 451 are opened to increase the distance therebetween to a certain distance or more, and the forceps section 413 is also opened.

Figure 62:
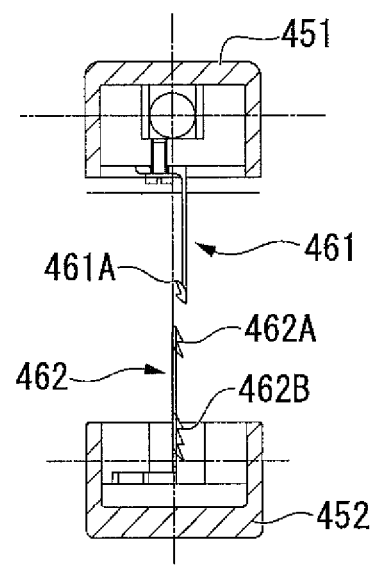
FIG. 62 is a cross-sectional view taken along the line A-A of FIG. 61.

FIG. 62 is a cross-sectional view taken along line A-A of FIG. 61. As shown in FIG. 61 and FIG. 62, the ratchet section 454 includes a first claw section 461 attached to the first holding section 451, and a second claw section 462 configured to be engaged with the first claw section 461 attached to the second holding section 452. A first claw 461A is formed at the first claw section 461. A second claw 462A and a third claw 462B configured to be engaged with the first claw 461A are formed at the second claw section 462. A gap into which the first claw 461A can pass is formed between the second claw 462A and the third claw 462B, and the gap functions as an intermediate release section 462C (described later).

A motion in use of the treatment instrument 404 having the above-mentioned configuration is described. When the curved needle 500 or the like is held by the treatment unit 410, the operator grips the manipulation section 450 to cause the first holding section 451 and the second holding section 452 to approach each other, engaging the first claw 461A with the third claw 462B as shown in FIG. 60. Accordingly, the manipulation wire 421 is sufficiently towed so that the forceps section 413 can hold the curved needle 500 or the like with a large force, and the holding state can be maintained even when the operator separates his/her hand from the manipulation section 450. When the operator causes the first holding section 451 and the second holding section 452 to further approach each other, the first claw 461A and the third claw 462B can be separated to release the engagement thereof.

Figure 63:
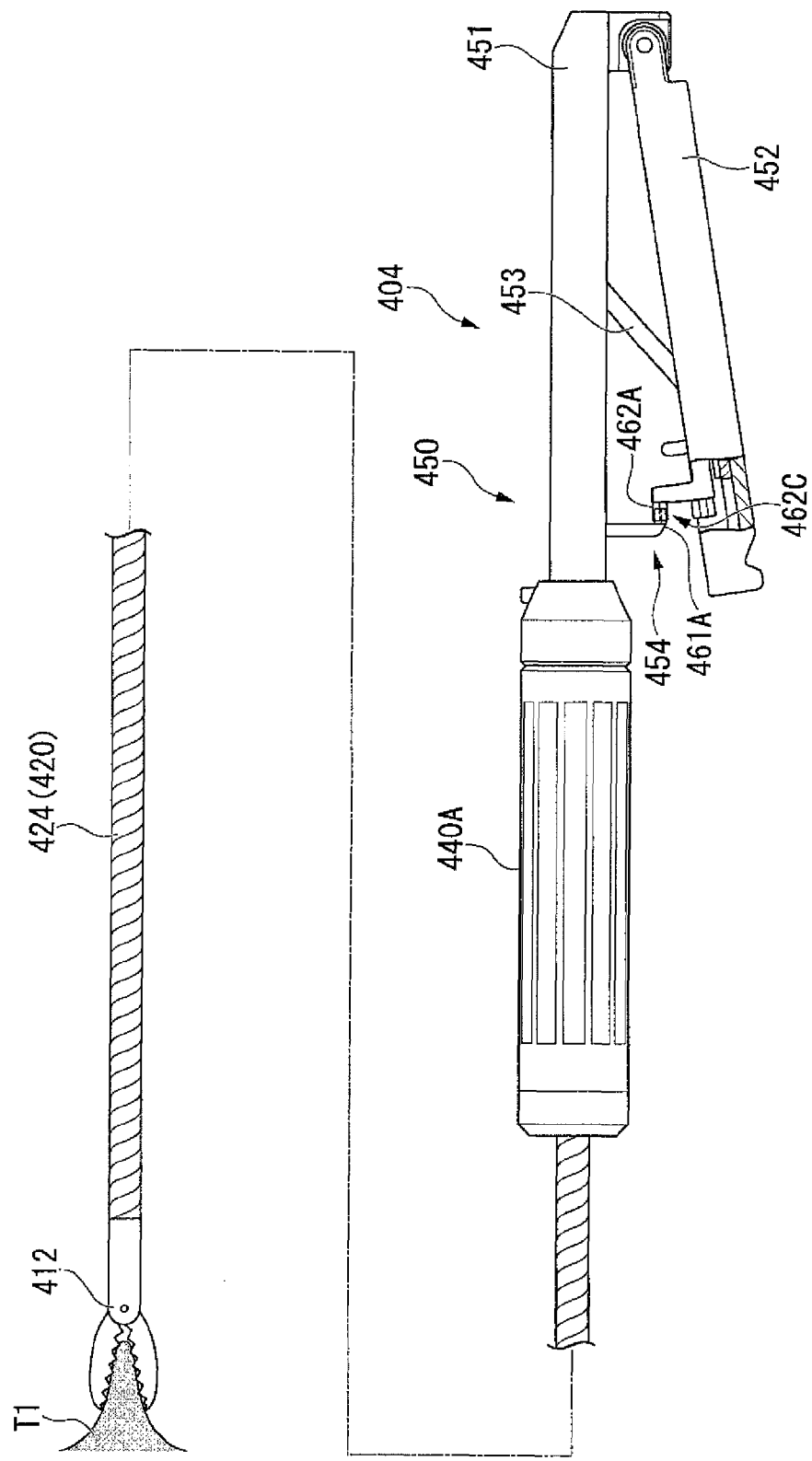
FIG. 63 is a view showing movement of the treatment instrument of the fourth example of the present invention during use.

As shown in FIG. 63, when the distal end side of the treatment instrument 404 is replaced with a new one having the forceps section 412 to be used as a conventional grasping forceps, the operator engages the first claw 461A with the second claw 462A. In this case, a towing amount of the manipulation wire 421 is reduced more than when the first claw 461A and the third claw 462B are engaged with each other, and force generated in the forceps section 412 is further reduced. Accordingly, even when a tissue T1 or the like is gripped with no damage and the hand is separated from the manipulation section 450, the grip state can be maintained.

When the operator causes the first holding section 451 and the second holding section 452 to further approach each other to move the first claw 461A to a position of the intermediate release section 462C, the first claw 461A passes through the intermediate release section 462C to move to the other side of the second claw section 462 (an opposite side of a surface on which the second claw 462A and the third claw 462B are formed), and engagement of the ratchet section 454 is released.

In the treatment instrument for the endoscope, the magnitude of the force to be generated in the treatment unit is different due to the procedures to be performed or a difference in a target object to be gripped. For example, in the needle holder, a relatively large force is needed to securely hold a curved needle or the like, and in the conventional grasping forceps, a smaller force than a force required for the needle holder is needed such that the tissue is not torn or killed.

However, when an engagement mechanism such as a ratchet or the like is attached to the manipulation section to maintain a state in which the target object is gripped, while the magnitude of the force can be adjusted by adjusting an engagement position before the release, the engagement area must be moved at least temporarily to the position to generate the maximum force to perform the release. For this reason, in reality, preparation of the manipulation section having the engagement mechanism according to each of the treatment units is needed.

According to the treatment instrument 404 of the fourth example, since the intermediate release section 462C is formed at the ratchet section 454 to maintain the holding state of the treatment unit, even after the first claw 461A and the second claw 462A are engaged to generate a relatively small force, the engagement can be released without generating a force of the treatment unit equal to or more than the force generated when the first claw 461A and the third claw 462B are engaged with each other. Accordingly, similar to the needle holder and the grasping forceps, two kinds of treatment units having of appropriate forces of different magnitudes in the treatment units can be exchanged and connected, and the forces suitable for the respective treatment units can be generated and the treatment instrument can be used.

In the fourth example, while the example in which the treatment unit is exchanged and used has been described, of course, the treatment instrument may be used to generate two kinds of forces in the same treatment unit, without exchange of the treatment unit.

Figure 64:
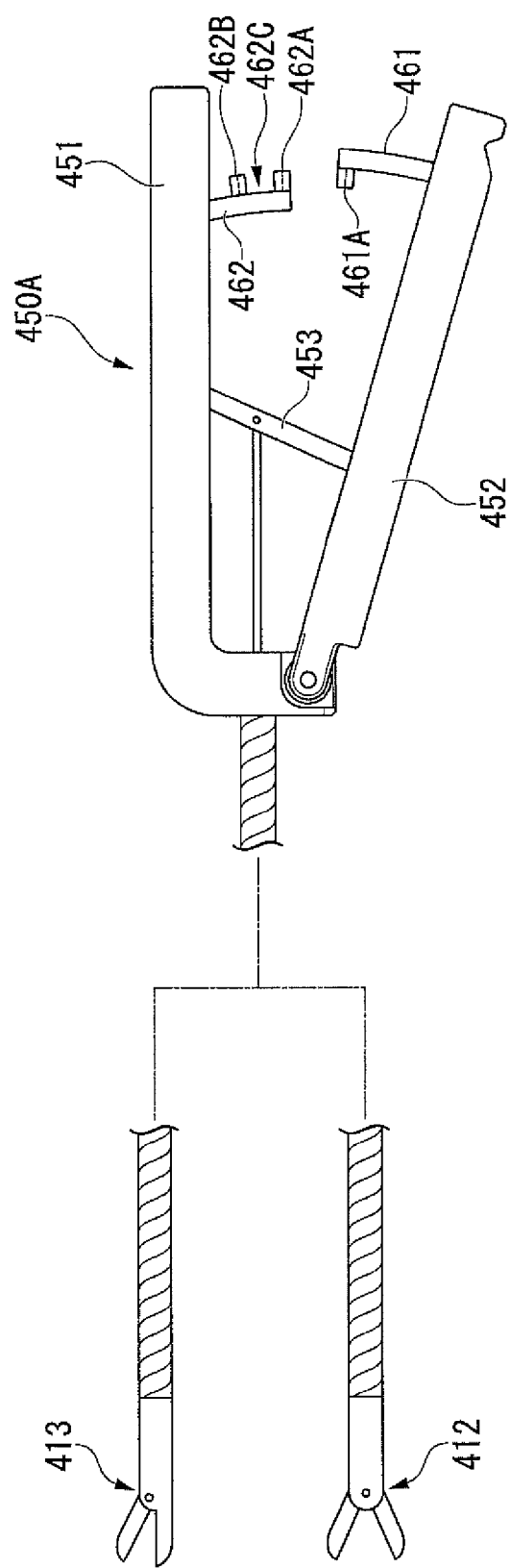
FIG. 64 is a view showing a modified example of the treatment instrument of the fourth example of the present invention.

In addition, like a modified example shown in FIG. 64, instead of the manipulation section 450, a known manipulation section 450A in which the distal end of the second holding section 452 is rotatably connected to the distal end side of the first holding section 451 may be provided. In the modified example, the second claw section 462 is attached to the first holding section 451, and the first claw section 461 is attached to the second holding section 452. As described above, the intermediate release section may be installed at at least one of the first holding section 451 side and the second holding section 452 side, or may be installed at any one of them.

Figure 65:
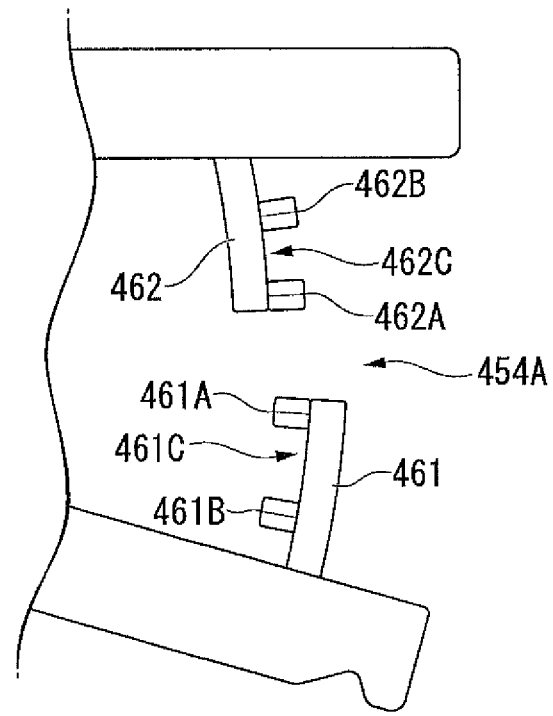
FIG. 65 is a view showing a ratchet section of another modified example of the treatment instrument of the fourth example of the present invention.

Further, as shown in FIG. 65, as a fourth claw 461B is installed at the first claw section 461, an intermediate release section 461C may also be formed at the first claw section 461. In this case, as formation positions of the respective claws 461A, 461B, 462A and 462B are appropriately selected, the positional relation between the first holding section 451 and the second holding section 452 can be maintained in any one of four states in which towing amounts of the manipulation wires 421 are different. Of course, such a ratchet section 454A may be applied to the above-mentioned manipulation section 450.

In the treatment instrument of each of the above-mentioned examples of the present invention, while the example in which the stick of the manipulation section has a cylindrical shape and the grip having substantially cylindrical shape can be fitted onto the stick has been described, shapes of the stick and the grip are not limited thereto.

Figure 66:
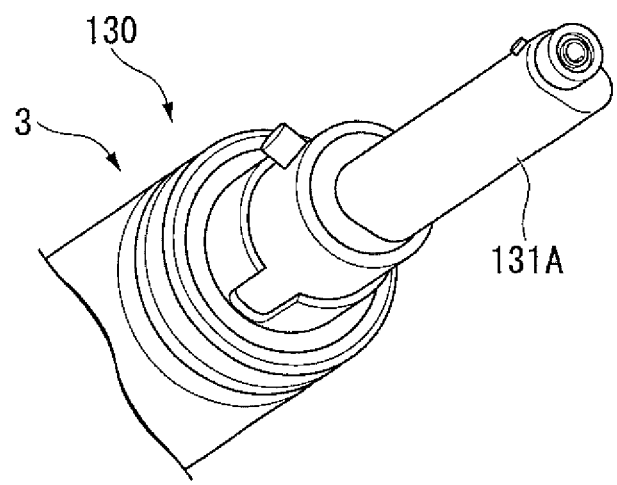
FIG. 66 is a view showing a modified example of a stick of a right arm section.
Figure 67:
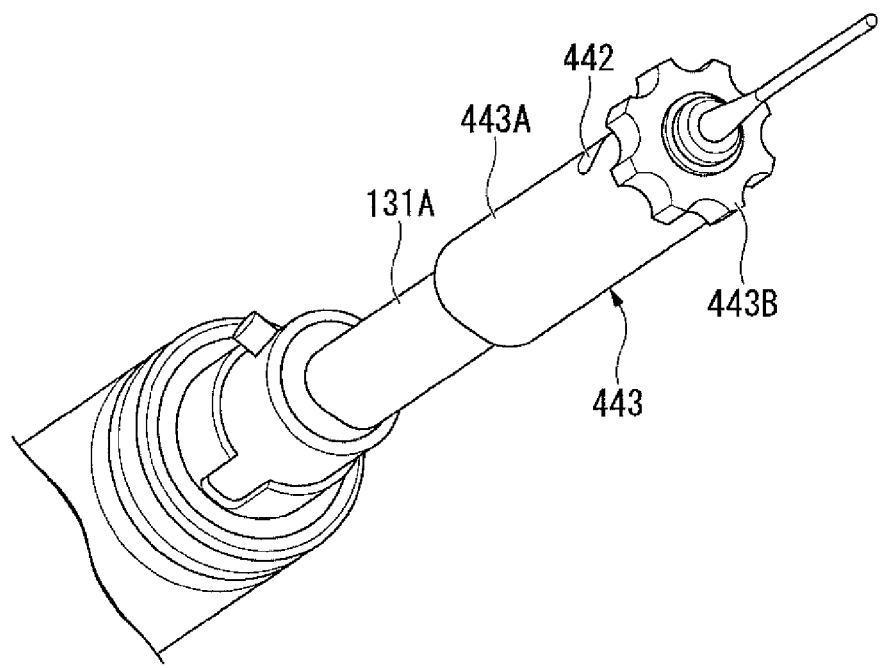
FIG. 67 is a view showing an example of a grip corresponding to the stick of the right arm section.

For example, as shown in FIG. 66, the stick 131A whose cross-sectional shape of the outer circumferential surface is a non-circular shape is used, and as shown in FIG. 67, a grip 443 may have a shape that can be fitted onto the stick 131A. In this case, for example, as a cross-sectional shape of the outer circumferential surface of the stick 131A has an oval shape having a major axis and a minor axis, and the major axis and the minor axis are parallel to a first swing surface and a second swing surface of the swing mechanism, when the operator grips the grip 443, a relation between a direction of pulling down the grip 443 and a bending direction of the active bending section 115 can be intuitively understood. As a result, more accurate manipulation can be performed. However, since the grip cannot be rotated with respect to the stick in this case, in the case of the treatment instrument in which the rotation manipulation is needed, the grip may be rotatably attached to the soft sheath and the hard sheath. Alternatively, as shown in FIG. 67, the grip 443 may be composed of a main body 443A fitted onto the stick and a rotation section 443B rotatably attached with respect to the main body 443A, and the sheath of the treatment instrument may be fixed to the rotation section 443B. As a result, the rotation manipulation of the treatment instrument can be performed by rotating the rotation section 443B.

Figure 68:
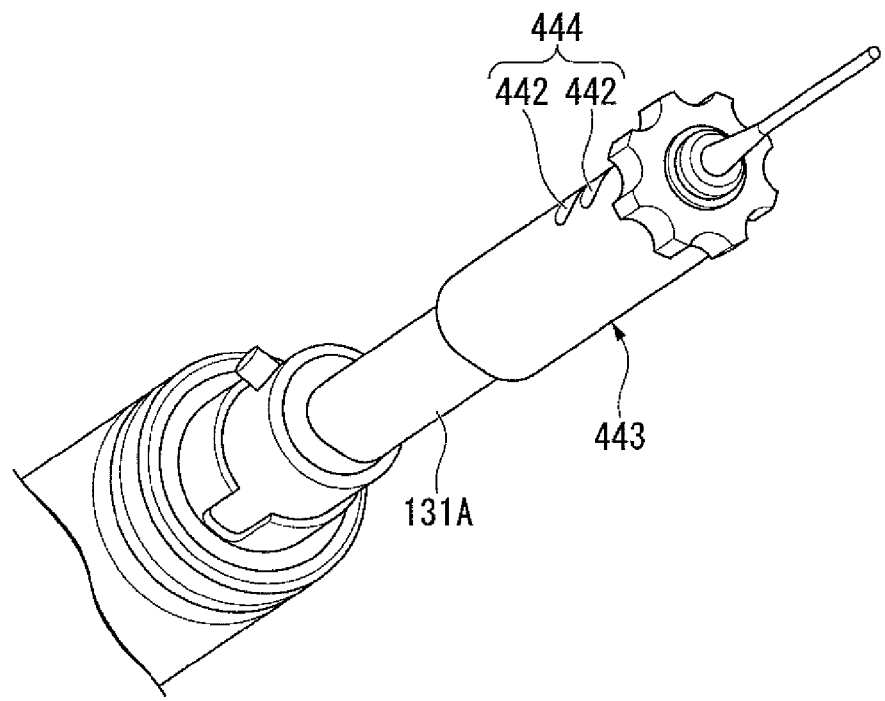
FIG. 68 is a view showing an example of an identification section of the grip.

In addition, an identification section configured to enable recognition by the sense of touch such as a concave section 442 shown in FIG. 67 may be formed at the grip. As a result, as different identification sections are formed at the grip according to the configuration of the treatment unit, the operator can intuitively recognize the configuration of the treatment unit and efficiently perform the procedure. FIG. 68 shows an identification section 444 in which two concave sections 442 are formed as an example. In addition, the identification section is not particularly limited to a specific shape such as a concave or convex shape or the like, a formation position or the number thereof, or the like, as long as the identification section can be recognized by the sense of touch.

(Second Embodiment)

Figure 69:
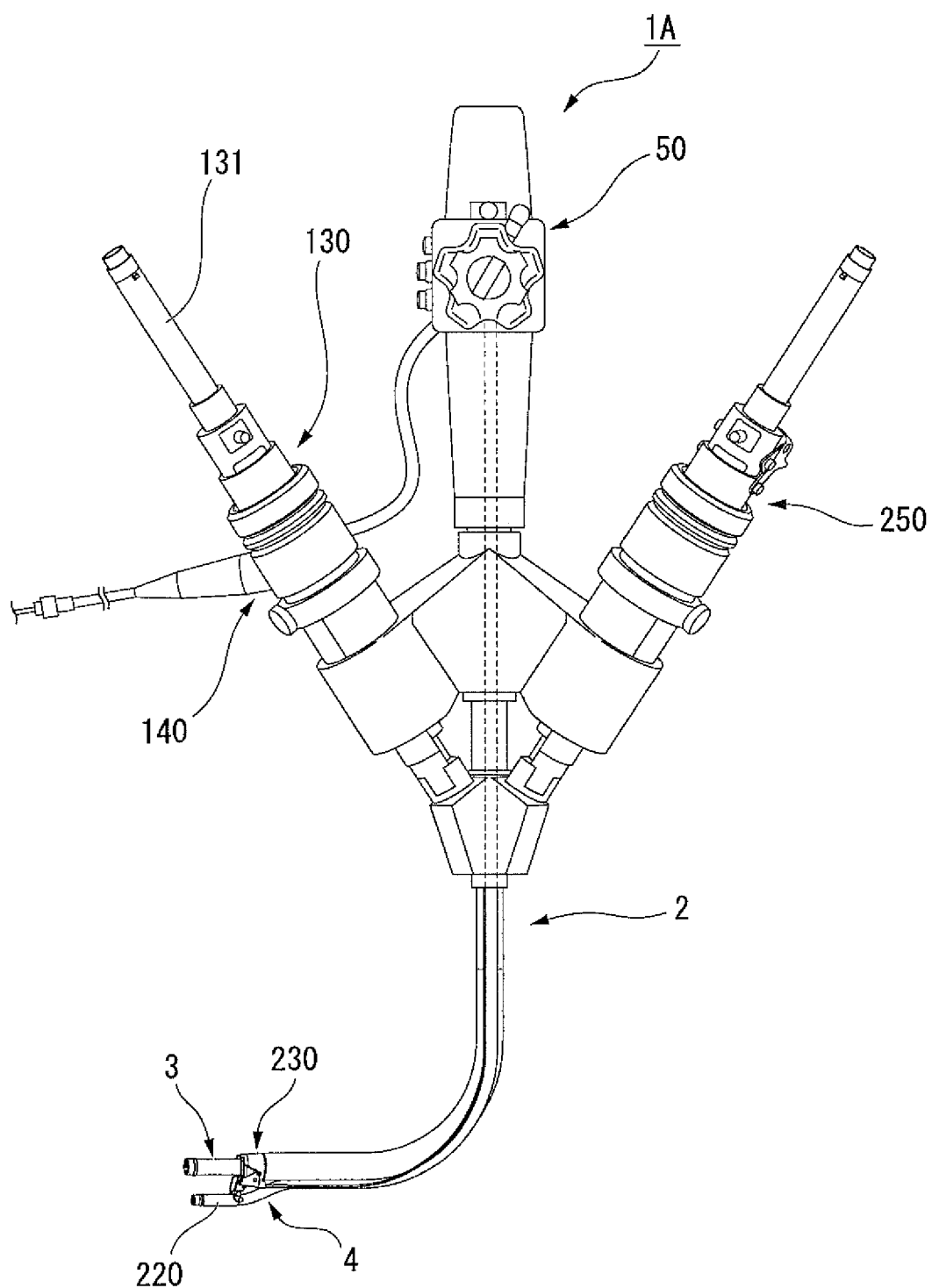
FIG. 69 is an overall view showing an endoscope according to a second embodiment of the present invention.
Figure 70:
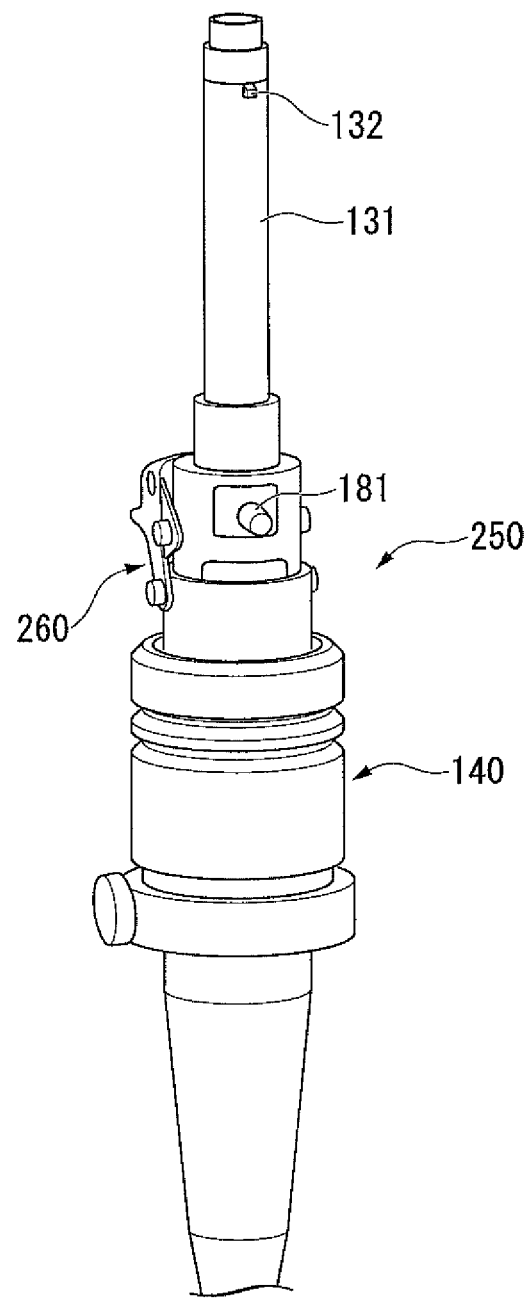
FIG. 70 is an enlarged view of a manipulation section of a left arm section of the endoscope according to the second embodiment of the present invention.

FIG. 69 is an overall view showing an endoscope 1A of a second embodiment of the present invention. In the endoscope 1A, the second dial section 52 is not provided in the manipulation section 50 of the overtube 2, and the forceps hole 55 configured to insert the treatment instrument into the left arm section 4 is also not provided. Instead of this, a manipulation section 250 configured to manipulate the left arm section 4 is provided. As shown in an enlarged view of FIG. 70, the manipulation section 250 has substantially the same structure as the manipulation section 130 of the right arm section 3, and includes a stick 131 and a swing mechanism 140. Accordingly, as the grip of the above-mentioned treatment instrument is fitted onto the stick 131 of the manipulation section 250, advancing/retracting and rotation manipulations of the treatment instrument can be performed and the bending section 220 can be bent in a desired direction.

Since the left arm section 4 includes the bending displacement section 230, the manipulation section 250 includes a displacement manipulation section 260 configured to switch actuation and release of the bending displacement section 230. The manipulation section 250 is distinguished from the manipulation section 130 in this point.

Figure 71:
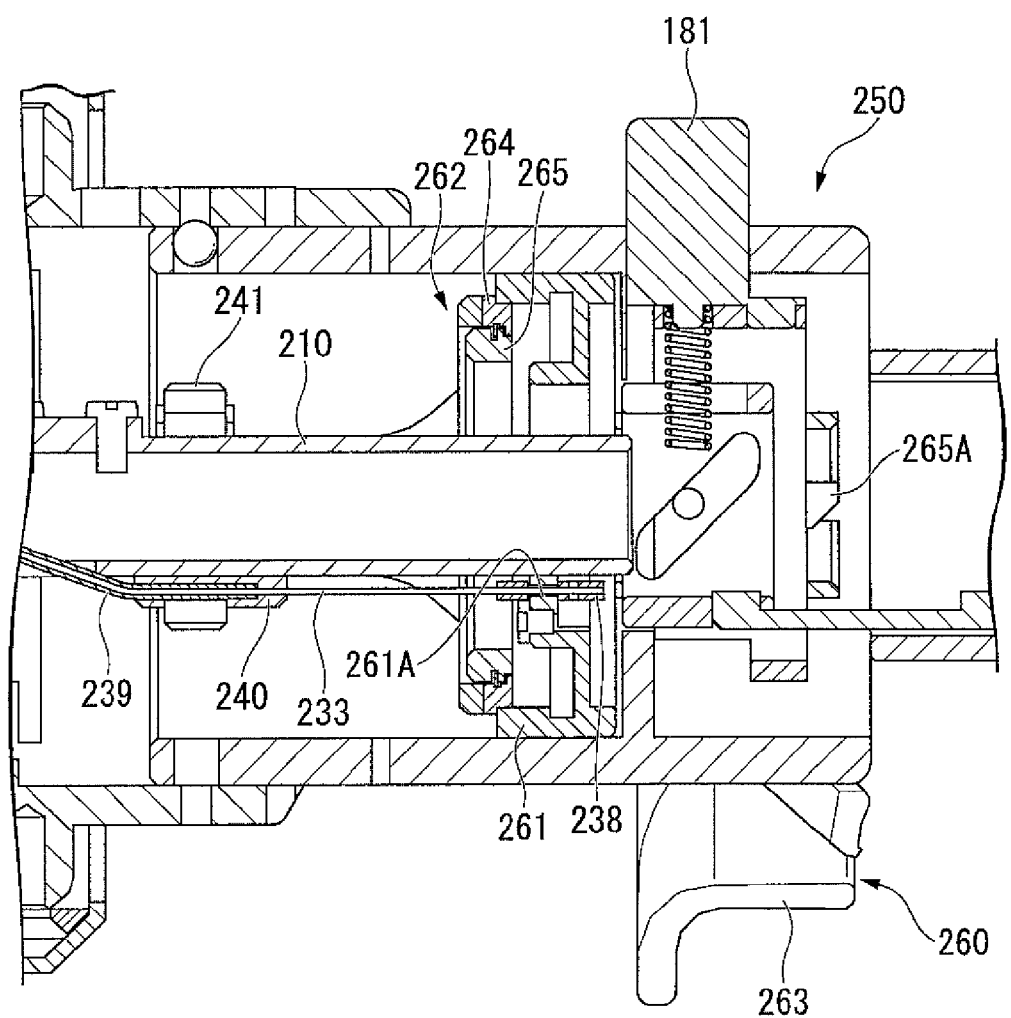
FIG. 71 is a cross-sectional view showing a portion of the manipulation section of the left arm section of the endoscope according to the second embodiment of the present invention.

FIG. 71 is a cross-sectional view showing surroundings of the button 181 configured to manipulate the lock claw 132 of the stick 131 in the manipulation section 250. The displacement manipulation section 260 includes a cylindrical slider 261 to which the towing member 233 is connected, an engagement member 262 attached to the slider 261, and a lever 263 configured to move the slider 261.

The towing member 233 configured to move the bending displacement section 230 is inserted into the coil sheath 239 to extend to the inside of the manipulation section 250. A proximal end of the coil sheath 239 is fixed to a fixing member 240 attached to the channel section 210. The fixing member 240 can be moved to advance and retract in an axial direction of the manipulation section 250 by rotating the adjustment ring 241. A proximal end of the towing member 233 protruding from the coil sheath 239 is connected to the slider 261 disposed in the manipulation section 250.

A stopper 238 is attached to the proximal end of the towing member 233. The stopper 238 has the same shape as the stopper 170 attached to the manipulation member 121 connected to the swing mechanism 140. An engagement hole 261A having the same shape as an engagement hole formed in the fixing member 172 is formed in the slider 261, and the towing member 233 can be inserted into and engaged with the engagement hole 261A of the slider 261 through the same manipulation as the engagement of the manipulation member 121 with the fixing member 172. For this reason, assembly performance of the displacement manipulation section 260 is improved.

The engagement member 262 is composed of an adjustment member 264 screw-fitted to the slider 261, and a claw member 265 relatively rotatably supported with respect to the adjustment member 264. The claw member 265 has an engagement claw 265A engageable with the button 181. As a screw-engaged length between the adjustment member 264 and the slider 261 is adjusted, a positional relation between the slider 261 and the engagement claw 265A can be adjusted.

Figure 72:
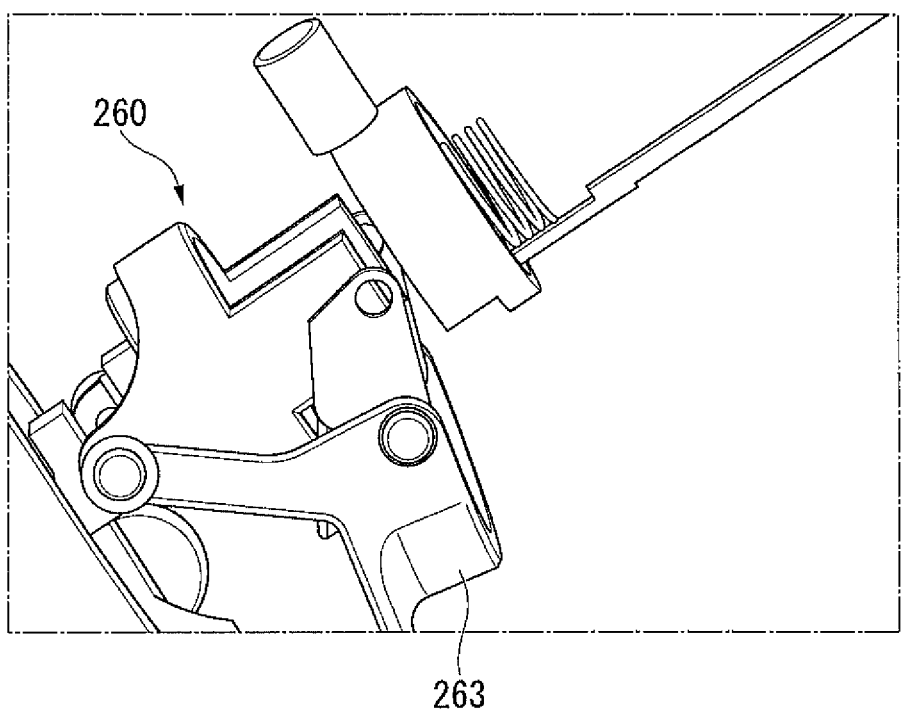
FIG. 72 is a cross-sectional view showing a motion of a displacement manipulation section of the manipulation section of the endoscope according to the second embodiment of the present invention.
Figure 73:
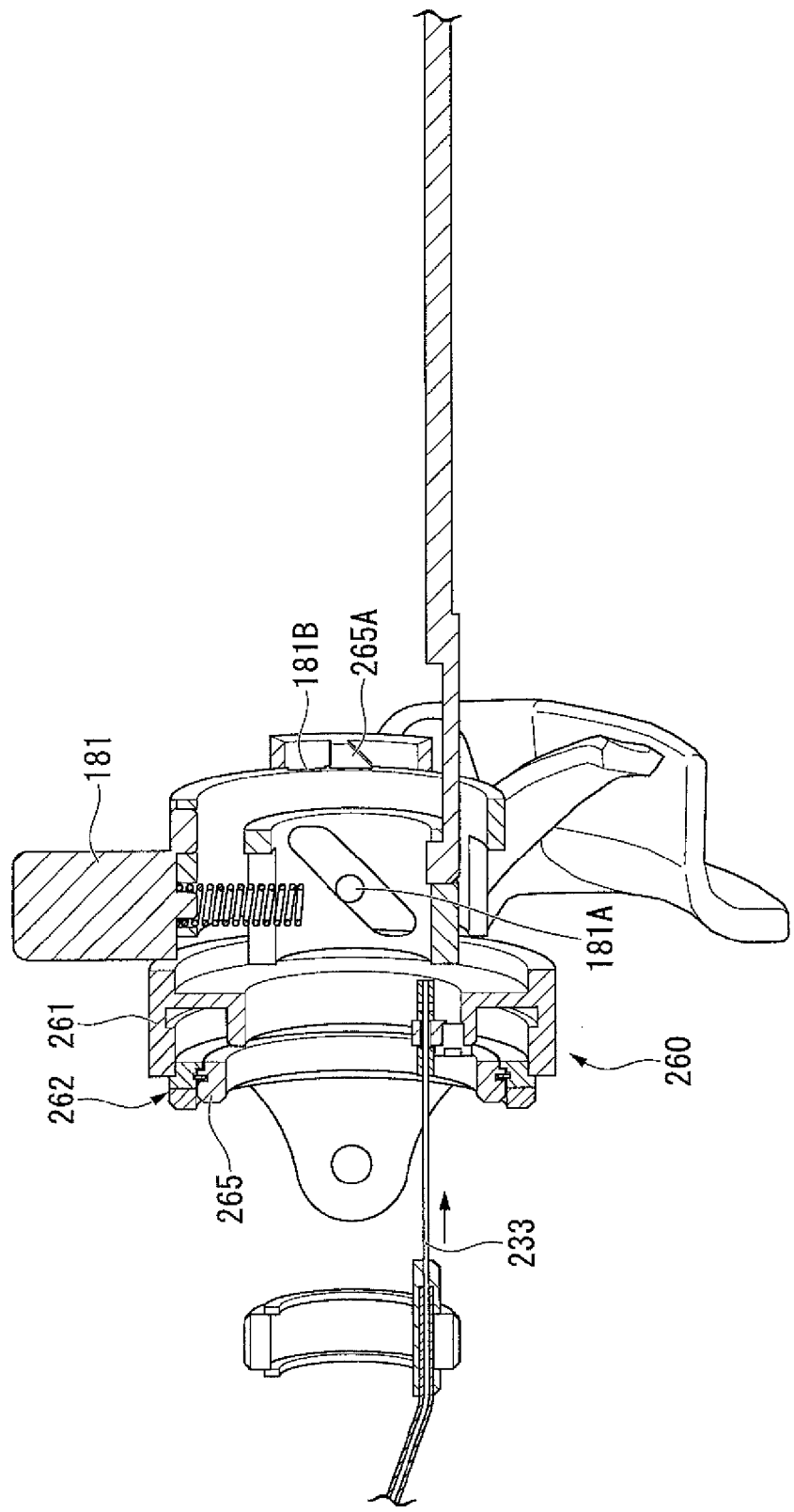
FIG. 73 is a cross-sectional view showing a motion of the displacement manipulation section of the manipulation section of the endoscope according to the second embodiment of the present invention.

A motion of the displacement manipulation section 260 having the above-mentioned configuration is described. When the operator pulls the lever 263 to the proximal end side from a release state shown in FIG. 72, the slider 261 and the engagement member 262 are moved to the proximal end side as shown in FIG. 73, and the towing member 233 is towed to the proximal end side. When the lever 263 is completely pulled, the engagement claw 265A of the claw member 265 is engaged with the proximal end side of the button 181, and the towing state of the towing member 233 is maintained. Then, the bending displacement section 230 becomes an actuation state. In addition, in FIG. 72 and FIG. 73, for easy observation of the respective parts of the displacement manipulation section 260, several members including the stick 131 are omitted here.

When the actuation of the bending displacement section 230 is released, the button 181 is pressed. Then, the button 181 is moved, and a groove 181B installed at the outer circumferential surface (a surface opposite to a surface from which the cam pin 181A protrudes) of the button 181 and the engagement claw 265A are opposed each other. As a result, the engagement member 262 cannot be engaged with the button 181, and the slider 261 and the engagement member 262 are moved to the distal end side to release the actuation state of the bending displacement section 230.

In the left arm section 4, when removal of the treatment instrument is performed while the bending displacement section 230 is actuated, the treatment instrument or the left arm section 4 may be damaged. According to the endoscope 1A of the embodiment, the button 181 configured to manipulate the lock claw 132 upon removal of the treatment instrument is pressed, and the displacement manipulation section 260 is interlocked to release the actuation state of the bending displacement section 230. Accordingly, since the bending displacement section 230 is inevitably released before removal of the treatment instrument, the probability of damage to the treatment instrument or the left arm section 4 may be reduced.

In addition, the manipulation section 250 having substantially the same structure as the manipulation section 130 of the right arm section 3 is provided as the manipulation section of the left arm section 4, both of the right arm section 3 and the left arm section 4 can be intuitively manipulated using the stick 131.

Hereinabove, while the preferred embodiments of the present invention have been described and illustrated, it should be understood that these are exemplary examples of the present invention and are not to be considered as limiting. Additions, omissions, substitutions, and other modifications of the components can be made without departing from the scope of the present invention.

For example, in the above-mentioned embodiments, while the case in which the first arm section having the observation unit is manipulated by a right hand and the second arm section disposed along the overtube is manipulated by a left hand has been described, when the operator is a left-hander, the relationship may be reversed.

The present invention is not to be considered as being limited by the foregoing description, and is only limited by the scope of the appended claims.

(Supplementary Item 1)

A manipulation section including a swing center, wherein the manipulation section is configured to output an input manipulation into the manipulation section to a manipulation member (a wire or the like), a swing mechanism has a lock member configured to automatically lock a swing state of a swing section when a force applied to a manipulation input section is absent, and the swing mechanism further has a lock release prevention unit configured to prevent an automatic lock from being released.

(Supplementary Item 2)

A manipulation section configured to convert an input manipulation to a manipulation input section into an output to a manipulation member (a wire or the like), the manipulation section including:

a swing mechanism having a first swing section configured to swing about different swing centers in two directions parallel to a first swing surface, and a second swing section configured to swing about different swing centers in two directions parallel to a second swing surface perpendicular to the first swing surface, wherein, the swing mechanism has an automatic lock mechanism configured to hold a swing state of the first swing section and the second swing section when a force applied to the manipulation input section disappears, and the swing mechanism further has a lock release prevention unit configured to prevent an automatic lock from being released.

(Supplementary Item 3)

The automatic lock mechanism according to supplementary item 2, wherein the automatic lock mechanism includes: a base frame; a towing body to which a manipulation member is connected; sandwich members attached to the base frame; and a drive base disposed to sandwich and oppose the base frame, the towing body, and the sandwich members, the base frame has a pair of driving force transmission members and a release member attached to both ends in a widthwise direction thereof, a pin is installed in the towing body at a symmetrical position that sandwiches a center in the widthwise direction as a swing center, the manipulation member is connected to both ends of the towing body in the widthwise direction, a pair of locking grooves configured to fix a swing state of a swing section is formed at an area between the pin and the manipulation member in the widthwise direction of the towing body, each of the locking grooves is formed in an arc shape about the pin, and a bottom surface of each of the locking grooves is inclined at a slight angle to become shallow as approaching a proximal end side thereof, the base is fixed with respect to the manipulation section and has a pair of guide holes, and one of the pair of guide holes is formed in an arc shape about a lower end of the other of the pair of guide hole, in each of the sandwich members, biasing members are attached to both ends in the widthwise direction, and a lock member is disposed between each of the biasing members and a lock release member, a diameter dimension of the lock member is smaller than a width of a ball moving groove formed in each of the locking grooves and guide grooves opposite to the locking grooves, and larger than a width of the proximal end side, and the sandwich member is attached to the base frame such that the pin is inserted into a long hole.

(Supplementary Item 4)

The towing body is biased in a direction spaced apart from the base frame, and the pin is biased toward a lower end of the long hole by a biasing member disposed between the base frame and the towing body.

(Supplementary Item 5)

The manipulation member according to supplementary item 1 is connected to an active bending section.

(Supplementary Item 6)

The manipulation section according to supplementary item 3, wherein the lock release prevention unit is a spacer disposed to enter between a push member and the towing body.

(Supplementary Item 7)

The manipulation section according to supplementary item 3, wherein a release prevention member includes an arbitrary lock manipulation member (a hood) installed at the swing section, a cylinder inserted into the base frame, a spacer disposed to enter between the push member and the towing body, and a link connecting the cylinder and the spacer, and the arbitrary lock manipulation member (the hood) is connected to the cylinder.

(Supplementary Item 8)

The manipulation section according to supplementary item 7 has the arbitrary lock manipulation member (the hood), an adjuster attached to the arbitrary lock manipulation member (the hood), and a cylinder section, and the cylinder section is pressed by the adjuster.

(Supplementary Item 9)

The adjuster according to supplementary item 8 is disposed on the cylinder section and substantially parallel to the widthwise direction of the first swing section, and has a first arc section extending to the pin side, and a second arc section extending to the pin side.

(Supplementary Item 10)

The bending section according to supplementary item 5 includes a treatment instrument channel into which the treatment instrument is able to be inserted and in communication with the manipulation section.

(Supplementary Item 11)

An endoscope including:

an insertion section having a bending section configured to enable a bending manipulation; and a manipulation section having a joy stick and configured to manipulate the bending section, wherein the manipulation section further includes a swing mechanism having a first swing section configured to swing about different swing centers in two directions parallel to a first swing surface, and a second swing section configured to swing about different swing centers in two direction parallel to a second swing surface perpendicular to the first swing surface, and all the swing centers of both of the first swing section and the second swing section are disposed on substantially the same plane perpendicular to an axis of the manipulation section.

(Supplementary Item 12)

An endoscope including:

an overtube including a first insertion section having flexibility and a long shape, the first insertion section having a first bending section configured to enable a bending manipulation, and a first manipulation section configured to manipulate the first bending section;

a first arm section including a second insertion section having flexibility and a long shape, the second insertion section having a second bending section configured to enable a bending manipulation and a treatment instrument channel into which a treatment instrument is able to be inserted, an observation unit installed at a distal end of the second insertion section, and a second manipulation section having a joy stick into which the treatment instrument is able to be inserted and configured to manipulate the second bending section, the first arm section inserted into the first insertion section to enable advancing and retracting thereof; and a second arm section including a channel section having flexibility and a long shape, the channel section disposed along the first insertion section, a third bending section installed at a distal end side of the channel section, a bending displacement section capable of holding the third bending section with spaced a certain distance from the first insertion section, and a third manipulation section configured to manipulate the third bending section and the bending displacement section, wherein the second manipulation section further includes a swing mechanism having a first swing section configured to swing about different swing centers in two directions parallel to a first swing surface, and a second swing section configured to swing about different swing centers in two direction parallel to a second swing surface perpendicular to the first swing surface, and all the swing centers of both of the first swing section and the second swing section are disposed on substantially the same plane perpendicular to an axis of the second manipulation section.

(Supplementary Item 13)

A medical instrument system including:

a manipulation section applicable to a treatment instrument for an endoscope, the manipulation section having a treatment unit configured to perform treatment with respect to a living body tissue, a manipulation member connected to the treatment unit, and a sheath into which the manipulation member is inserted to be able to advance and retract, wherein the manipulation section includes;

a first holding section to which a proximal end of the sheath is fixed;

a second holding section rotatably supported with respect to the first holding section and moving the manipulation member to advance and retract by rotating; and a ratchet section holding a relative positional relation between the first holding section and the second holding section, and the ratchet section includes:

a first claw section installed at one of the first holding section and the second holding section and having a first claw;

a second claw section installed at the other of the first holding section and the second holding section and having a second claw and a third claw engaged with the first claw; and an intermediate release section installed between the second claw and the third claw and releasing engagement between the first claw and the second claw.

(Supplementary Item 14)

The medical instrument system according to supplementary item 13, wherein the treatment unit has a grip section.

(Supplementary Item 15)

An endoscope including:

a elongated member including a first insertion section having a first bending section configured to enable a bending manipulation, and a first manipulation section configured to manipulate the first bending section; and a first arm section including a second insertion section having a second bending section configured to enable a bending manipulation, and a second manipulation section configured to manipulate the second bending section, the first arm section being inserted into the first insertion section to be able to advance and retract, wherein the second manipulation section is supported with respect to the first manipulation section to enable rotation about a shaft center of the first manipulation section.

(Supplementary Item 16)

The endoscope according to supplementary item 15, wherein the first insertion section further includes an opening into which the second insertion section is inserted, and a branch member having an insertion hole into which the second insertion section is inserted, the branch member covering the opening, and the branch member enables rotation with respect to the first insertion section.

(Supplementary Item 17)

The endoscope according to supplementary item 16, further including a tubular member into which the second insertion section is able to be inserted, disposed in the first insertion section, wherein a proximal end side of the tubular member is rotatably fixed with respect to the opening of the branch member.

(Supplementary Item 18)

The endoscope according to supplementary item 15, wherein the second insertion section includes the second bending section and a sheath disposed at a proximal end side thereof, and the sheath includes a first sheath and a second sheath rotatably connected to the first sheath.

(Supplementary Item 19)

The endoscope according to supplementary item 15, further including a treatment instrument channel disposed in the second insertion section, wherein the treatment instrument channel has a first channel and a second channel rotatably connected to the first channel.

(Supplementary Item 20)

The endoscope according to supplementary item 15, wherein the second manipulation section is a joy stick.

(Supplementary Item 21)

A treatment instrument used with the endoscope according to supplementary item 16, including:

a treatment unit configured to perform treatment with respect to a living body tissue;

a manipulation section configured to manipulate the treatment unit;

a manipulation member connecting the treatment unit and the manipulation section;

a soft sheath into which the manipulation member is inserted to enable advancing and retracting;

a hard sheath into which the manipulation member is inserted to enable advancing and retracting, the hard sheath disposed at a proximal end side of the soft sheath; and a grip attached to the hard sheath, wherein the grip is fitted onto a channel sheath rigid section installed at a channel sheath proximal end section into which the treatment instrument is inserted, and a length of the hard sheath is set such that at least a portion of the hard sheath is disposed in the channel sheath rigid section when the fitted grip is fully retracted with respect to the channel sheath rigid section.

(Supplementary Item 22)

The treatment instrument according to supplementary item 21, wherein the manipulation section is rotatably connected with respect to the grip.

(Supplementary Item 23)

The endoscope according to supplementary item 19, wherein the treatment instrument channel includes the first bending section or the second bending section at the distal end section, and the first manipulation section configured to manipulate the first bending section or the second manipulation section configured to manipulate the second bending section, the first manipulation section or the second manipulation section is a joy stick structure, the second insertion section comprises a soft sheath and a hard sheath disposed at a proximal end side of the soft sheath, and the hard sheath is a manipulation input section of the joy stick structure.

What is claimed is:

1. An endoscope comprising:
   an elongated member having a distal end section and a proximal end section, the elongated member including
   a first insertion section,
   the first insertion section having a longitudinal axis and a channel disposed along the longitudinal axis, the channel extending from the distal end section to the proximal end section;
   a second insertion section having a distal end side corrugated tube, which extends along the longitudinal axis, and a proximal end side corrugated tube, which is rotatably attached to a proximal end portion of the distal end side corrugated tube so that the proximal end side corrugated tube rotates about a central axis of the proximal end side corrugated tube relative to the distal end side corrugated tube, the second insertion section being disposed in the channel of the first insertion section so that the second insertion section is configured to advance and retract;

a branch section having an insertion hole that communicates with the channel of the first insertion section such that the proximal end side corrugated tube protrudes radially outward from the channel in a state when the second insertion section is inserted into the channel, the branch section being disposed so as to rotate about the longitudinal axis of the first insertion section;

an active bending section disposed at a distal end portion of the distal end side corrugated tube, the active bending section being capable of bending;

a stick configured to be inclinable so as to bend the active bending section; and a swing mechanism disposed at the proximal end side corrugated tube, the swing mechanism being configured to support the stick such that the stick is inclinable on two planes that are perpendicular to each other and cross each other, the swing mechanism being configured to pivot with the stick about the central axis of the proximal end side corrugated tube.

2. The endoscope according to claim 1, wherein the stick is configured to rotate with the branch section about the longitudinal axis of the first insertion section.

3. The endoscope according to claim 1, wherein the second insertion section further includes a treatment instrument channel, the treatment instrument channel having a first channel and a second channel, the second channel being connected to the first channel such that the second channel is capable of rotating about a longitudinal axis of the treatment instrument channel relative to the first channel.

4. The endoscope according to claim 1, wherein the swing mechanism is configured to support the stick such that the stick is inclinable only on the two planes.

* * * * *